(12) United States Patent
Yang et al.

(10) Patent No.: US 10,877,051 B2
(45) Date of Patent: Dec. 29, 2020

(54) BISTRIFLATE-BASED FLUOROGENIC PROBES FOR DETECTION OF SUPEROXIDE ANION RADICAL

(71) Applicant: THE UNIVERSITY OF HONG KONG, Hong Kong (CN)

(72) Inventors: Dan Yang, Hong Kong (CI); Nai-Kei Wong, Hong Kong (CI); Jun Hu, Hong Kong (CI)

(73) Assignee: THE UNIVERSITY OF HONG KONG, Hong Kong (CN)

(*) Notice: Subject to any disclaimer, the term of this patent is extended or adjusted under 35 U.S.C. 154(b) by 149 days.

(21) Appl. No.: 14/597,408

(22) Filed: Jan. 15, 2015

(65) Prior Publication Data
US 2015/0219676 A1    Aug. 6, 2015

Related U.S. Application Data

(60) Provisional application No. 61/934,335, filed on Jan. 31, 2014.

(51) Int. Cl.
| | | |
|---|---|---|
| G01N 33/84 | (2006.01) |
| C07F 9/6561 | (2006.01) |
| C07D 311/82 | (2006.01) |
| C07D 491/20 | (2006.01) |
| C07D 493/10 | (2006.01) |
| C07F 7/08 | (2006.01) |
| G01N 33/58 | (2006.01) |

(52) U.S. Cl.
CPC .......... *G01N 33/84* (2013.01); *C07D 311/82* (2013.01); *C07D 491/20* (2013.01); *C07D 493/10* (2013.01); *C07F 7/0816* (2013.01); *C07F 9/6561* (2013.01); *G01N 33/582* (2013.01)

(58) Field of Classification Search
None
See application file for complete search history.

(56) References Cited

U.S. PATENT DOCUMENTS

| 8,114,904 B2 * | 2/2012 | Yang .................... C07D 307/94 |
| | | 435/14 |
| 2009/0253143 A1 | 10/2009 | Yang et al. |
| 2011/0159603 A1 | 6/2011 | Nagano et al. |
| 2013/0196362 A1 * | 8/2013 | Yang .................... C07F 9/6561 |
| | | 435/29 |

FOREIGN PATENT DOCUMENTS

| CN | 102146284 | 8/2011 |
| WO | WO 2013/113279 | 8/2013 |

OTHER PUBLICATIONS

Sun et al. "Synthesis of Fluorinated Fluoresceins", J. Org. Chem. 1997, 62, 6469-6475.*
Carey et al. "Advanced Organic Chemistry",2000, 4th Ed, Kluwer Academic/Plenum Publishers, pp. 295-297.*
Dickinson, Bryan C. et al., "A Palette of Fluorescent Probes with Varying Emission Colors for Imaging Hydrogen Peroxide Signaling in Living Cells", J. Am. Chem. Soc., 132, 5906-5915, Apr. 2, 2010.
Peng, Tao et al., "Construction of a Library of Rhodol Fluorophores for Developing New Fluorescent Probes", Nov. 23, 2009, American Chemical Soceity, vol. 12, No. 3, 496-499.
Peng, Tao et al., "HKGreen-3: A Rhodol-Based Fluorescent Probe for Peroxynitrite", Sep. 12, 2010, American Chemical Soceity, vol. 12, No. 21, 4932-4935.

* cited by examiner

*Primary Examiner* — James W Rogers
(74) *Attorney, Agent, or Firm* — Leason Ellis LLP

(57) ABSTRACT

The invention provides fluorogenic compounds and probes that can be used as reagents for measuring, detecting and/or screening superoxide. The fluorogenic compounds of the invention can produce fluorescence colors, such as green, yellow, red, or far-red. The invention further provides fluorogenic compounds for selectively staining superoxide in the mitochondria of living cells. The invention also provides methods that can be used to measure, directly or indirectly, the presence and/or amount of superoxide in chemical samples and biological samples such as cells and tissues in living organisms, and a high-throughput screening methods for detecting or screening superoxide or compounds that can increase or decrease the level of superoxide in chemical and biological samples.

9 Claims, 13 Drawing Sheets

BISTRIFILATE-BASED FLUOROGENIC PROBES FOR DETECTION OF SUPEROXIDE ANION RADICAL

CROSS-REFERENCE TO RELATED APPLICATION

This application claims priority from U.S. Provisional Application Ser. No. 61/934,335, filed Jan. 31, 2014. The entire contents of this prior application are incorporated herein by reference.

BACKGROUND OF THE INVENTION

The generation of superoxide ($O_2^-$) reactive oxygen or nitrogen species is implicated in the pathophysiological process associated with aging, inflammation and even progression of several diseases, such as cancer and diabetes.

In order to investigate the mechanism of those reactive species involved in the biological reactivities, some analytical approaches such as chemiluminescence and fluorescence have been developed to detect the intracellular generation of reactive species, especially the generation of superoxide in mitochondria. These probes work as a tool to study the oxidative stress in various pathologies. For example, dihydroethidium (HE) and MitoSOX detect intracellular and mitochondrial $O_2^-$ to form 2-OH-$E^+$ and 2-OH-Mito-$E^+$, respectively. The oxidized species will intercalate with nucleic acid and give out red fluorescence. However, HE and MitoSOX are also oxidized by other reactive oxidants to give E+ and Mito-$E^+$. 2-OH-$E^+$, $E^+$, 2-OH-Mito-$E^+$ and Mito-$E^+$ have similar fluorescent spectral properties. Therefore, further analytical measurement like HPLC is employed to distinguish the oxidized species. As such, the currently available superoxide probes have limited sensitivity and selectivity.

SUMMARY OF THE INVENTION

The present invention is directed to novel bistriflate-based compounds and their use as reliable and accurate fluorogenic probes for detection of superoxide anion radicals.

In one aspect, the present invention provides bistriflate-based compounds of Formula (I) and Formula (II):

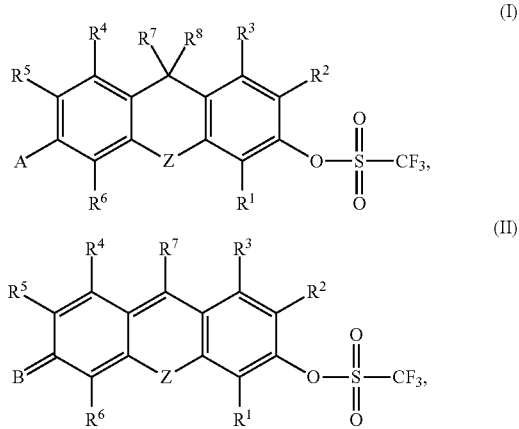

including tautomers thereof.

Each of $R^1$ and $R^2$ is independently F, Cl or H;
each of $R^3$, $R^4$, $R^5$ and $R^6$ is independently H, F, Cl, Br, I, CN, alkyl, halogenated alkyl, heteroalkyl, alkenyl, alkynyl, aralkyl, aryl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thiol, thioalkyl, alkoxy, alkylthio, alkoxyalkyl, aryloxy, arylalkoxy, acyloxy, nitro, carbamoyl, trifluoromethyl, phenoxy, benzyloxy, phosphonic acid, phosphate ester, sulfonic acid (—$SO_3H$), sulfonamide, —C(=O)—$P^1$ or —C(=O)-M-$P^2$; wherein each of $P^1$ and $P^2$ is independently hydrogen, halo, alkoxy, hydroxy, thiol, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, alkyltriphenylphosphonium, or heterocyclyl having from 3 to 7 ring atoms; M is alkylene, alkenylene, alkynylene, arylene, aralkylene or alkarylene;

A is $OR^9$ or $NR^{10}R^{11}$; wherein $R^9$ is H, alkyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, carboxyalkyl, alkoxycarbonyl, acyl or aminocarbonyl; wherein each of $R^{10}$ and $R^{11}$ is independently H, alkyl, halogenated alkyl, alkenyl, alkynyl, alkoxyalkyl, heteroalkyl, cycloalkyl, cycloalkenyl, cycloalkynyl, heterocyclyl, aminoalkyl, arylalkyl, alkyloxy, acyl, carboxyalkyl, sulfoalkyl, a salt of carboxyalkyl, a salt of sulfoalkyl, or an ester or amide of carboxyalkyl or sulfoalkyl; or $R^{10}$ in combination with $R^{11}$ forms a saturated 5- or 6-membered heterocycle that is a piperidine, a morpholine, a pyrrolidine or a piperazine, each of which is optionally substituted by alkyl, carboxylic acid, a salt of carboxylic acid, or a carboxylic acid ester of an alcohol; or $R^{10}$ in combination with $R^5$, or $R^{11}$ in combination with $R^6$, or both, form a 5- or 6-membered ring that is saturated or unsaturated, or further fused with an aryl or heteroaryl ring, and is optionally substituted by one or more alkyls, carboxylic acids, sulfonic acids (—$SO_3H$), or their salts, ester or amide derivatives;

B is O or $N^+R^{10}R^{11}$;
Z is O, S, $NR^{12}$, $CR^{12}R^{13}$, $SiR^{12}R^{13}$, $GeR^{12}R^{13}$ or $SnR^{12}R^{13}$; wherein each of $R^{12}$ and $R^{13}$ is independently H, alkyl, halogenated alkyl, heteroalkyl, alkenyl, alkynyl, aralkyl, aryl, alkaryl, heterocyclyl, cycloalkyl, cycloalkenyl, cycloalkynyl, hydroxyalkyl, aminoalkyl, hydroxy, thiol, thioalkyl, alkoxy, alkylthio, alkoxyalkyl, aryloxy, arylalkoxy, acyloxy, carbamoyl, trifluoromethyl, phenoxy, benzyloxy, phosphoric acid, phosphate ester, sulfonic acid (—$SO_3H$), sulfonamide, carboxylic acid, carboxylic ester, or carboxylic amide; or $R^{12}$ in combination with $R^{13}$ forms a saturated 5- or 6-membered heterocycle that is optionally substituted by alkyl, carboxylic acid, a salt of carboxylic acid, or a carboxylic acid ester of an alcohol;

$R^7$ is H, $CF_3$, CN, a carboxylic acid, a salt of carboxylic acid, or a carboxylic acid ester of an alcohol; or $R^7$ is a saturated or unsaturated alkyl that is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—$SO_3H$), sulfonamide (—$SO_2NR^{14}R^{15}$), wherein each of $R^{14}$ and $R^{15}$ represents a saturated or unsaturated, cyclic or acyclic alkyl that is optionally substituted by one or more F, Cl, Br, I, a carboxylic acid, a salt of carboxylic acid, a carboxylic acid ester of an alcohol, amino, alkylamino, dialkylamino, alkoxy, or alkyltriphenylphosphonium, In some embodiments, $R^7$ is Formula (III):

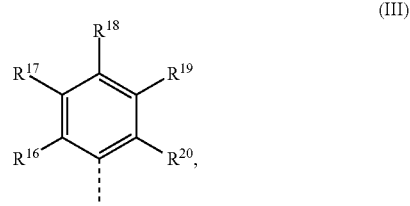

(III)

wherein each of $R^{16}$, $R^{17}$, $R^{18}$, $R^{19}$ and $R^{20}$ is independently H, F, Cl, Br, I, CN, nitro, a carboxylic acid, a salt of carboxylic acid, sulfonic acid (—$SO_3H$), sulfonamide (—$SO_2NR^{14}R^{15}$), hydroxy, azide, alkyl, alkenyl, alkynyl, heteroalkyl, cycloalkyl, cycloalkenyl, cycloalkynyl, aryl, alkylaryl, arylalkyl, heterocyclyl, alkoxy, alkoxyalkyl, alkoxyalkoxy, acyl, alkylcarbonylalkyl, halogenated alkyl, aminoalkyl, carboxyalkyl, thiol, alkylthio, amino, alkylamino, dialkylamino, alkoxycarbonyl, alkoxycarbonylalkyl, aminocarbonyl, alkylaminocarbonyl, dialkylaminocarbonyl, or arylcarboxamido, the alkyl or aryl of which is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—$SO_3H$), or sulfonamide (—$SO_2NR^{14}R^{15}$); or $R^{16}$ and $R_{17}$ together, $R^{17}$ and $R^{18}$ together, $R^{18}$ and $R^{19}$ together, or $R^{19}$ and $R^{20}$ together form a part of a 5- or 6-membered cycloalkyl, heterocyclyl, aryl or heteroaryl ring fused with the phenyl ring of Formula (III) that is optionally further substituted by one or more F, Cl, Br, I, a carboxylic acid, a salt of carboxylic acid, a carboxylic acid ester of an alcohol, amino, alkylamino, dialkylamino, alkoxy, thiol, alkylthio, alkyltriphenylphosphonium, sulfonic acid (—$SO_3H$), or sulfonamide (—$SO_2NR^{14}R^{15}$); and $R^8$ is H, hydroxy, CN or alkoxy; or $R^7$ in combination with $R^8$ forms a 5-membered spirolactone or spirolactam ring or a 5-membered spirosultam ring; or $R^8$ in combination with $R^{16}$ or $R^{20}$ forms a 5- or 6-membered spirolactone or spirolactam ring or a 5- or 6-membered spirosultone or spirosultam ring that is optionally and independently substituted by H, F or $CH_3$.

In method aspects of the present invention, a high-throughput screening method for detecting the presence of, or determining the level of, superoxide in a sample is provided. The method comprises contacting a compound of Formula (I) or Formula (II) with the sample to form one or more fluorescent compounds; and determining fluorescence properties of the fluorescent compounds to determine the presence and/or amount of superoxide in the sample.

In another method aspect of the present invention, a high-throughput method for screening one or more target compounds that increase or decrease the level of superoxide is provided. The method comprises contacting a compound of Formula (I) or Formula (II) with the target compounds to form one or more fluorescent compounds; and measuring fluorescence properties of the fluorescent compounds to determine the presence and/or amount of the target compounds.

The present invention also provides kits comprising a compound of Formula (I) and/or Formula (II) as described herein. The kits may also include at least one reagent and/or instructions for their use.

The methods, compositions and kits herein described can be used in connection with medical and veterinary applications, as well as fundamental scientific research and methodologies, as would be identifiable by a skilled person upon reading the present disclosure. These and other features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying figures in which.

DETAILED DISCLOSURE OF THE INVENTION

Figure 1:
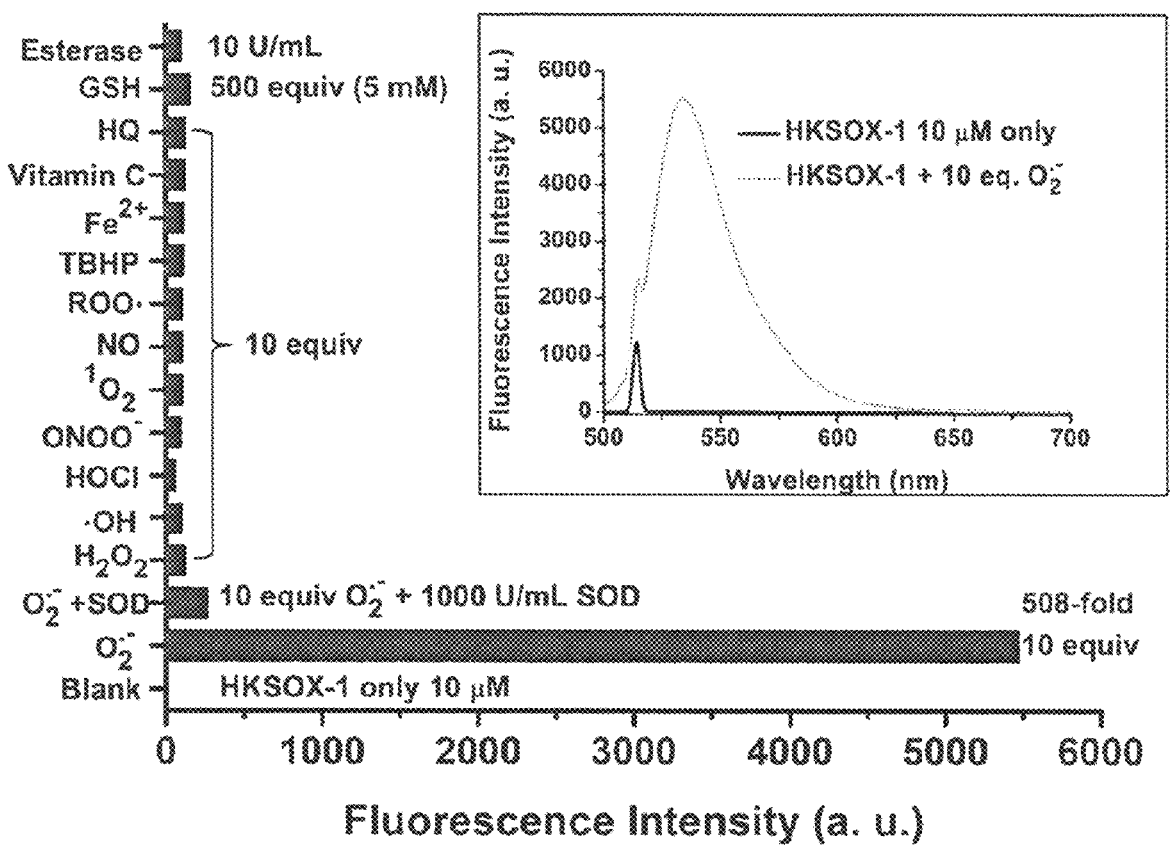
FIG. 1 shows fluorescence intensity of HKSOX-1 probe alone or in combination with $O_2^-$, other oxidants ($H_2O_2$, NO, $^1O_2$, ROO., TBHP, .OH, ONOO$^-$, HOCl), reductants ($Fe^{2+}$, ascorbic acid, 1,4-hydroquinone), esterase or GSH.

The present invention is directed to novel bistriflate-based compounds and their use as fluorogenic probes for measurement, detection and imaging of superoxide anion radicals in cellular models, including inflammation and mitochondrial inhibition. The fluorogenic probes provided herein feature a novel mechanism for $O_2^-$ detection, as they contain triflate groups as reacting sites, thus avoiding interference from cellular reducing species such as cysteine, glutathione (GSH) and $Fe^{2+}$. The fluorogenic probes of the present invention provide selectivity for superoxide over a wide range of oxidants and reductants in the mitochondria of living cells.

Compounds useful in aspects of the present invention are represented by Formula (I) and (II):

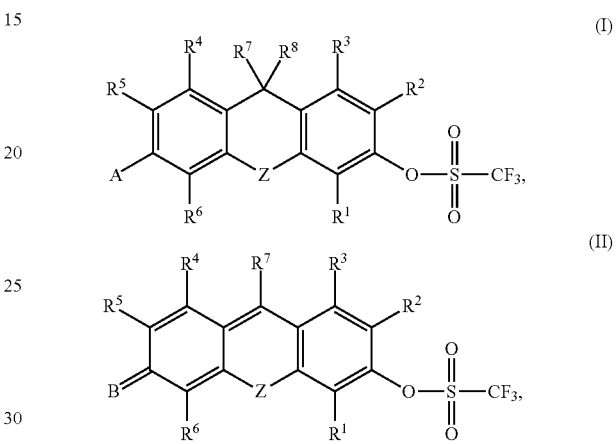

including tautomers thereof.

In some embodiments of compounds of Formula (I) and Formula (II):
each of $R^1$ and $R^2$ is independently F, Cl or H;
each of $R^3$, $R^4$, $R^5$ and $R^6$ independently H, F, Cl, Br, I, CN, alkyl, halogenated alkyl, heteroalkyl, alkenyl, alkynyl, aralkyl, aryl, alkaryl, heterocyclyl, cycloalkyl, cycloalkenyl, cycloalkynyl, hydroxyalkyl, aminoalkyl, amino, alkylamino, arylamino, dialkylamino, alkylarylamino, diarylamino, acylamino, hydroxy, thiol, thioalkyl, alkoxy, alkylthio, alkoxyalkyl, aryloxy, arylalkoxy, acyloxy, nitro, carbamoyl, trifluoromethyl, phenoxy, benzyloxy, phosphoric acid, phosphate ester, sulfonic acid (—$SO_3H$), sulfonamide, —C(=O)—$P^1$ or —C(=O)-M-$P^2$; wherein each of $P^1$ and $P^2$ is independently hydrogen, halo, alkoxy, hydroxy, thiol, alkyl, alkenyl, alkynyl, cycloalkyl, cycloalkenyl, cycloalkynyl, aryl, alkaryl, arylalkyl, carbamate, amino, alkylamino, arylamino, dialkylamino, alkylarylamino, diarylamino, alkylthio, heteroalkyl, alkyltriphenylphosphonium, or heterocyclyl having from 3 to 7 ring atoms; M is alkylene, alkenylene, alkynylene, arylene, aralkylene or alkarylene;

A is $OR^9$ or $NR^{10}R^{11}$; wherein $R^9$ is H, allyl, alkenyl, alkynyl, alkoxyalkyl, heteroalkyl, cycloalkyl, cycloalkenyl, cycloalkynyl, heterocyclyl, aminoalkyl, aryl, alkaryl, arylalkyl, carboxyalkyl, alkoxycarbonyl, acyl or aminocarbonyl; wherein each of $R^{10}$ and $R^{11}$ is independently H, alkyl, halogenated alkyl, alkenyl, alkynyl, alkoxyalkyl, heteroalkyl, cycloalkyl, cycloalkenyl, cycloalkynyl, heterocyclyl, aminoalkyl, arylalkyl, alkyloxy, acyl, carboxyalkyl, sulfoalkyl, a salt of carboxyalkyl, a salt of sulfoalkyl, or an ester or amide of carboxyalkyl or sulfoalkyl; or $R^{10}$ in combination with $R^{11}$ forms a saturated 5- or 6-membered heterocycle that is a piperidine, a morpholine, a pyrrolidine or a piperazine, each of which is optionally substituted by alkyl, carboxylic acid, a salt of carboxylic acid, or a carboxylic acid ester of an alcohol; or $R^{10}$ in combination with $R^5$, or $R^{11}$ in combination with $R^6$, or both, form a 5- or 6-membered ring that is saturated or unsaturated, or further fused with an aryl or heteroaryl ring, and is optionally substituted by one or more alkyls, carboxylic acids, sulfonic acids (—SO$_3$H), or their salts, ester or amide derivatives;

B is O or N$^+$R$^{10}$R$^{11}$;

Z is O, S, NR$^{12}$, CR$^{12}$R$^{13}$, SiR$^{12}$R$^{13}$, GeR$^{12}$R$^{13}$, or SnR$^{12}$R$^{13}$; wherein each of $R^{12}$ and $R^{13}$ is independently H, alkyl, halogenated alkyl, heteroalkyl, alkenyl, alkynyl, aralkyl, aryl, alkaryl, heterocyclyl, cycloalkyl, cycloalkenyl, cycloalkynyl, hydroxyalkyl, aminoalkyl, hydroxy, thiol, thioalkyl, alkoxy, alkylthio, alkoxyalkyl, aryloxy, arylalkoxy, acyloxy, carbamoyl, trifluoromethyl, phenoxy, benzyloxy, phosphonic acid, phosphate ester, sulfonic acid (—SO$_3$H), sulfonamide, carboxylic acid, carboxylic ester, or carboxylic amide; or $R^{12}$ in combination with $R^{13}$ forms a saturated 5- or 6-membered heterocycle that is optionally substituted by alkyl, carboxylic acid, a salt of carboxylic acid, or a carboxylic acid ester of an alcohol; or $R^{12}$ and $R^{13}$ are independently CH$_3$, or phenyl;

$R^7$ is H, CF$_3$, CN, a carboxylic acid, a salt of carboxylic acid, or a carboxylic acid ester of an alcohol; or $R^7$ is a saturated or unsaturated alkyl that is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—SO$_3$H), sulfonamide (—SO$_2$NR$^{14}$R$^{15}$), wherein each of $R^{14}$ and $R^{15}$ represents a saturated or unsaturated, cyclic or acyclic alkyl that is optionally substituted by one or more F, Cl, Br, I, a carboxylic acid, a salt of carboxylic acid, a carboxylic acid ester of an alcohol, amino, alkylamino, dialkylamino, alkoxy, or alkyltriphenylphosphonium; or $R^7$ has Formula (III):

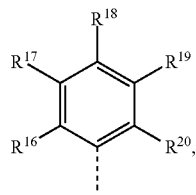

(III)

wherein each of $R^{16}$, $R^{17}$, $R^{18}$, $R^{19}$ and $R^{20}$ is independently H, F, Cl, Br, I, CN, nitro, a carboxylic acid, a salt of carboxylic add, sulfonic acid (—SO$_3$H), sulfonamide (—SO$_2$NR$^{14}$R$^{15}$), hydroxy, azide, alkyl, alkenyl, alkynyl, heteroalkyl, cycloalkyl, cycloalkenyl, cycloalkynyl, aryl, alkylaryl, arylalkyl, heterocyclyl, alkoxy, alkoxyalkyl, alkoxyalkoxy, acyl, alkylcarbonylalkyl, halogenated alkyl, aminoalkyl, carboxyalkyl, thiol, alkylthio, amino, alkylamino, dialkylamino, alkoxycarbonyl, alkoxycarbonylalkyl, aminocarbonyl, alkylaminocarbonyl, dialkylaminocarbonyl, or arylcarboxamido, the alkyl or aryl of which is optionally substituted by one or more F, Cl, Br, I, a carboxylic acid, a salt of carboxylic acid, a carboxylic acid ester of an alcohol, amino, alkylamino, dialkylamino, alkoxy, alkyltriphenylphosphonium, sulfonic acid (—SO$_3$H), or sulfonamide (—SO$_2$NR$^{14}$R$^{15}$); or $R^{16}$ and $R^{17}$ together, $R^{17}$ and $R^{18}$ together, $R^{18}$ and $R^{19}$ together, or $R^{19}$ and $R^{20}$ together form a part of a 5- or 6-membered cycloalkyl, heterocyclyl, aryl or heteroaryl ring fused with the phenyl ring of Formula (III) that is optionally further substituted by one or more F, Cl, Br, I, a carboxylic acid, a salt of carboxylic acid, a carboxylic acid ester of an alcohol, amino, alkylamino, dialkylamino, alkoxy, thiol, alkylthio, alkyltriphenylphosphonium sulfonic acid (—SO$_3$H), or sulfonamide (—SO$_2$NR$^{14}$R$^{15}$); and $R^8$ is H, hydroxy, CN or alkoxy; or $R^7$ in combination with $R^8$ forms a 5-membered spirolactone or spirolactam ring or a 5-membered spirosultam ring; or $R^8$ in combination with $R^{16}$ or $R^{20}$ forms a 5- or 6-membered spirolactone or spirolactam ring or a 5- or 6-membered spirosultone or spirosultam ring that is optionally and independently substituted by H, F or CH$_3$.

In some embodiments, $R^8$ in combination with $R^7$ forms a 5-membered spirolactone or spirolactam ring or a 5-membered spirosultam ring, and $R^8$ is oxygen or substituted nitrogen.

In a preferred embodiment, compounds of the present invention have as structure of Formula (II), or a tautomer thereof, B is O, Z is O, and $R^7$ is Formula (III), wherein at least one of $R^{16}$, $R^{17}$, $R^{18}$, and $R^{19}$ is a carboxyl group and $R^{20}$ is H, CH3, OCH3, or COOH.

In some embodiments, the $R^7$ group of Formula (III) comprises one or more carboxyl groups, wherein at least one carboxyl group is further conjugated with an iminodialkylcarboxylate having a structure of (HN((CH$_2$)$_n$COOH)$_2$, wherein n is an integer from 1 to 20.

In some embodiments, compounds of the present invention have a structure of Formula (IV) or its tautomer, Formula (V):

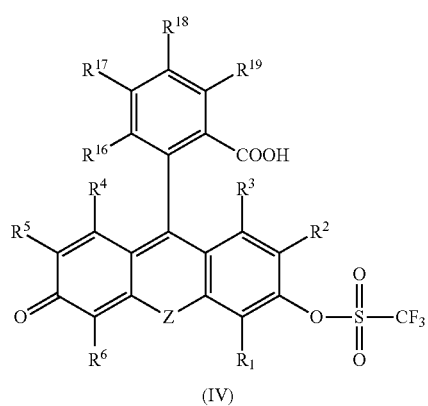

(IV)

tautomerization

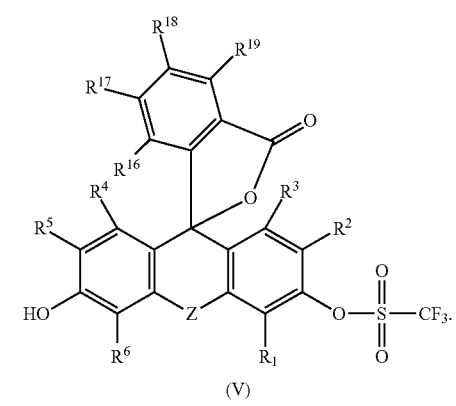

(V)

In some embodiments, compounds of the present invention comprise one of formulae 1-20:
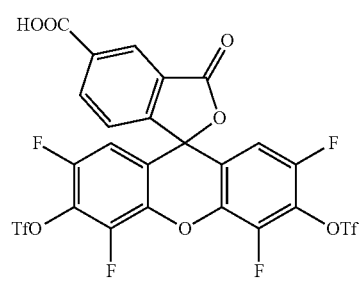
1
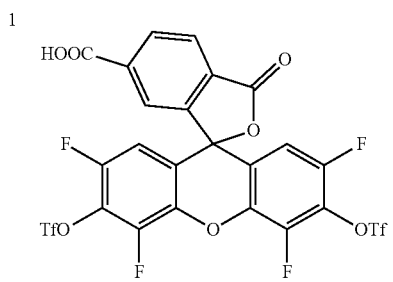
2
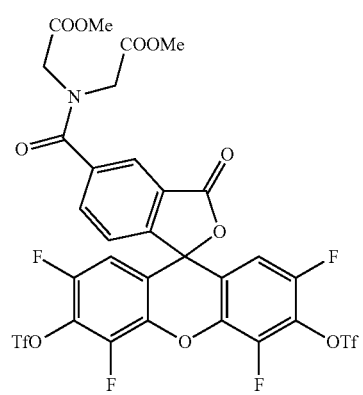
3
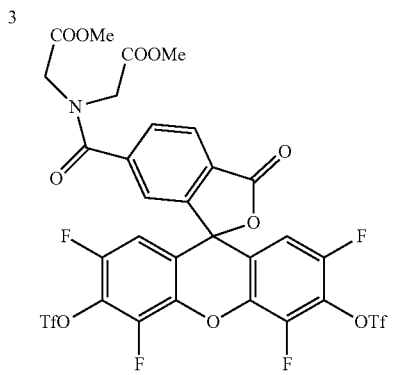
4
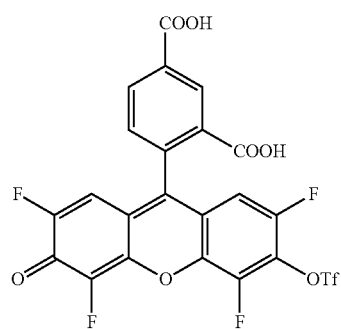
5
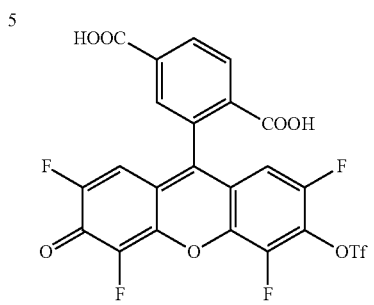
6
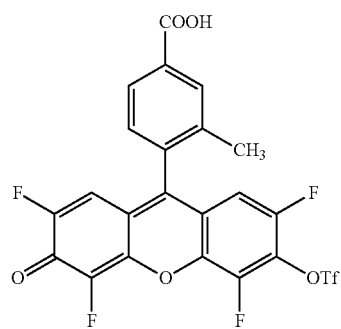
7
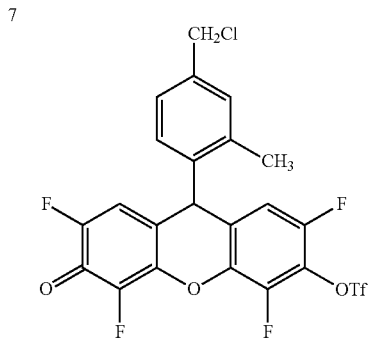
8

-continued
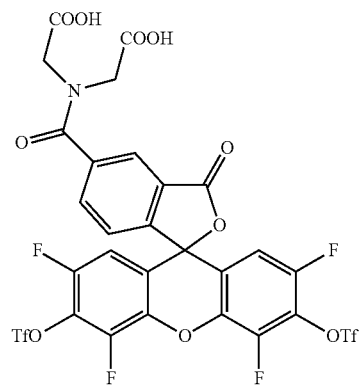
9
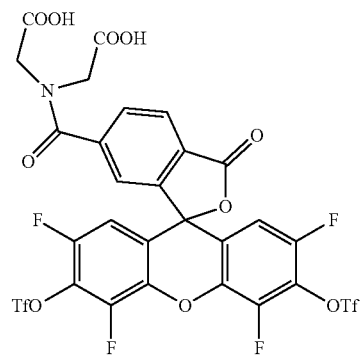
10
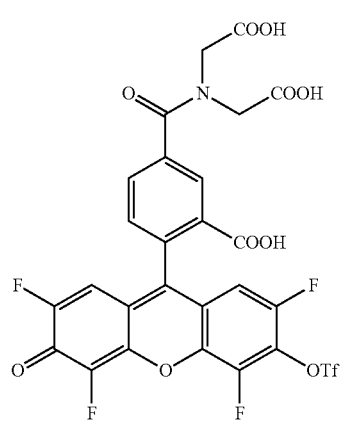
11
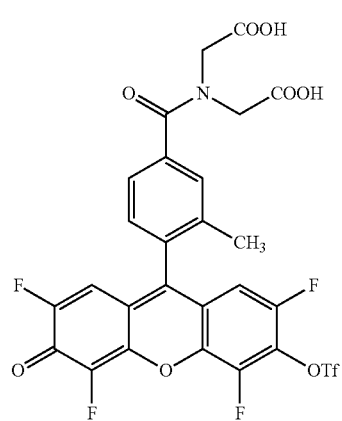
12
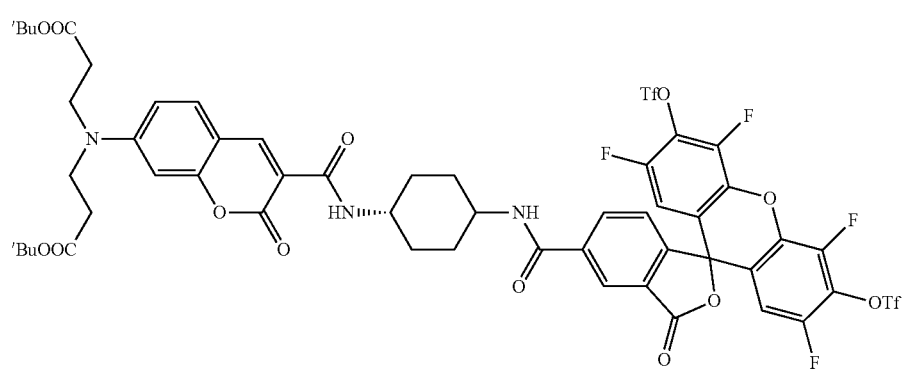
13
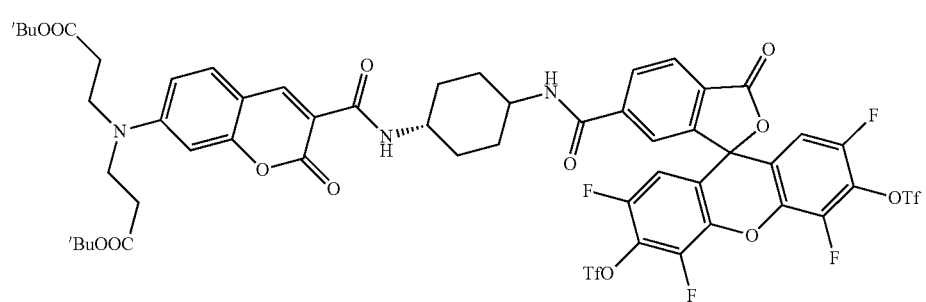
14

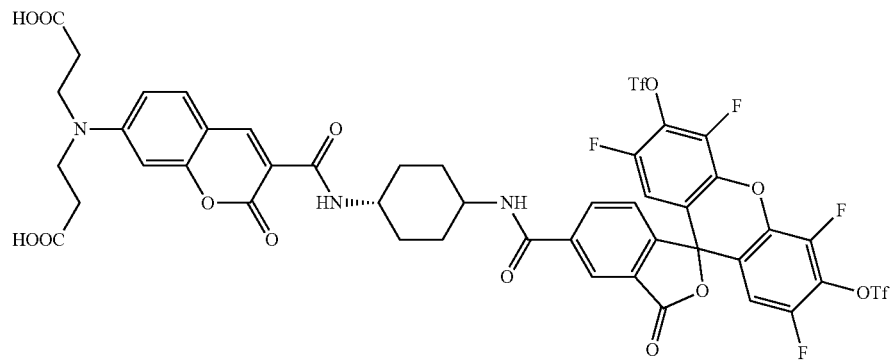
15
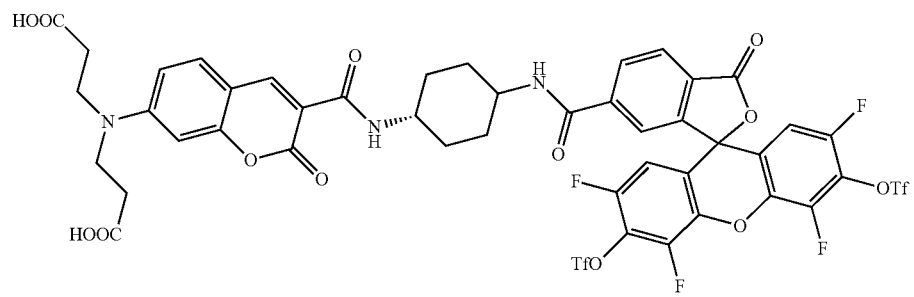
16
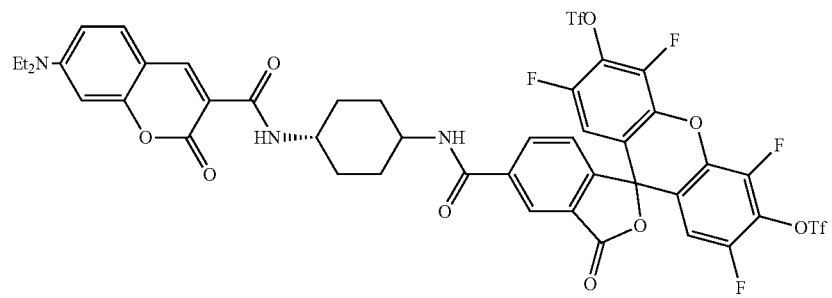
17
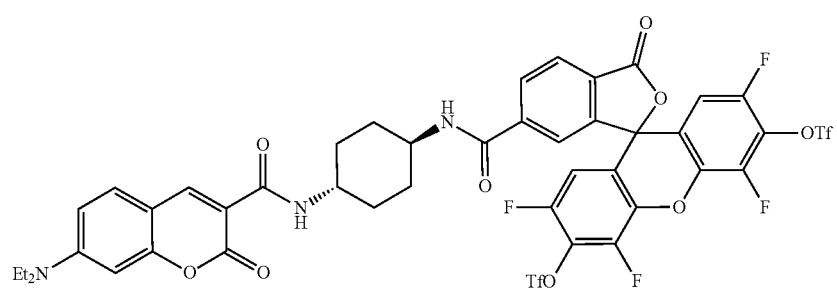
18

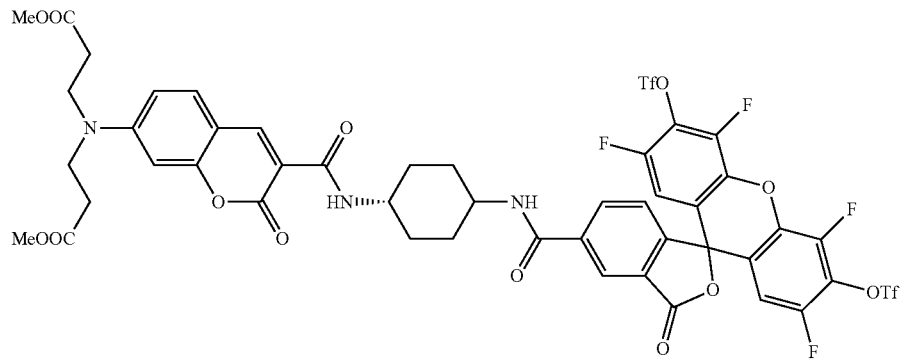
19
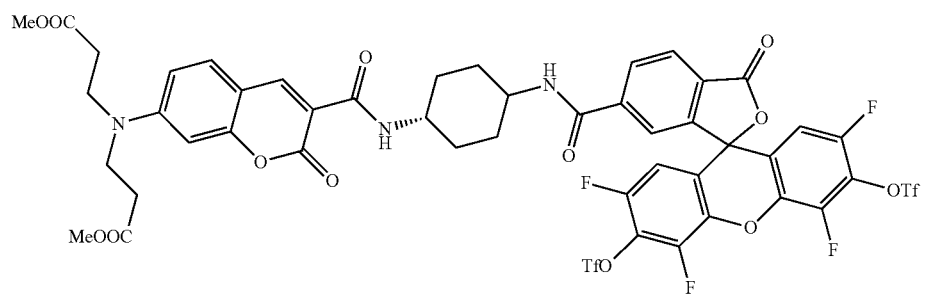
20
In another preferred embodiment, compounds of the present invention have a structure of Formula (II), or a tautomer thereof, and wherein B is N⁺R¹⁰R¹¹, Z is O, and R⁷ is Formula (III). Such compounds may have a structure of Formula (VI) or its tautomer, Formula (VII):
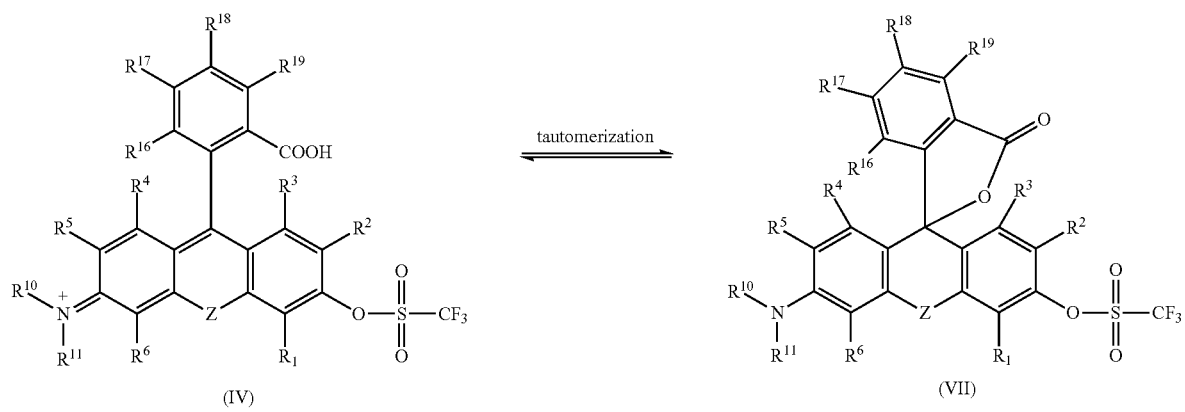

or a structure of Formula (VIII) or Formula (IX):
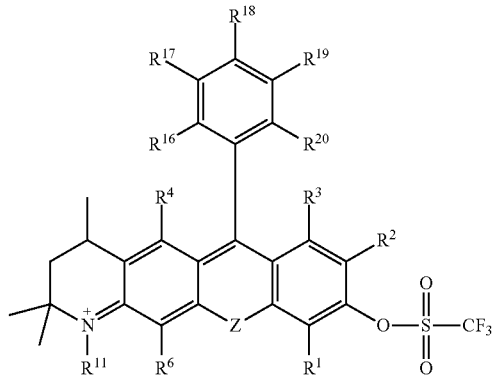
(VIII)
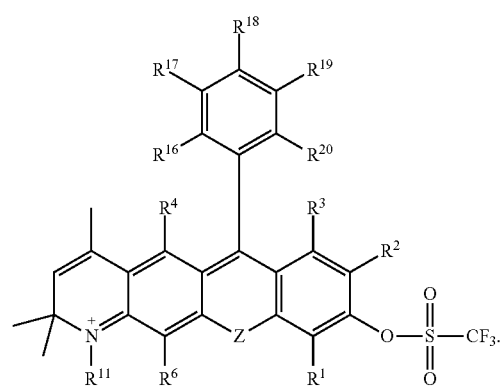
(IX)
In some embodiments, $R^{11}$ in Formula (VIII) or Formula (IX) is $(CH_2)_y T$, where T is H, COOH, $COOR^{21}$, $CONR^{22}R^{23}$, or COOAM; y is an integer from 1 to 20.
In some embodiments, compounds of the present invention comprise one of formulae 21-36:
21
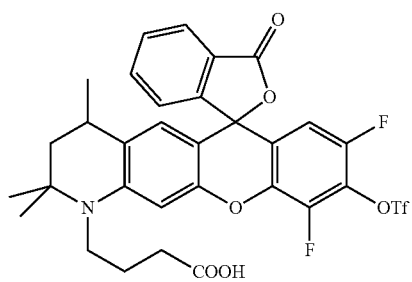
22
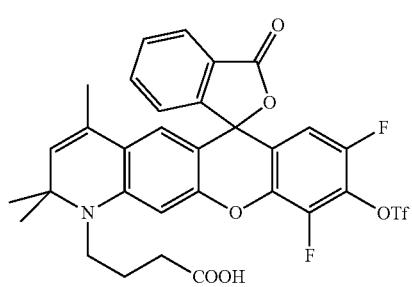
23
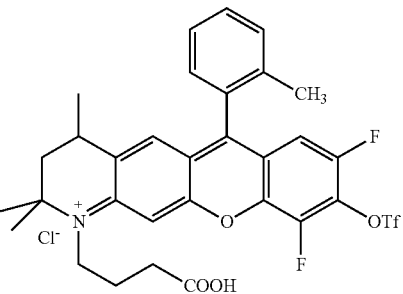
24
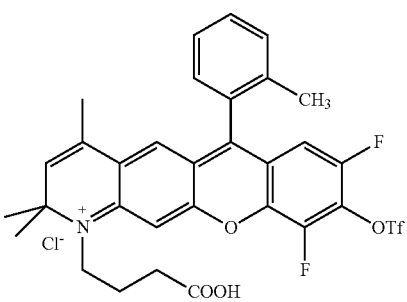
25
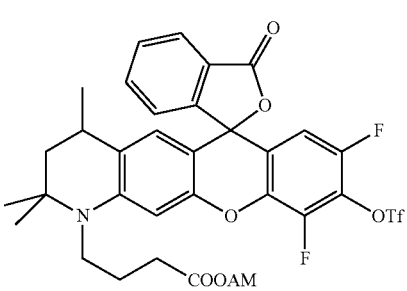
26
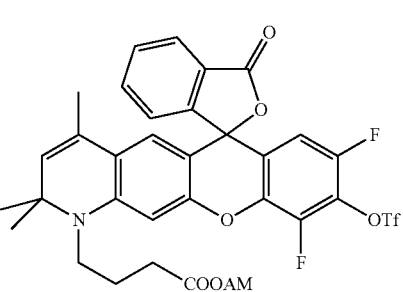
27
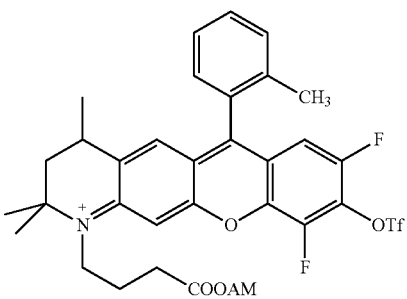

28 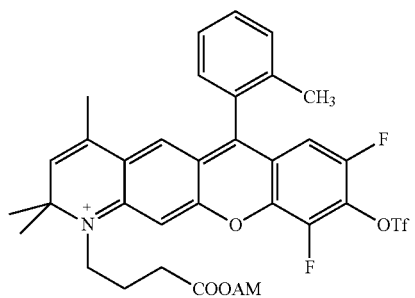
29 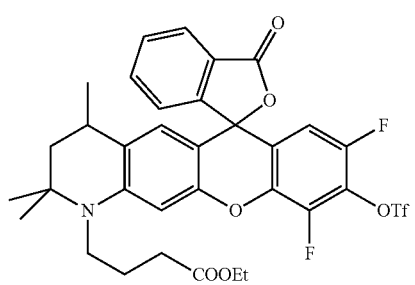
30 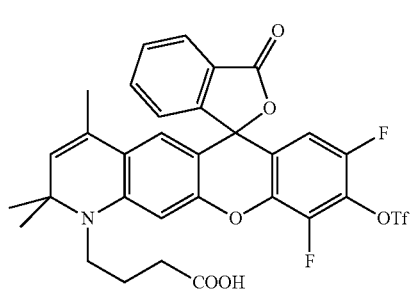
31 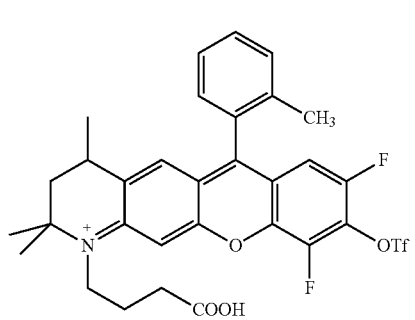
32 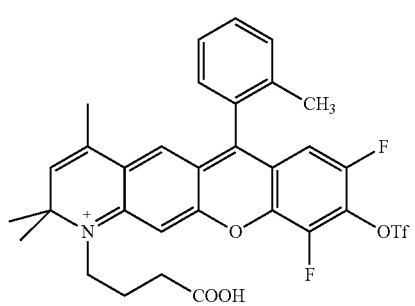
33 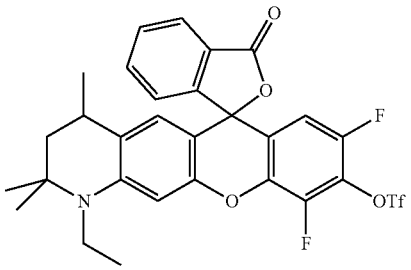
34 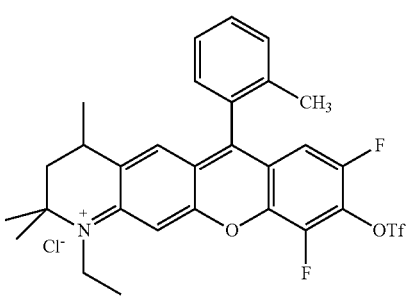
35 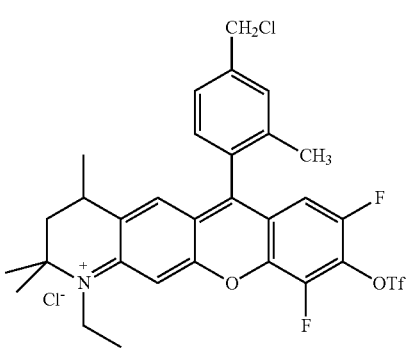
36 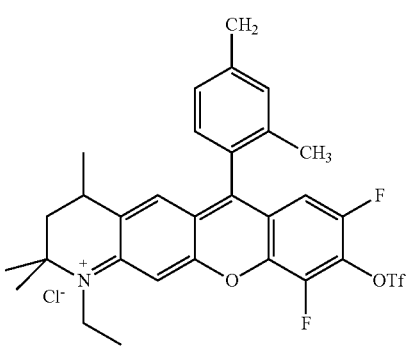
In another preferred embodiment, compounds of the present invention have a structure of Formula (II), or a tautomer thereof, and wherein B is O, Z is $YR^{12}R^{13}$ wherein Y is Si, Ge, or Sn, and $R^7$ is Formula (III). $R^{12}$ and $R^{13}$ may be independently $CH_3$, or phenyl. Furthermore, $R^{20}$ may be COOH, and the compound has a structure of Formula (X) or its tautomer Formula (XI):

21
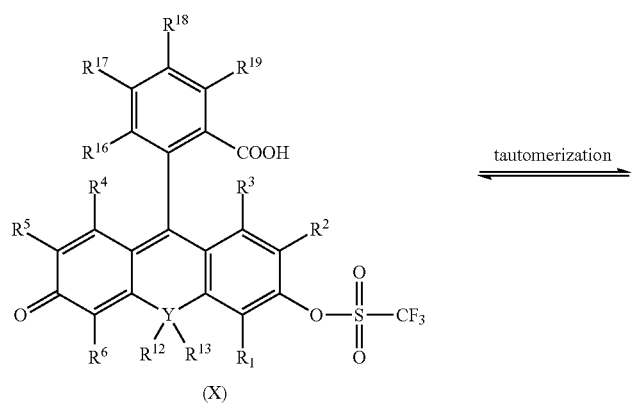
(X)
22
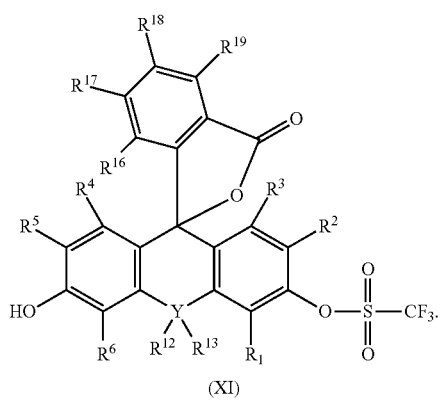
(XI)
In some embodiments, compounds of the present invention comprise one of formulae 37-48:
37
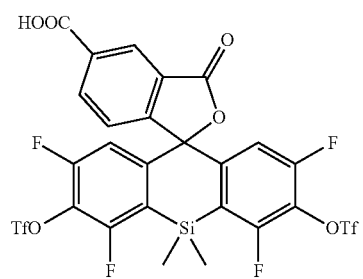
38
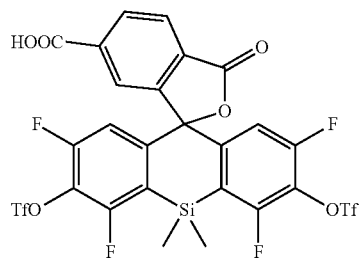
39
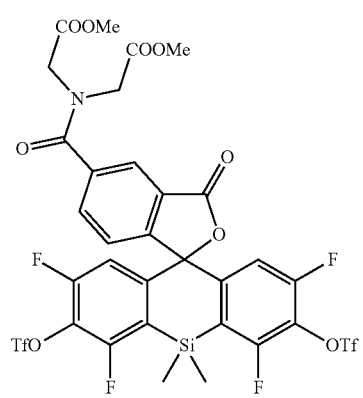
-continued
40
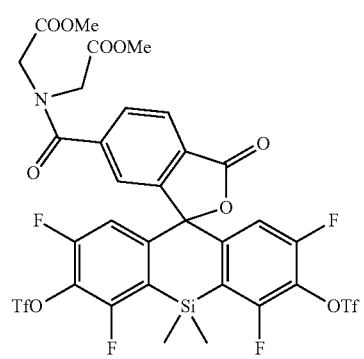
41
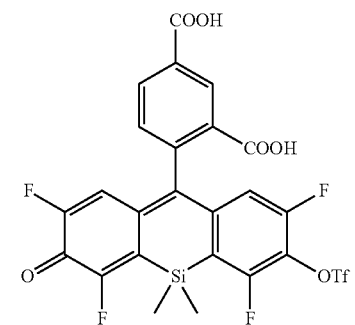
42
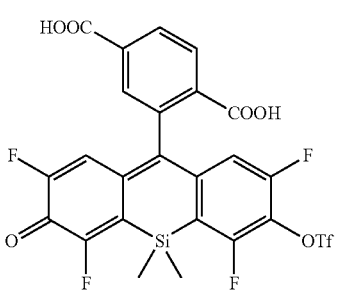

43
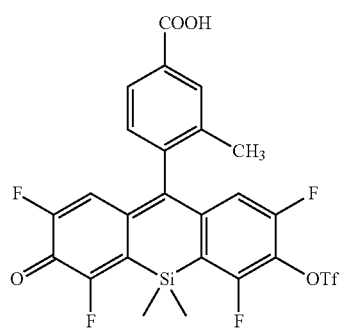
44
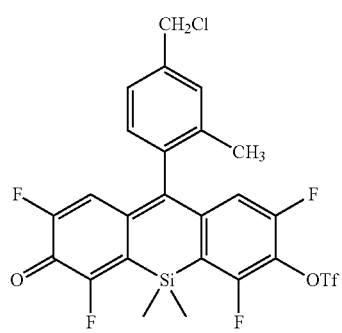
45
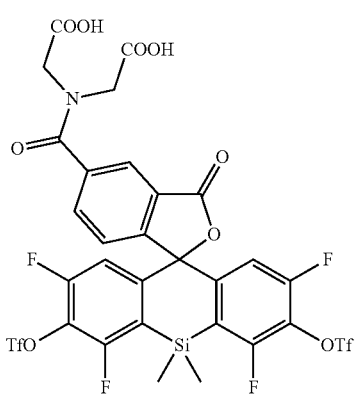
46
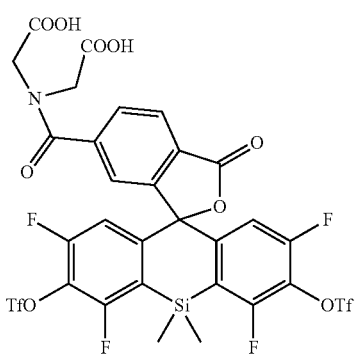
47
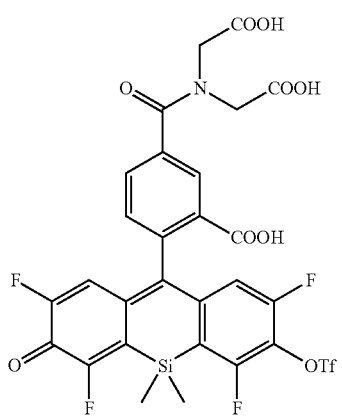
48
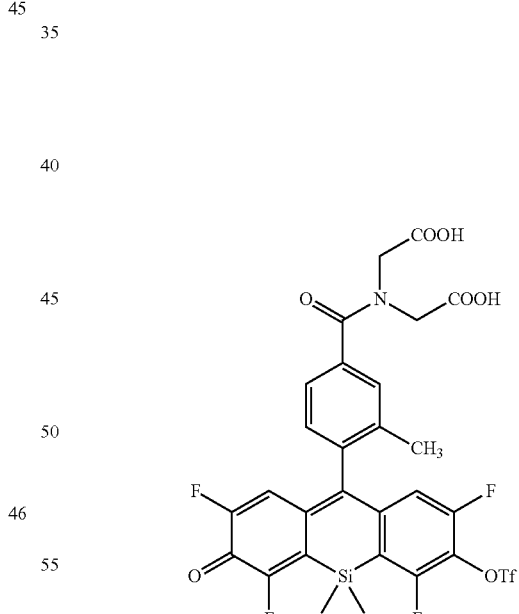
In another preferred embodiment, compounds of the present invention have a structure of Formula (II), or a tautomer thereof, wherein B is $N^+R^{10}R^{11}$, Z is $YR^{12}R^{13}$, wherein Y is Si, Ge, or Sn, and $R^7$ has Formula (III). $R^{20}$ may be COOH, and the compound has a structure of Formula (XII) or its tautomer Formula (XIII):

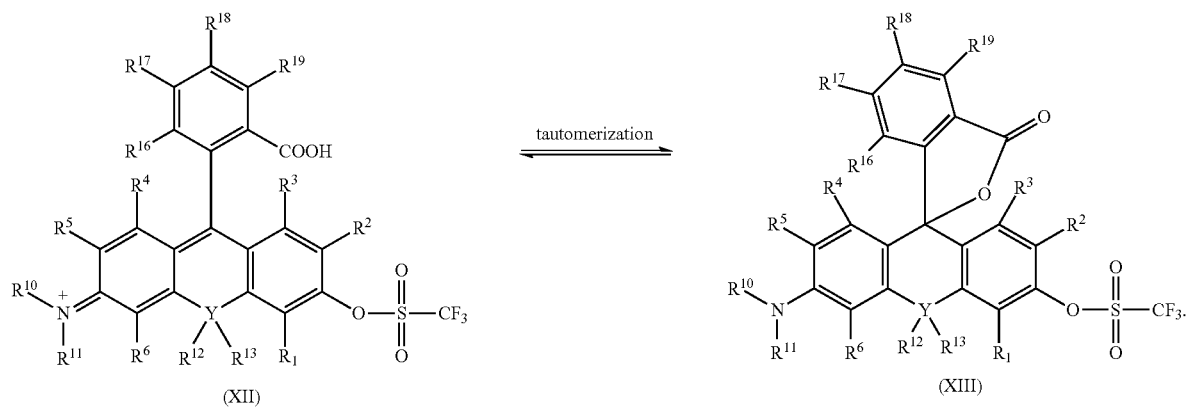

Furthermore, $R^{10}$ in combination with $R^5$, or $R^{11}$ in combination with $R^6$, or both, may form a 5- or 6-membered ring that is saturated or unsaturated, or can further be fused with an aryl or heteroaryl ring, and can optionally be substituted by one or more alkyls, carboxylic acids, sulfonic acids (—$SO_3H$), or their salts, ester or amide derivatives.

In some embodiments, compounds of the present invention have the structure of Formula (XIV) or Formula (XV):

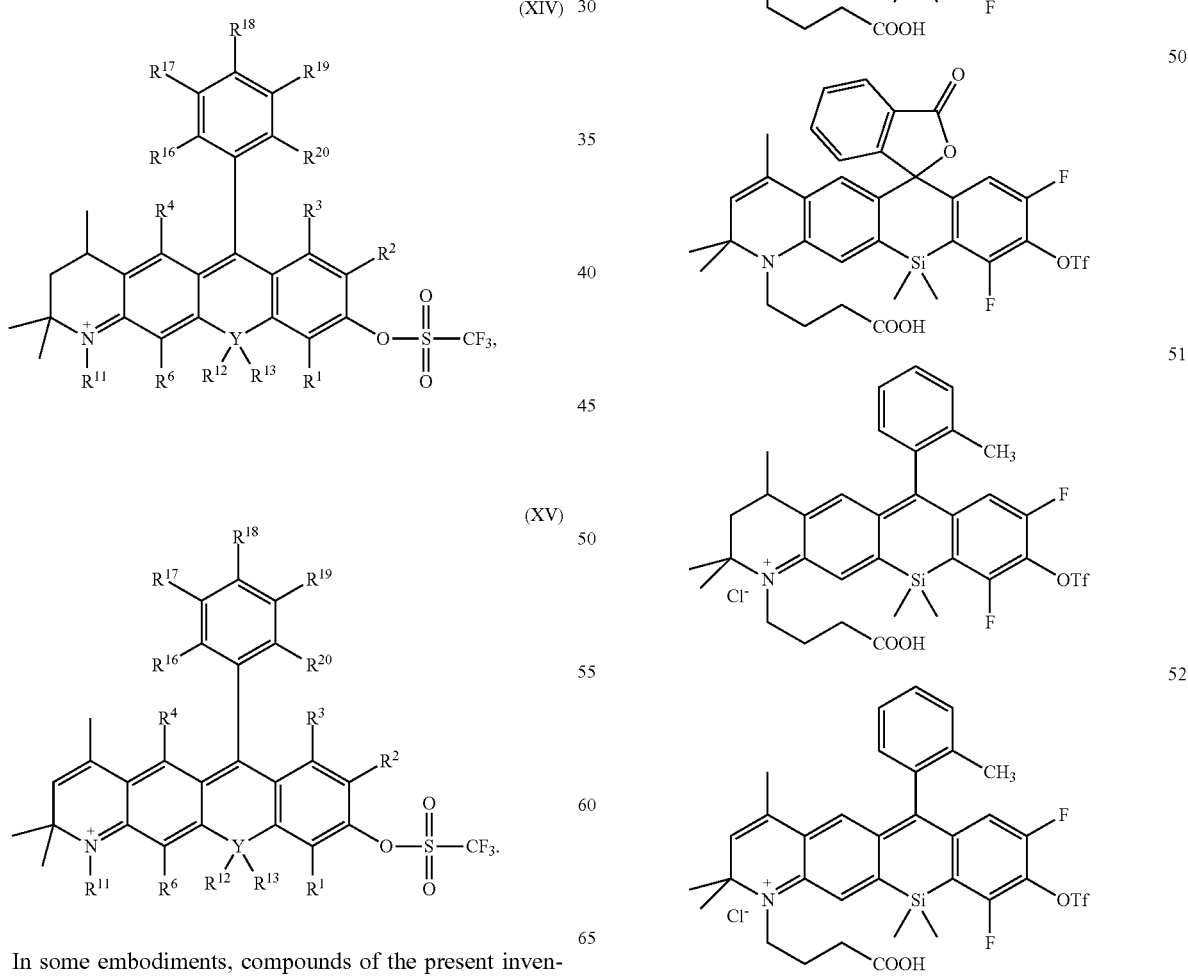

In some embodiments, compounds of the present invention comprise one of formulae 49-64:

-continued
53
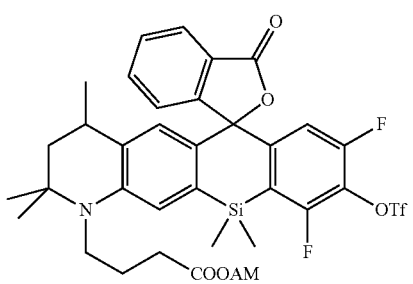
54
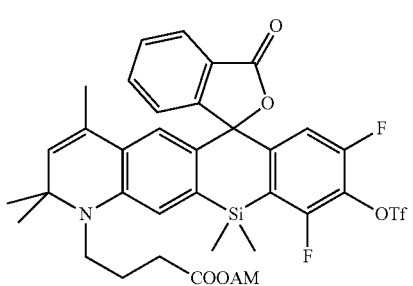
55
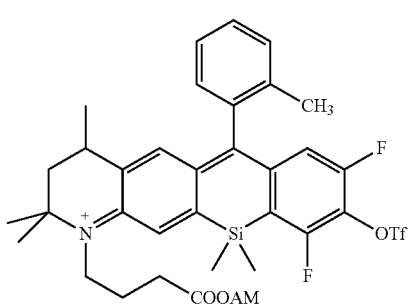
56
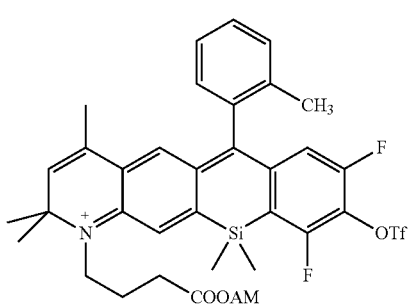
57
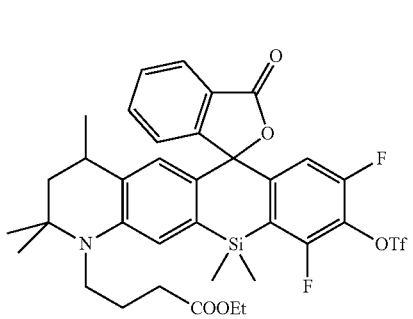
-continued
58
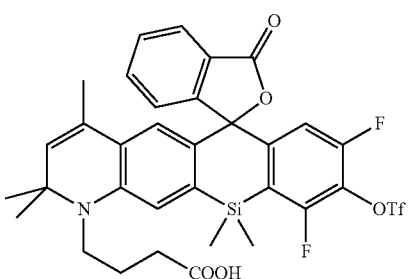
59
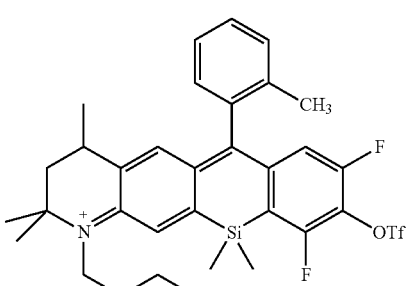
60
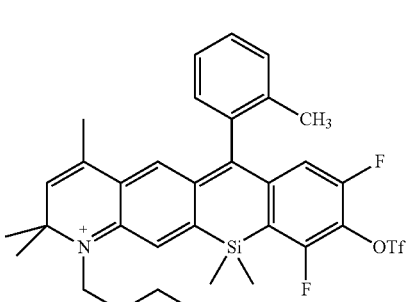
61
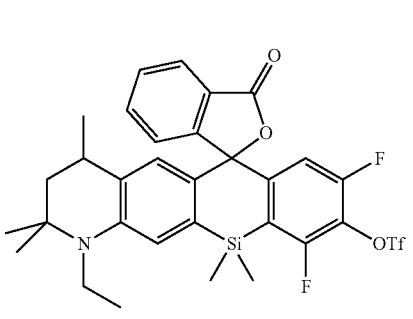
62
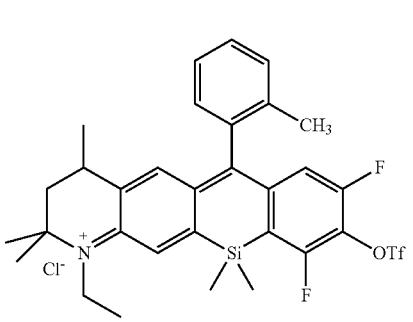

-continued

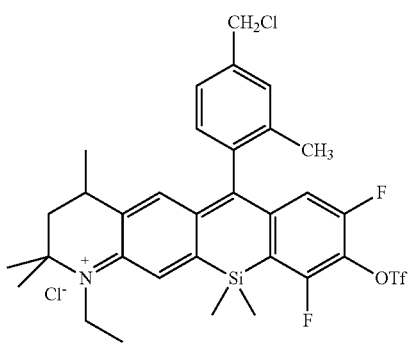
63

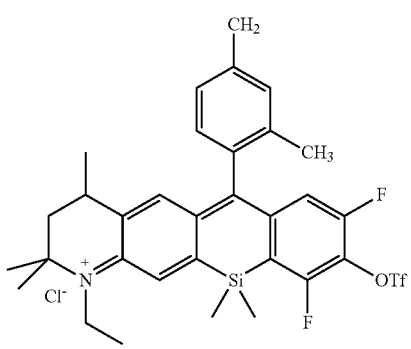
64

In some embodiments, compounds of Formula (I) or Formula (II) of the present invention comprise one or more free carboxyl groups, wherein at least one of the carboxyl groups is conjugated with a positively charged triphenylphosphonium moiety through an amide bond linkage. The linkage between the compound and the triphenylphosphonium moiety includes the following Formula (XVI) or (XVII):

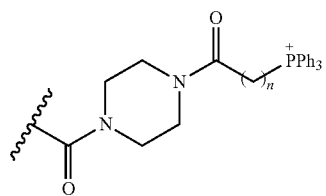
(XVI)

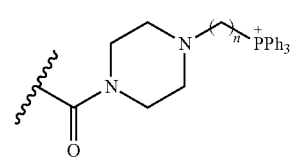
(XVII)

wherein n is an integer from 1 to 10.

In some embodiments, compounds of the present invention comprise one of formulae 65-69:

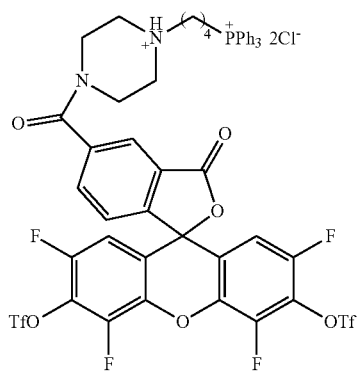
65

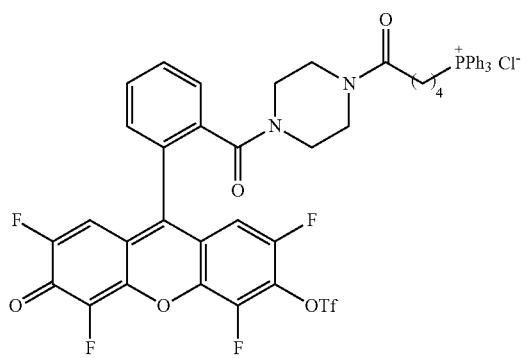
66

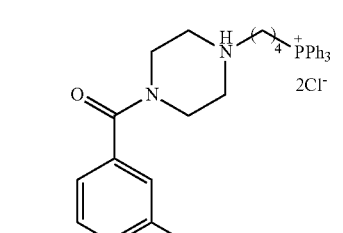
67

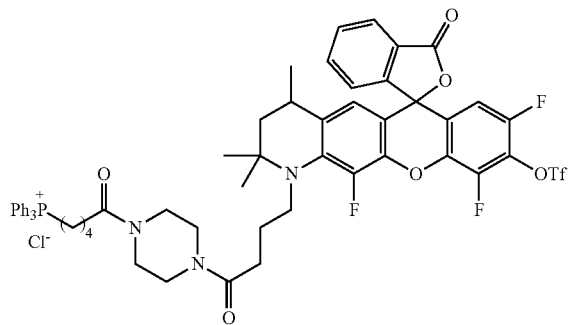
68

-continued

69

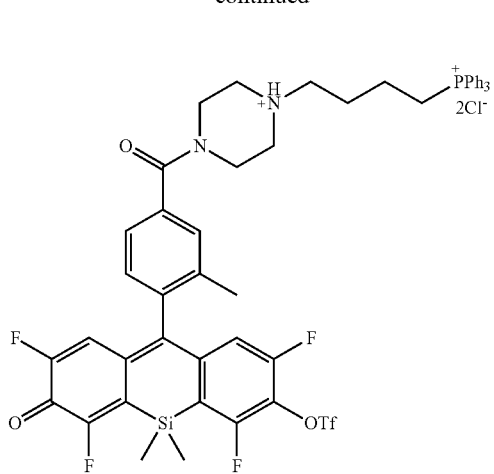

A compound comprising one or more free carboxyl groups, wherein at least one of the carboxyl group is conjugated with a positively charged mitochondria-targeted triphenylphosphonium moiety or lysosome-targeted morpholine moiety through an amide bond linkage, wherein the linkage between the compound and the morpholine moiety has the following formula (XIV):

(XIV)

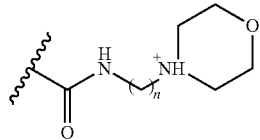

wherein n=1, 2, 3, 4, 5, 6, 7, 8, 9, or 10.

A compound having one of the formulae 70-74:

70

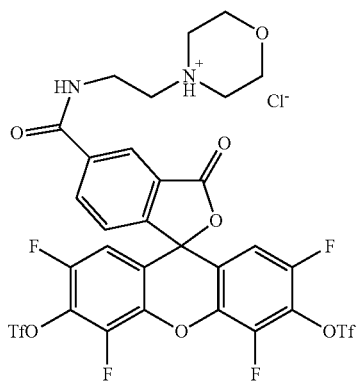

-continued

71

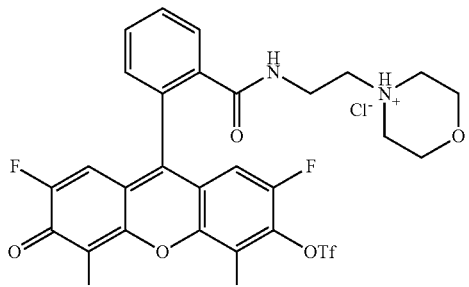

72

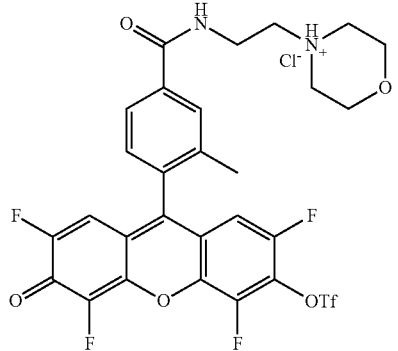

73

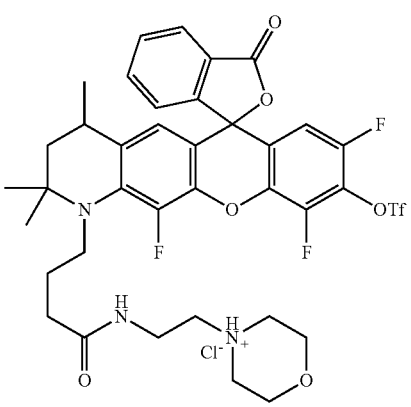

74

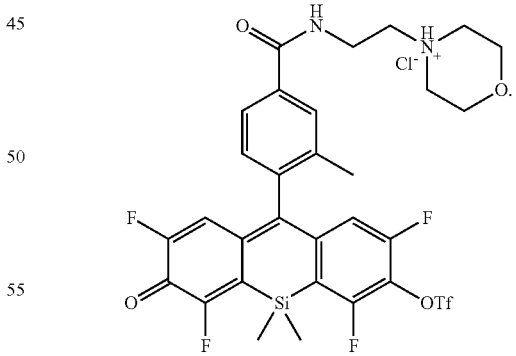

The invention further comprises a fluorogenic probe composition comprising a fluorogenic compound, and a carrier. The fluorogenic probe composition comprises a solvent, an acid, a base, a buffer solution, or a combination thereof.

The invention additionally comprises a method for detecting the presence of, and/or determining the level of superoxide in a sample, comprising contacting a compound of Formula I with the sample to form a fluorescent compound;

and determining fluorescence property of the fluorescent compound. The sample may be a chemical sample or biological sample. The biological sample may be a microorganism, or a cell or tissue.

The invention also provides a method for detecting the presence of, or determining the level of superoxide in vivo in an organism, comprising administering a compound of Formula I to the organism to form a fluorescent compound; and determining fluorescence property of the fluorescent compound.

The invention further provides a high-throughput screening method for detecting the presence of, or determining the level of, superoxide in samples, wherein the high-throughput method comprises the steps of contacting a compound of Formula I with the samples to form one or more fluorescent compounds; and determining fluorescence properties of the fluorescent compounds to determine the presence and/or amount of peroxynitrite in the samples.

The invention provides yet another embodiment a high-throughput method for screening one or more target compounds that increase or decrease the level of superoxide comprising contacting a compound of Formula I with target compounds to form one or more fluorescent compounds; and measuring fluorescence properties of the fluorescent compounds to determine the presence and/or amount of the target compounds.

In method aspects of the present invention, a high-throughput screening method for detecting the presence of, or determining the level of, superoxide in a sample, such as cells and/or tissues, is provided. The method comprises contacting a compound of Formula (I) or Formula (II) with the sample to form one or more fluorescent compounds; and determining fluorescence properties of the fluorescent compounds to determine the presence and/or amount of superoxide in the sample.

In another method aspect of the present invention, a high-throughput method for screening one or more target compounds that increase or decrease the level of superoxide is provided. The method comprises contacting a compound of Formula (I) or Formula (II) with the target compounds to form one or more fluorescent compounds; and measuring fluorescence properties of the fluorescent compounds to determine the presence and/or amount of the target compounds. Fluorescence properties may be determined by fluorescence microscopy or any other method/instrument that would be understood by those skilled in the art.

The present invention also provides kits comprising a compound of Formula (I) and/or Formula (II) as described herein. The kits may also be used in the methods described herein. The kits may also include at least one reagent and/or instructions for their use. Also, the kit may include one or more containers filled with reagents(s) and/or one or more components of the compositions of the invention. The kits may also comprise a control composition, such as a positive and/or negative control fluorescence compounds.

Without further elaboration, it is believed that one skilled in the art can, using the preceding description, utilize the present invention to its fullest extent. The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. All patents, patent applications, provisional applications, and publications referred to or cited herein are incorporated by reference in their entirety, including all figures and tables, to the extent they are not inconsistent with the explicit teachings of this specification. By citation of various references in this document, Applicants do not admit any particular reference is "prior art" to their invention.

EXAMPLES

The methods and compositions herein described and the related kits are further illustrated in the following examples, which are provided by way of illustration and are not intended to be limiting. It will be appreciated that variations in proportions and alternatives in elements of the components shown will be apparent to those skilled in the art and are within the scope of embodiments of the present invention. Theoretical aspects are presented with the understanding that Applicants do not seek to be bound by the theory presented.

Following are examples that illustrate procedures for practicing the invention. These examples should not be construed as limiting. All parts, amounts or percentages are by weight and all solvent mixture proportions are by volume unless otherwise noted.

Example 1—Synthesis of Green Fluorogenic Compounds HKSOX-1 and HKSOX-1r

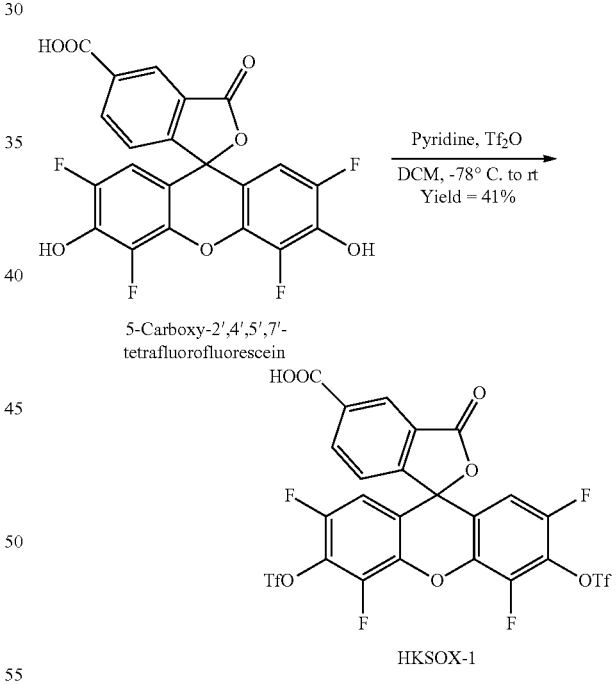

To a solution of 5-carboxy-2',4',5',7'-tetrafluorofluorescein (220 mg, 049 mmol) in anhydrous pyridine (5 mL) and dry DCM (5 mL) at −78° C. was added Tf$_2$O (246 μL, 1.47 mmol) dropwise under argon atmosphere. The resulting mixture was stirred at −78° C. for 10 min and then at room temperature for another 10 min. Then the reaction was quenched with saturated NaHCO$_3$ aqueous solution at room temperature. The mixture was diluted with ethyl acetate (50 mL) and washed with 1N HCl, water and brine. The organic layer was dried over anhydrous magnesium sulfate and concentrated in vacuo. The target compound HKSOX-1 was isolated by flash chromatography on silica gel, using MeOH:DCM (1:9) as the eluent. Yield 143 mg (41%). $^1$H NMR (400 MHz, CDCl$_3$) δ 8.67 (s, 1H), 8.43 (d, J=8.0 Hz, 1H), 7.52 (d, J=8.0 Hz, 1H), 7.06 (s, 1H), 7.03 (s, 1H); $^{13}$C NMR (150 MHz, CDCl$_3$) δ 168.68, 167.74, 155.80, 152.89, 151.22, 146.50, 144.77, 138.45, 133.23, 138.21, 138.16, 138.15, 135.96, 128.87, 128.78, 128.75, 128.66, 128.56, 127.22, 125.56, 123.28, 121.77, 121.72, 121.17, 119.05, 116.93, 111.44, 111.41, 111.29, 111.27, 80.02; $^{19}$F NMR (376 MHz, CDCl$_3$) δ −74.80, −129.97, −142.98, −142.99; LRMS (EI) m/z (%) 711.9 (M$^+$; 7.21), 149.0 (100); HRMS (EI): calcd for C$_{23}$H$_6$O$_{11}$F$_{10}$S$_2$: 711.9192, Found: 711.9200.

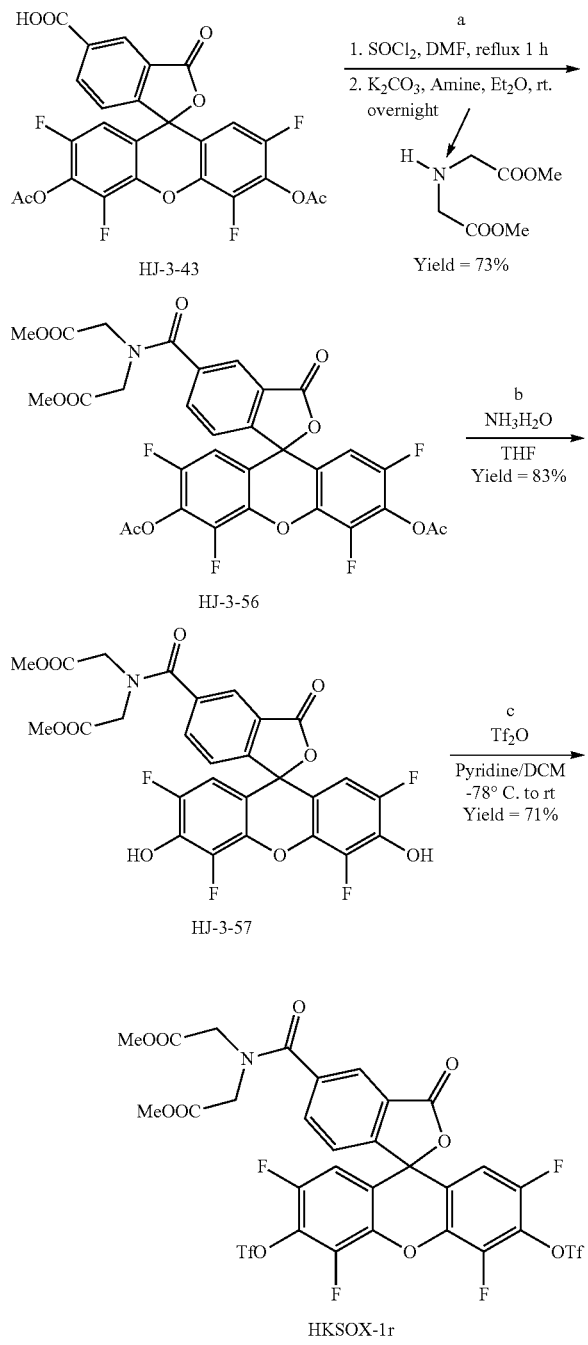

a) To a solution of HJ-3-43 (107 mg, 0.2 mmol) in anhydrous SOCl$_2$ (5 mL) at room temperature was added one drop of DMF under argon atmosphere. The resulting mixture was stirred under reflux for 1 h and then allowed to cool down to room temperature. Then the crude acid chloride was dissolved in dry THF (10 mL), and added with K$_2$CO$_3$ (69 mg, 0.5 mmol) and amine (48 mg, 0.3 mmol) under argon atmosphere. The resulting mixture was stirred overnight at room temperature. The mixture was diluted with ethyl acetate (50 mL) and washed with water and brine. The organic layer was dried over anhydrous magnesium sulfate and concentrated in vacuo. The target compound HJ-3-56 was isolated by flash chromatography on silica gel, using EtOAc:Hexane (1:4) as the eluent. Yield 99 mg (73%). $^1$H NMR (400 MHz, CDCl$_3$) δ 8.14 (s, 1H), 7.85 (d, J=7.9 Hz, 1H), 7.28 (d, J=7.8 Hz, 1H), 6.50 (d, J=1.4 Hz, 1H), 6.48 (d, J=1.3 Hz, 1H), 4.35 (s, 2H), 4.17 (s, 2H), 3.80 (s, 3H), 3.78 (s, 3H), 2.41 (s, 6H); $^{13}$C NMR (100 MHz, CDCl$_3$) δ 169.90, 169.10, 168.95, 166.96, 166.74, 152.81, 152.36, 149.88, 145.65, 143.04, 137.78, 136.66, 134.66, 129.54, 129.36, 125.51, 124.65, 124.40, 116.66, 116.60, 108.41, 108.38, 108.20, 79.58, 52.83, 52.46, 51.63, 47.62, 20.00; $^{19}$F NMR (376 MHz, CDCl$_3$) δ −128.51, −128.54, −141.86; LRMS (EI) m/z (%) 675.1 (M$^+$; 3.93), 358.0 (100); HRMS (EI): calcd for C$_{31}$H$_{21}$O$_{12}$N$_1$F$_4$; 675.1000, Found: 675.0994.

b) To a solution of HJ-3-56 (58 mg, 0.086 mmol) THF (5 mL) at room temperature was added NH$_3$.H$_2$O (0.08 mL, 0.515 mmol). The resulting mixture was stirred at room temperature for 2 h. Then the mixture was diluted with ethyl acetate (25 mL) and washed with 1N HCl, water and brine. The organic layer was dried over anhydrous magnesium sulfate and concentrated in vacuo. The target compound HJ-3-57 was purified by flash chromatography on silica gel, using MeOH:DCM (1:9) as the eluent. Yield 42 mg (83%). $^1$H NMR (400 MHz, CDCl$_3$) δ 8.13 (s, 1H), 7.86 (d, J=7.8 Hz, 1H), 7.32 (d, J=7.8 Hz, 1H), 6.33 (s, 1H), 6.30 (s, 1H), 4.39 (s, 2H), 4.25 (s, 2H), 3.83 (s, 3H), 3.80 (s, 3H); $^{19}$F NMR (376 MHz, CDCl$_3$) δ −136.95, −154.41.

c) To a solution of HJ-3-57 (42 mg, 0.071 mmol) in anhydrous pyridine (5 mL) and dry DCM (5 mL) at −78° C. was added Tf$_2$O (36 μL, 0.213 mmol) dropwise under argon atmosphere. The resulting mixture was stirred at −78° C. for 10 min and then at room temperature for another 10 min. Then the reaction was quenched with saturated NaHCO$_3$ aqueous solution at room temperature. The mixture was diluted with ethyl acetate (50 mL) and washed with 1N HCl, water and brine. The organic layer was dried over anhydrous magnesium sulfate and concentrated in vacuo. The target compound HKSOX-1r was isolated by flash chromatography on silica gel, using EtOAc:Hexane (1:4) as the eluent. Yield 43 mg (71%). $^1$H NMR (600 MHz, CDCl$_3$) δ 8.18 (s, 1H), 7.90 (dd, J=7.9, 1.3 Hz, 1H), 7.29 (d, J=7.9 Hz, 1H), 6.67 (d, J=1.6 Hz, 1H), 6.66 (d, J=1.6 Hz, 1H), 4.35 (s, 2H), 4.17 (s, 2H), 3.81 (s, 3H), 3.80 (s, 3H); $^{13}$C NMR (150 MHz, CDCl$_3$) δ 169.58, 169.04, 168.90, 166.42, 152.15, 151.72, 150.03, 145.37, 143.62, 138.40, 136.44, 136.42, 136.37, 136.36, 135.28, 127.82, 127.73, 127.70, 127.62, 125.07, 124.92, 124.12, 121.69, 119.58, 119.56, 119.53, 117.43, 115.31, 109.23, 109.20, 109.08, 109.06, 78.42, 52.93, 52.54, 51.64, 47.62; $^{19}$F NMR (376 MHz, CDCl$_3$) δ −72.66 (t, J=5.6 Hz), −126.00 (m), −138.44 (m); LRMS (EI) m/z (%) 855.0 (M$^+$; 1.84), 694.9 (100); HRMS (EI): calcd for C$_{29}$H$_{15}$O$_{14}$N$_1$F$_{10}$S$_2$: 584.9774, Found: 854.9784.

Example 2—Synthesis of Yellow Fluorogenic Compound HKSOX-2

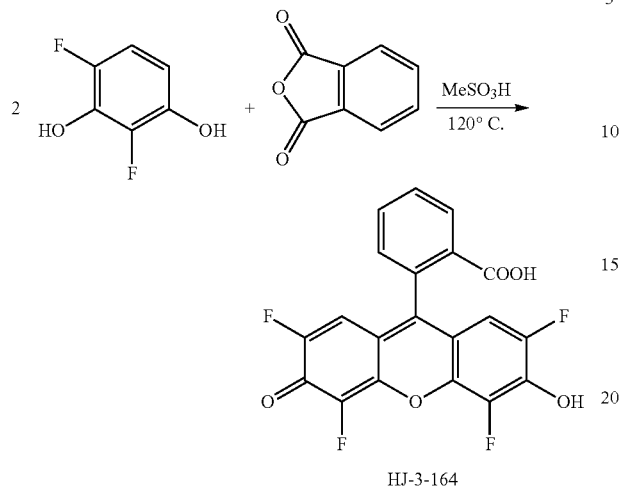

HJ-3-164

The mixture of 2,4-difluororesorcinol (925 mg, 6.33 mmol) and phthalic anhydride (469 mg, 3.17 mmol) was prepared in MeSO$_3$H (10 mL) at room temperature under argon atmosphere. The resulting mixture was stirred at 120° C. for 2 hrs. The reaction mixture was allowed to cool to room temperature and diluted with water (100 mL). The mixture was extracted with EtOAc and washed with 1N HCl water and brine. The organic layer was dried over anhydrous magnesium sulfate and concentrated in vacuo. The target compound HJ-3-164 was isolated by flash chromatography on silica gel using EtOAc:Hexane (3:7) (with 0.25% AcOH). Yield: 580 mg (45%). $^1$H NMR (400 MHz, CDCl$_3$) δ 8.06 (d, J=7.6 Hz, 1H), 7.81 (dt, J=7.5, 3.8 Hz, 1H), 7.74 (t, J=7.2 Hz, 1H), 7.28 (d, J=7.6 Hz, 1H), 6.29 (d, J=1.7 Hz, 1H), 6.26 (d, J=1.7 Hz, 1H); $^{13}$C NMR (100 MHz, CDCl$_3$) δ 173.94, 169.07, 149.80, 149.76, 147.40, 147.37, 141.99, 141.93, 139.54, 139.48, 137.26, 137.17, 135.44, 130.30, 125.92, 125.11, 123.81, 108.64, 107.50, 107.46, 107.28, 107.25; $^{19}$F NMR (376 MHz, CDCl$_3$) δ −137.58, −154.60.

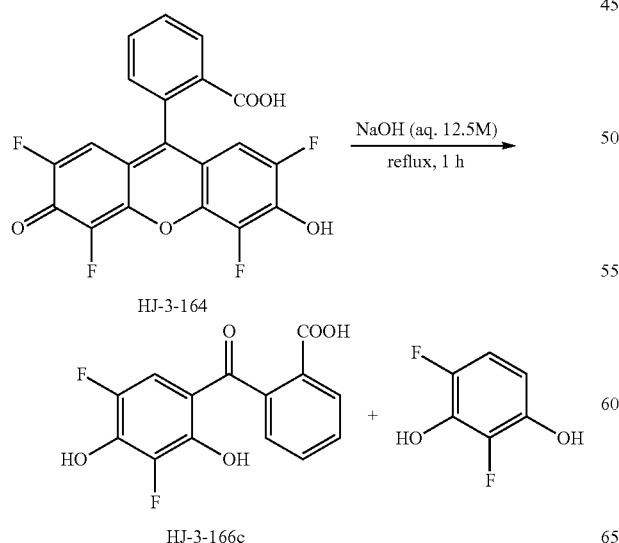

The solution of HJ-3-164 (426 mg, 1.06 mmol) in NaOH aqueous solution (12.5 M, 12 mL) was stirred under reflux for 1 hr. The reaction mixture was allowed to cool to room temperature and carefully acidified with conc. HCl until large amount of precipitate were formed. The crude target compound HJ-3-166c (312 mg, in quantitative yield) was obtained by vacuum filtration and dried in air for 24 hrs. The by-product (2,4-difluororesorcinol) can be recovered from the filtrate. $^1$H NMR (400 MHz, CDOD$_3$) δ 8.11 (dd, J=7.7, 0.9 Hz, 1H), 7.72 (td, J=7.5, 13 Hz, 1H), 7.65 (td, J=7.6, 1.3 Hz, 1H), 7.40 (dd, J=7.5, 0.9 Hz, 1H), 6.56 (dd, J=11.0, 2.1 Hz, 1H); $^{13}$C NMR (100 MHz, CDOD$_3$) δ 168.53, 147.10, 144.82, 144.71, 143.29, 143.23, 141.23, 133.68, 131.58, 131.16, 130.67, 128.42, 113.46, 113.43, 113.26, 113.23; $^{19}$F NMR (376 MHz, CDOD$_3$) δ 446.12, −146.14, −146.15, −146.17, −160.33, −160.34; LRMS (EI) m/z (%) 294.0 (M$^+$; 18), 276.0 (100); HRMS (EI): calcd for C$_{14}$H$_8$O$_5$F$_2$: 294.0340, found: 294.0332.

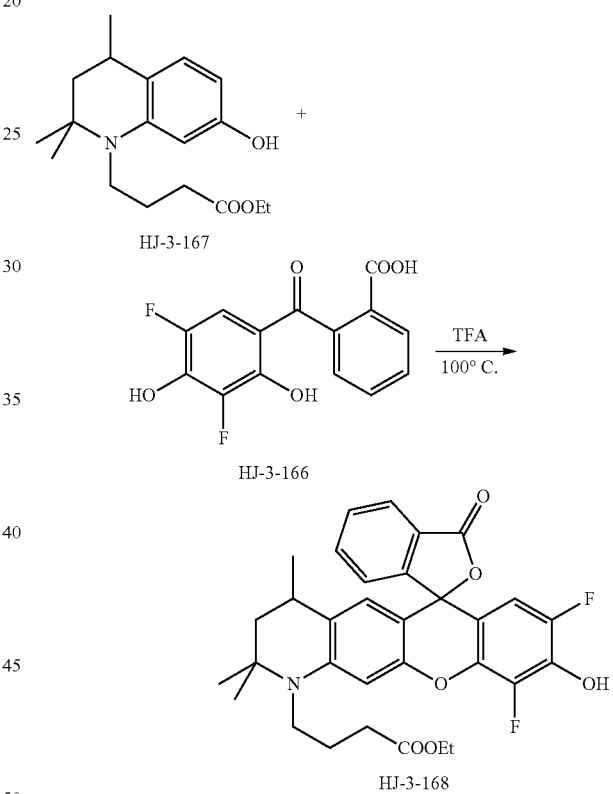

The mixture of HJ-3-167 (20 mg, 0.0655 mmol) and HJ-3-166 (19 mg, 0.0655 mmol) in TFA (2 mL) was prepared in a sealed tube at room temperature under argon atmosphere. The resulting mixture was stirred at 100° C. for 3 hrs. The reaction mixture was allowed to cool to room temperature and azeotroped with toluene for 3 times. The target compound HJ-3-168 was isolated by flash chromatography on silica gel using EtOAc:Hexane (1:1) (with 0.25% AcOH). Yield: 12 mg (33%). $^1$H NMR (500 MHz, CDCl$_3$) δ 8.23 (d, J=7.5 Hz, 1H), 7.72 (d, J=7.5 Hz, 1H), 7.68 (t, J=7.4 Hz, 1H), 6.72 (s, 1H), 6.69 (s, 1H), 6.51-6.43 (m, 1H), 4.25 (q, J=7.1 Hz, 2H), 3.59-3.49 (m, 1H), 337-3.28 (m, 1H), 2.80-2.70 (m, 1H), 2.49 (t, J=6.8 Hz, 2H), 2.08-1.93 (m, 2H), 1.79-1.72 (m, 1H), 1.57-1.48 (m, 1H), 1.41 (s, 3H), 1.35 (t, J=7.1 Hz, 3H), 1.11-1.03 (m, 3H); $^{13}$C NMR (126 MHz, CDCl$_3$) δ 173.14, 167.91, 154.34, 153.70, 152.46, 150.63, 142.60, 142.11, 140.71, 132.99, 130.34, 129.90, 128.74, 128.60, 127.95, 124.94, 124.69, 110.09, 109.68, 107.99, 107.93, 107.82, 107.75, 97.23, 61.02, 56.42, 53.51, 45.67, 45.60, 45.06, 45.02, 31.60, 29.75, 29.41, 29.35, 26.85, 26.79, 25.93, 25.83, 23.22, 23.17, 19.39, 19.32, 14.30; $^{19}F$ NMR (376 MHz, CDCl$_3$) δ −130.41, −160.64, LRMS (EI) m/z (%) 563.2 (M$^r$; 2), 71.0 (100); HRMS (EI): calcd for C$_{32}$H$_{31}$O$_6$NF$_2$ (M$^+$): 563.2119, Found: 563.2104.

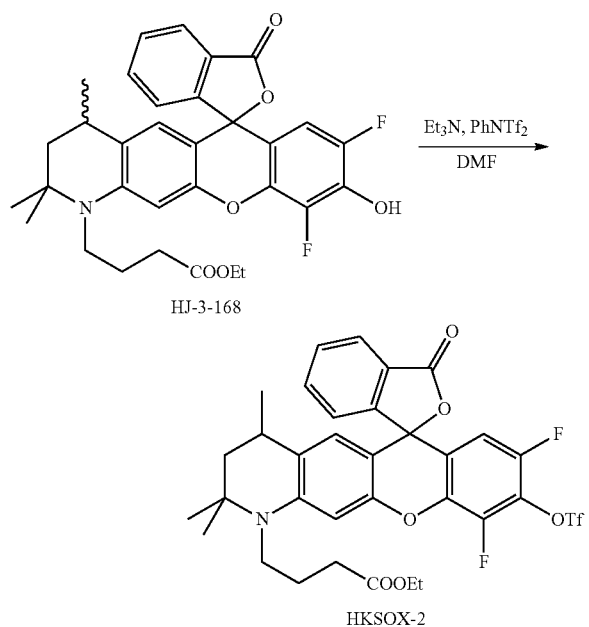

To a solution of HJ-3-168 (9.9 mg, 0.0176 mmol) in anhydrous DMF (21 mL) at room temperature was added Et$_3$N (7 μL, 0.0528 mmol) slowly under argon atmosphere. After stirring for 15 min, PhNTf$_2$ was added and the resulting mixture was stirred for another 30 min. Then the mixture was diluted with ethyl acetate (10 mL) and washed with 1N HCl, water and brine. The organic layer was dried over anhydrous magnesium sulfate and concentrated in vacuo. The target compound HJ-3-149 was isolated by flash column chromatography on silica gel, using EtOAc:Hexane (1:9) as the eluent. Yield 11 mg (90%). $^1H$ NMR (500 MHz, CDCl$_3$) δ 8.05 (d, J=7.7 Hz, 1H), 7.75-7.70 (m, 1H), 7.70-7.65 (m, 1H), 7.25-7.19 (m, 1H), 6.50 (s, 1H), 6.48-6.43 (m, 1H), 6.40-6.38 (m, 1H), 4.27-4.20 (m, 2H), 3.47-3.38 (m, 1H), 3.22-3.12 (m, 1H), 2.75-2.68 (m, 0.5H), 2.67-2.59 (m, 0.5H), 2.44 (t, J=6.8 Hz, 2H), 2.05-1.88 (m, 2H), 1.71-1.68 (m, 0.5H), 1.68-1.65 (m, 0.5H), 1.50-1.40 (m, 2H), 1.36-1.33 (m, 3H), 1.32-1.31 (m, 3H), 1.18 (s, 3H), 1.06 (d, J=6.6 Hz, 1.5H), 0.96 (d, J=6.6 Hz, 1.5H); $^{13}C$ NMR (126 MHz, CDCl$_3$) δ 173.07, 173.03, 168.80, 168.77, 151.88, 151.69, 150.24, 150.16, 150.14, 148.17, 147.62, 147.42, 145.01, 142.94, 138.39, 135.38, 135.31, 130.34, 130.29, 126.91, 126.69, 126.48, 125.41, 124.48, 123.98, 123.80, 122.40, 121.54, 121.45, 121.40, 119.85, 117.30, 114.75, 109.49, 109.46, 109.42, 109.33, 109.29, 109.25, 103.11, 97.89, 97.85, 82.20, 82.06, 60.71, 55.19, 55.06, 46.32, 46.25, 44.60, 44.41, 31.93, 31.69, 31.66, 29.70, 29.42, 29.37, 29.29, 26.91, 26.74, 25.77, 25.33, 23.42, 23.28, 22.70, 19.61, 19.46, 14.29, 14.12; $^9F$ NMR (376 MHz, CDCl$_3$) δ −72.85, −72.87, −72.89, −131.09, −131.11, −141.66. LRMS (EI) m/z (%) 695.1 (M$^+$; 10), 85.0 (100); HRMS (EI): calcd for C$_{33}$H$_{30}$O$_8$NF$_5$S (M$^+$): 695.1612, Found: 695.1605.

Example 3—Synthesis of Mitochondria-Targeted Green Fluorogenic Compound HKSOX-1m

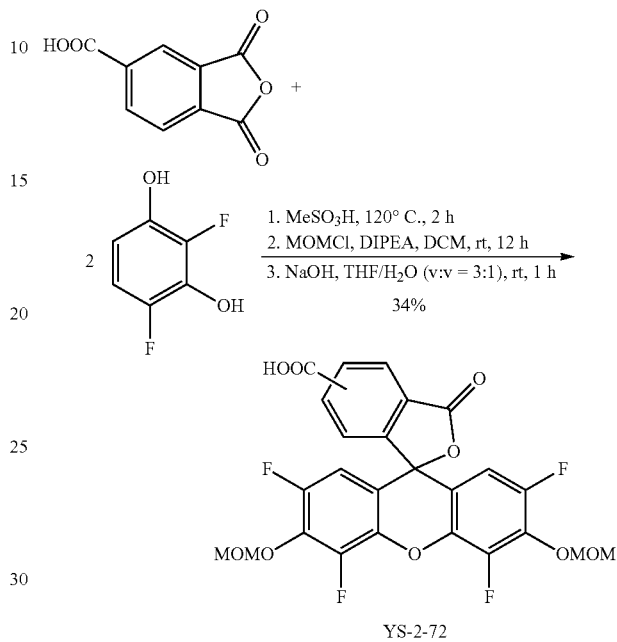

1) To a mixture of trimellitic anhydride (175 mg, 0.912 mmol), 2,4-difluororesorcinol (266 mg, 1.824 mmol) was added MeSO$_3$H (3 mL) under argon atmosphere. The resulting mixture was heated to 120° C. for 2 h, then cooled to room temperature, and quenched with water. The red solid precipitate was collected by filtration, washed by water, and dried over air to afford 5(6)-carboxy-2',4',5',7'-tetrafluorofluorescein as red solid.

2) To a solution of 5(6)-carboxy-2',4',5',7'-tetrafluorofluorescein (198 mg, 0.443 mmol) in dry DCM (2 mL), DIPEA (0.366 mL, 2.22 mmol) was added under argon atmosphere. Then chloromethyl methyl ether (0.168 mL, 2.22 mmol) was added dropwise. The resulting mixture was stirred 12 h at room temperature, and then diluted with ethyl acetate, washed by 1N HCl, water, and brine. The organic layer was dried over MgSO$_4$, and concentrated in vacuo. The methoxymethyl protected product was isolated by flash chromatography on silica gel, using MeOH:DCM (1:99) as the eluent.

3) To a solution of the methoxymethyl protected product (180 mg, 0.310 mmol) in THF (6 mL), NaOH (124 mg, 3.10 mmol) in water (2.0 mL) was added dropwise at room temperature. The resulting solution was stirred for 1 h. And then diluted with ethyl acetate, washed by 1N HCl, water, and brine. The organic layer was dried over MgSO$_4$, and concentrated in vacuo. Compound YS-2-72 was isolated as a white sticky solid by flash chromatography on silica gel, using MeOH:DCM (1:24) as the eluent (165 mg, 34% yield). $^1H$ NMR (400 MHz, CDCl$_3$) δ 8.76 (s, 0.5H), 8.42 (d, J=8.1 Hz, 0.5H), 8.39 (d, J=8.0 Hz, 0.5H), 8.15 (d, J=8.0 Hz, 0.5H), 7.88 (s, 0.5H), 7.29 (d, J=8.1 Hz, 0.5H), 6.35 (t, J=8.6 Hz, 2H), 5.23 (s, 4H), 3.60 (s, 6H); $^{13}C$ NMR (100 MHz, CDCl$_3$) δ 169.1, 167.2, 156.0, 153.5, 151.8, 151.0, 146.7, 144.2, 137.2, 136.3, 132.4, 129.6, 128.0, 126.0, 125.6, 124.2, 113.6, 113.5, 108.4, 108.2, 99.0, 80.5, 57.4; $^{19}$F NMR (376 MHz, CDCl$_3$) δ −130.6 (m, 2F), −145.3 (d, J=6.2 Hz, 2F); LRMS (EI) m/z (%) 536.4 (M$^+$; 72), 337.3 (100); HRMS (EI): calcd for C$_{25}$H$_{16}$F$_4$O$_9$ (M): 536.0730, found: 536.0756.

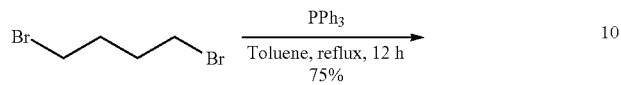

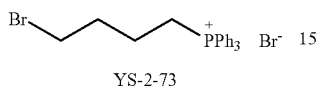

YS-2-73

A solution of 1,4-dibromobutane (1.18 mL, 10.0 mmol) and triphenylphosphine (2.62 g, 10.0 mmol) in dry toluene (20.0 mL) was heated to reflux under argon atmosphere for 12 h. Then the reaction was cooled down to room temperature, and then filter to get the white solid. Washed with ethyl ether 3 times, and then dried over air to get YS-2-73 as white sticky solid (3.58 g, 75% yield). NMR $^1$H NMR (400 MHz, CDCl$_3$) δ 7.76-7.56 (m, 15H), 3.77-3.61 (m, 2H), 3.38 (t, J=6.1 Hz, 2H), 2.20-2.05 (m, 2H), 1.68 (m, 2H); $^{13}$C NMR (100 MHz, CDCl$_3$) δ 134.75, 134.72, 133.27, 133.18, 130.21, 130.08, 117.99, 117.13, 33.23, 31.72, 31.56, 21.49, 20.98, 20.46; $^{31}$P NMR (162 MHz, CDCl$_3$) δ 24.3; LRMS (EI) m/z (%) 399.1 (M$^+$; 100), 397.1 (M$^+$; 98).

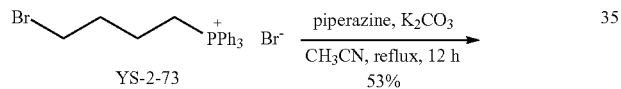

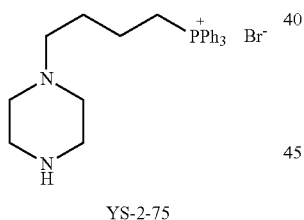

YS-2-75

To a suspension of piperazine (516 mg, 6.00 mmol) and K$_2$CO$_3$ (524 mg, 4.00 mmol) in acetonitrile (50.0 mL), YS-2-73 (956 mg, 2.00 mmol) is acetonitrile (20.0 mL) was added slowly at room temperature under argon atmosphere. Then the system was heated to reflux for 12 h. Concentrated in vacuo, and then diluted with ethyl acetate, washed by water, and brine. The organic layer was dried over MgSO$_4$, and concentrated to get YS-2-75 as a white sticky solid (510 mg, 53% yield). $^1$H NMR (400 MHz, CDCl$_3$) δ 7.5-7.36 (m, 15H), 3.38 (m, 2H), 2.49 (m, 3H), 2.34 (s, 1H), 2.21-1.85 (m, 6H), 1.59-1.46 (m, 2H), 1.45-1.31 (m, 2H); $^{13}$C NMR (100 MHz, CDCl$_3$) δ 134.33, 134.31, 132.81, 132.71, 129.79, 129.67, 117.76, 116.91, 77.26, 56.23, 53.33, 52.26, 45.13, 25.42, 25.26, 21.39, 20.89, 19.34, 19.31; $^{31}$P NMR (162 MHz, CDCl$_3$) δ 24.3; LRMS (ESI) m/z (%) 403.3 (M$^+$; 20), 360.5 (100); HRMS (ESI): calcd for C$_{26}$H$_{32}$N$_2$P (M$^+$): 403.2303, found: 403.2302.

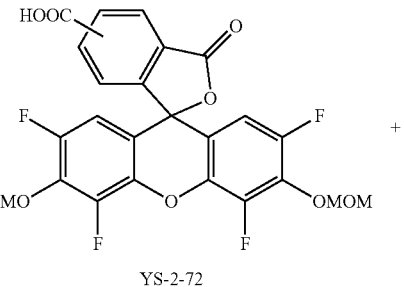

YS-2-72

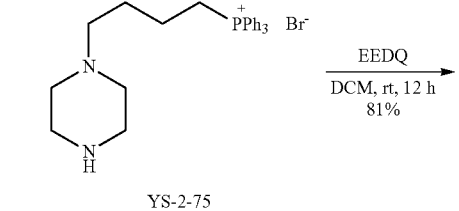

YS-2-75

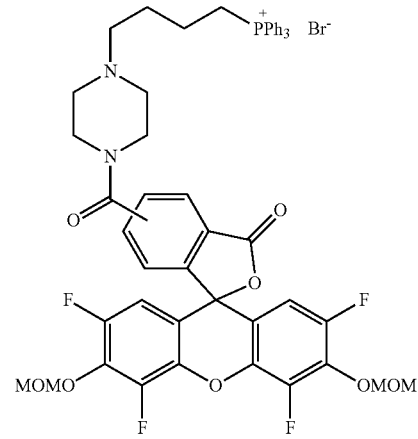

YS-2-77

To a solution of YS-2-72 (42 mg, 0.0789 mmol) in dry DCM (5 mL) was added EEDQ (29 mg, 0.118 mmol) under argon atmosphere. After 15 minutes, YS-2-75 (46 mg, 0.0953 mmol) in dry DCM (2 mL) was added. The resulting solution was stirred for 12 h at room temperature, and then diluted with ethyl acetate, washed by 1N HCl, water, and brine. The organic layer was dried over MgSO$_4$, and concentrated in vacuo. Compound YS-2-77 was isolated as a white sticky solid by flash chromatography on silica gel, using EtOH:DCM (3:7) as the eluent (64 mg, 81% yield). $^1$H NMR (400 MHz, CDCl$_3$) δ 8.03 (d, J=7.8 Hz, 0.5H), 7.99 (s. 0.5H), 7.92-7.54 (m, 16H), 7.21 (d, J=7.9 Hz, 0.5H), 7.18 (s, 0.5H), 6.36 (d, J=10.3 Hz, 2H), 5.19 (s, 4H), 4.03-3.81 (m, 2H), 3.78-3.68 (m, 1H), 3.68-3.62 (m, 1H), 3.56 (s, 6H), 3.39 (m, 1H), 3.25 (m, 1H), 2.74-2.32 (m, 6H), 2.07-1.79 (m, 2H), 1.65 (m, 2H); $^{13}$C NMR (100 MHz, CDCl$_3$) δ 167.8, 167.5, 153.4, 152.3, 152.2, 150.9, 146.5, 144.0, 143.2, 138.7, 134.9, 134.7, 133.7, 133.6, 130.4, 130.3, 129.4, 125.9, 125.6, 124.2, 122.6, 118.9, 118.0, 113.8, 108.3, 98.9, 80.1, 57.3, 56.5, 52.8, 26.5, 22.2, 21.7, 20.2; $^{19}$F NMR (376 MHz, CDCl$_3$) δ −130.5 (m, 2F), −145.6 (d, J=15.4 Hz, 2F); $^{31}$P NMR (162 MHz, CDCl$_3$) δ 24.6; LRMS (ESI) m/z (%) 921.3 (M$^+$; 100), 877.3 (39); HRMS (ESI): calcd for C$_{51}$H$_{46}$F$_4$N$_2$O$_8$P (M$^+$): 921.2922, found: 921.2953.

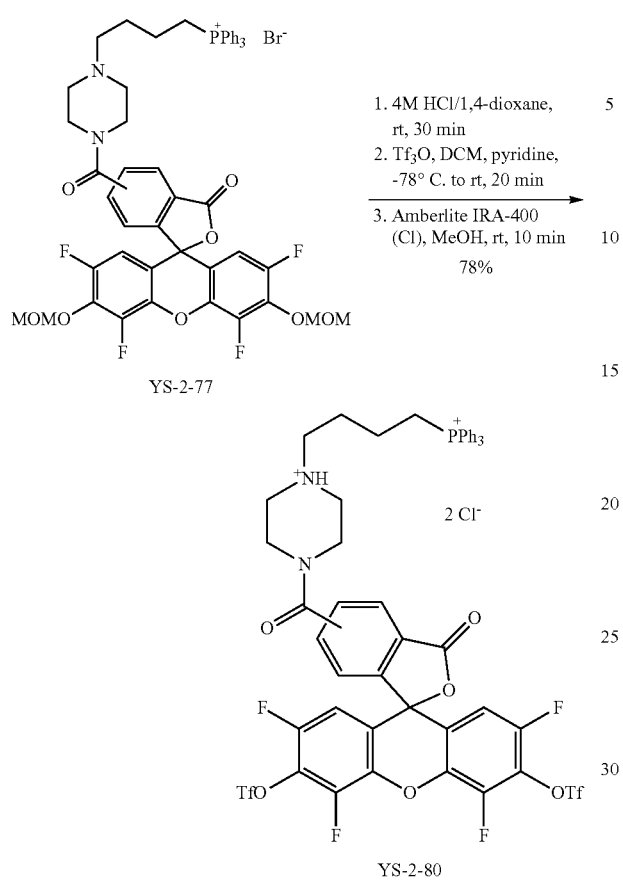

YS-2-77

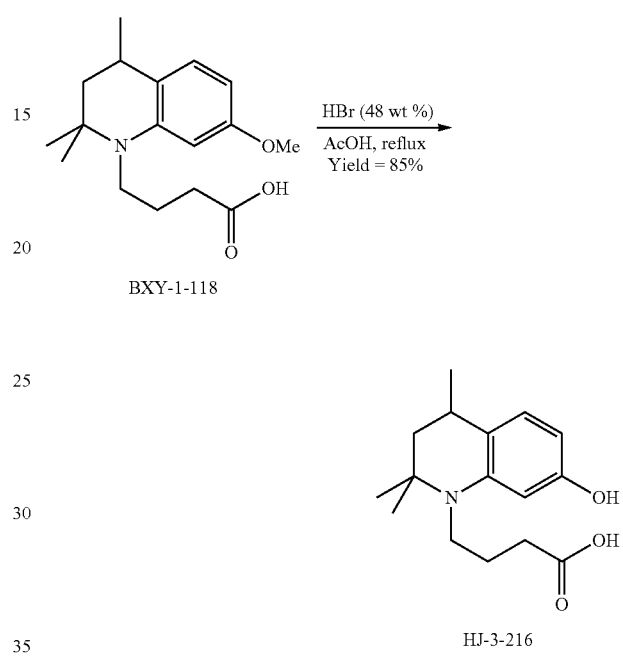

YS-2-80

1) To YS-2-77 (64 mg, 0.0639 mmol) was added 4 M HCl in 1,4-dioxane solution (1 mL) at room temperature, and concentrated in vacuo after 30 min.

2) The product was dissolved in dry DCM (2 mL) and anhydrous pyridine (2 mL), cooled down to −78° C. in a dry ice/acetone bath. Tf$_2$O (54 mg, 0.192 mmol) was then added dropwise under argon atmosphere. The resulting mixture was stirred at −78° C. for 10 min and then at room temperature for another 10 min. The reaction mixture was diluted with ethyl acetate, washed by 1N HCl, water, and brine. The organic layer was dried over MgSO$_4$, and concentrated in vacuo.

3) Amberlite IRA-400 (Cl) was stirred in brine for 1 h, washed by 1N HCl, brine, and MeOH and then dried over air. To the crude product in MeOH, was added the pretreated Amberlite IRA-400 (Cl), followed by filtration to get the filtrate. The filtrate was concentrated in vacuo. Compound YS-2-80 was isolated as a white sticky solid by flash chromatography silica gel, using EtOH:DCM (3:7) as the eluent (58 mg, 78% yield). $^1$H NMR (400 MHz, CDCl$_3$) δ 8.11 (d, J=7.9 Hz, 0.5H), 8.07 (s, 0.5H), 7.85-7.66 (m, 16H), 7.29 (d, J=7.6 Hz, 1H), 6.67 (dd, J=9.0, 1.8 Hz, 2H), 3.75 (s, 1H), 3.68 (s, 1H), 3.50-3.37 (m, 3H), 3.32 (s, 1H), 2.51 (m, 6H), 1.88-1.77 (m, 2H), 1.73-1.62 (m, 2H); $^{13}$C NMR (100 MHz, CDCl$_3$) δ 167.48, 167.25, 166.84, 166.73, 152.10, 151.34, 149.57, 145.73, 143.75, 143.14, 139.51, 136.47, 135.38, 135.22, 135.20, 133.52, 133.41, 130.62, 130.50, 130.24, 126.64, 125.10, 124.98, 124.10, 123.29, 122.62, 120.10, 119.89, 119.83, 119.75, 119.68, 118.54, 118.50, 117.68, 117.65, 116.91, 109.45, 109.28, 109.08, 78.49, 56.39, 52.68, 52.46, 26.55, 26.38, 21.99, 21.48, 20.14; $^{19}$F NMR (376 MHz, CDCl$_3$) δ −73.1, −126.4, −126.6, −138.9, −139.3; $^{31}$P NMR (162 MHz, CDCl$_3$) δ 24.1; LRMS (ESI) m/z (%) 1097 (M$^+$; 100), 965 (11); HRMS (ESI): calcd for C$_{49}$H$_{36}$F$_{10}$N$_2$O$_{10}$PS$_2$ (M$^+$): 1097.1389, found: 1097.1401.

Example 4—Synthesis Of Mitochondria-Targeted Yellow Fluorogenic Compound HKSOX-2m

BXY-1-118

HJ-3-216

To a solution of BXY-1-118 in AcOH at room temperature, was added Her (48 wt %) slowly. The resulting mixture was stirred under reflux for 12 hrs. The reaction mixture was allowed to cool to room temperature, diluted with ethyl acetate, and washed with 1N HCl, water, and brine. The organic layer was dried over anhydrous magnesium sulfate and concentrated in vacuo. The target compound HJ-3-216 was isolated by flash column chromatography on silica gel, using EtOAc:Hexane (1:1) as the eluent. Yield (419 mg) (85%). $^1$H NMR (400 MHz, CDCl$_3$) δ 9.48 (br, 2H), 6.99 (d, J=83 Hz, 1H), 6.41 (s, 1H), 6.34 (d, J=7.1 Hz, 1H), 3.33-3.18 (m, 1H), 3.18-3.07 (m, 1H), 2.87-2.76 (m, 1H), 2.55-2.37 (m, 1H), 2.05-1.92 (m, 1H), 1.90-1.78 (m, 1H), 1.73 (dd, J=13.3, 5.1 Hz, 1H), 1.52 (t, J=12.7 Hz, 1H), 1.31 (s, 3H), 1.28 (s, 1.5H), 1.27 (s. 1.5H), 1.15 (s, 3H); $^{13}$C NMR (100 MHz, CDCl$_3$) δ 179.03, 155.31, 144.35, 127.41, 120.74, 105.31, 100.90, 55.73, 46.88, 45.44, 32.52, 28.99, 26.78, 24.69, 23.74, 20.61.

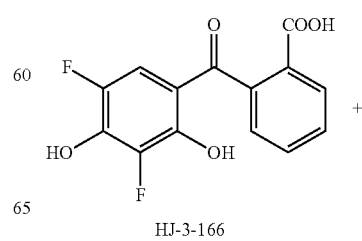

HJ-3-166

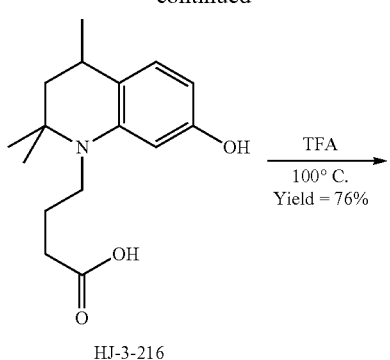

HJ-3-216

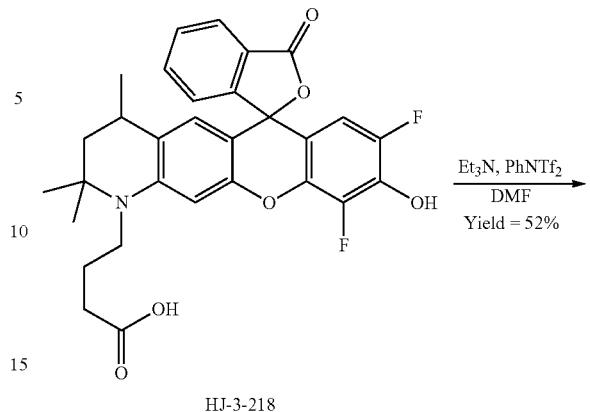

HJ-3-218

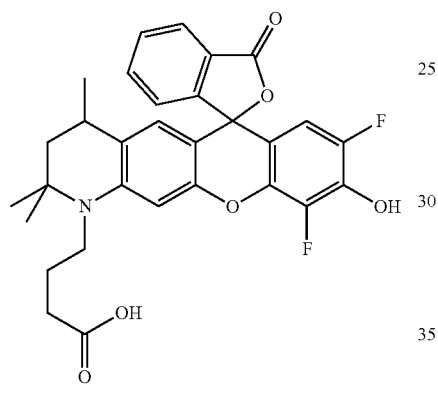

HJ-3-218

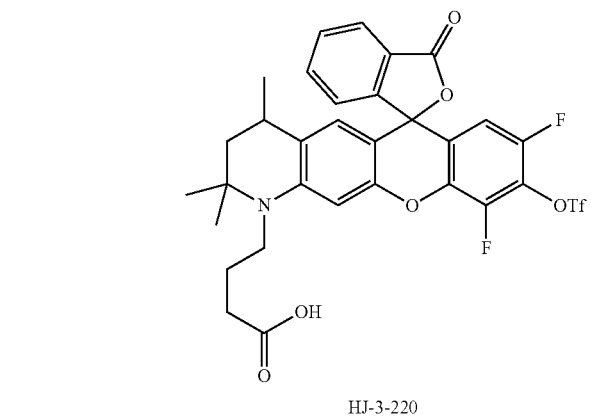

HJ-3-220

The solution of HJ-3-166 (66 mg, 0.238 mmol) and HJ-3-216 (70 mg, 0.238 mmol) in TFA (2.4 mL) in sealed tube was heated to 100° C. under argon atmosphere. The resulting mixture was stirred at 100° C. for 3 hrs and allowed to cool down to room temperature. The reaction mixture was concentrated in vacuo. The target compound HJ-3-218 was isolated by flash column chromatography on silica gel, using MeOH:DCM: (1:9) (with 0.25% AcOH) as the eluent. Yield (97 mg) (76%). $^1$H NMR (400 MHz, CDCl$_3$) δ 8.23 (t, J=7.0 Hz, 1H), 7.78-7.64 (m, 2H), 7.43 (d, J=7.0 Hz, 0.5H), 7.36 (d, J=7.0 Hz, 0.5H), 6.97 (s, 1H), 6.94 (s, 0.5H), 6.93 (s, 0.5H), 6.62 (d, J=6.2 Hz, 0.5H), 6.59 (d, J=6.2 Hz, 0.5H), 3.71-3.57 (m, 1H), 3.51-3.40 (m, 1H), 2.90-2.80 (m, 0.5H), 2.79-2.69 (m, 0.5H), 2.44 (br, 2H), 2.07-1.99 (m, 1H), 1.95-1.89 (m 1H), 1.88-1.78 (m, 1H), 1.58 (t, J=13.3 Hz, 1H), 1.45 (s, 1.5H), 1.44 (s, 1.5H), 1.34 (s, 1.5H), 1.30 (s, 1.5H), 1.09 (t, J=6.5 Hz, 3H); $^{19}$F NMR (376 MHz, CDCl$_3$) δ −76.97, −131.55, −131.59, −131.62, −131.66, −131.71, −131.74, −163.52, −163.57, −163.61, −163.65.

To a solution of HJ-3-218 (81 mg, 0.151 mmol) Et$_3$N in anhydrous DMF (5 mL) at room temperature, were added Et$_3$N (63 μL, 0.454 mmol) and PhNTf$_2$ (65 mg, 0.182 mmol) successively under argon atmosphere. The resulting mixture was stirred at room temperature for 1 h. Then the reaction mixture was diluted with ethyl acetate, and washed with 1N HCl, water, and brine. The organic layer was dried over anhydrous magnesium sulfate and concentrated in vacuo. The target compound HJ-3-220 was isolated by flash column chromatography on silica gel, using MeOH:DCM (1:19) as the eluent. Yield (52 mg) (52%). $^1$H NMR (400 MHz, CDCl$_3$) δ 8.06 (d, J=7.4 Hz, 1H), 7.77-7.70 (m, 1H), 7.68 (t, J=7.1 Hz, 1H), 7.25-7.19 (m, 1H), 6.55 (s, 1H), 6.49-6.43 (m, 1H), 6.39 (s, 1H), 3.51-3.43 (m, 1H), 3.26-3.14 (m, 1H), 2.77-2.58 (m, 1H), 2.52 (t, J=6.0 Hz, 2H), 2.04-1.86 (m, 2H), 1.73-1.66 (m, 1H), 1.47 (t, 12.9 Hz, 1H), 1.32 (d, J=2.5 Hz, 3H), 1.18 (s, 3H), 1.09-0.94 (m, 3H); $^{13}$C NMR (100 MHz, CDCl$_3$) δ 179.11, 169.01, 151.99, 151.81, 150.49, 150.35, 147.99, 147.69, 147.49, 145.41, 142.82, 135.54, 135.48, 130.48, 130.43, 127.18, 126.77, 126.69, 126.57, 125.54, 124.58, 124.11, 123.88, 121.54, 120.27, 117.09, 109.59, 109.55, 109.39, 109.36, 103.31, 98.17, 98.09, 82.99, 82.94, 70.74, 55.35, 55.20, 46.46, 46.36, 44.58, 44.38, 31.22, 29.50, 29.35, 27.03, 26.86, 26.59, 25.90, 25.43, 23.17, 23.00, 19.70, 19.53; $^{19}$F NMR (376 MHz, CDCl$_3$) δ −72.9 (t, 6.0 Hz, 3F), −131.2 (m, 1F), −141.3 (m, 1F); LRMS (EI, 20 eV) m/z (%) 667 (M$^+$; 11), 111 (100); HRMS (EI): calcd for C$_{31}$H$_{26}$O$_8$NF$_5$S (M$^+$): 667.1299, found: 667.1302.

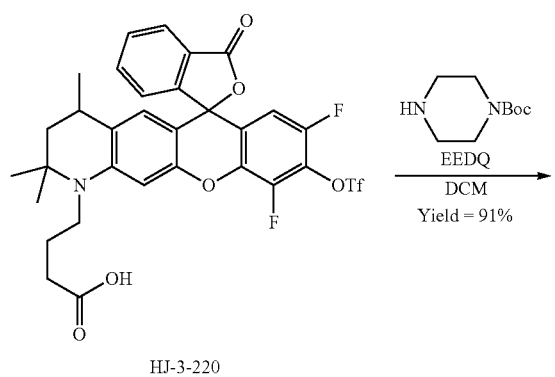

HJ-3-220

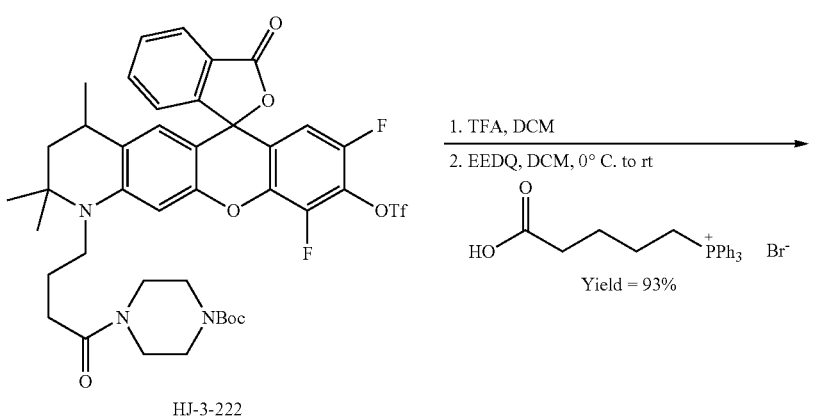

HJ-3-222

To a solution of HJ-3-220 (28 mg, 0.0419 mmol) in dry DCM at 0° C., was added EEDQ (21 mg, 0.0839 mmol) and amine (16 mg, 0.0839 mmol) successively under argon atmosphere. The resulting mixture was stirred at 0° C. to room temperature for 24 hrs. The reaction mixture was diluted with DCM, washed with 1N HCl, water, and brine. The organic layer was dried over anhydrous magnesium sulfate and concentrated in vacuo. The target compound HJ-3-222 was separated by flash column chromatography on silica gel, using EtOAc:Hexane (1:1) as the eluent. Yield (32 mg) (91%). $^1$H NMR (400 MHz, CDCl$_3$) δ 8.05 (d, J=7.5 Hz, 1H), 7.77-7.64 (m, 2H), 7.23 (d, J=7.5 Hz, 0.5H), 7.20 (d, J=7.5 Hz, 0.5H), 6.50 (s, 1H), 6.46 (d, J=2.1 Hz, 0.5H), 6.44 (d, J=2.1 Hz, 0.5H), 6.38 (s, 1H), 3.70-3.60 (m, 2H), 3.48 (br, 4H), 3.47-3.40 (m, 2H), 3.25-3.12 (m, 1H), 2.75-2.66 (m, 0.5H), 2.66-2.57 (m, 0.5H), 2.45 (t, J=6.6 Hz, 2H), 2.01-1.90 (m, 2H), 1.73-1.61 (m, 3H), 1.48 (s, 9H), 1.34 (s, 1.5H), 1.33 (s, 1.5H), 1.18 (s, 3H), 1.06 (d, J=6.6 Hz, 1.5H), 0.96 (d, J=6.5 Hz, 1.5H); $^{13}$C NMR (75 MHz, CDCl$_3$) δ 170.90, 168.93, 154.72, 151.97, 151.76, 150.92, 150.35, 147.76, 147.59, 147.57, 145.81, 145.77, 142.34, 135.54, 135.46, 130.48, 130.43, 126.81, 126.62, 126.58, 125.53, 124.55, 124.13, 123.90, 121.58, 120.81, 116.55, 109.71, 109.67, 109.44, 109.40, 109.34, 103.04, 103.02, 97.97, 97.91, 80.54, 55.32, 55.20, 46.44, 46.37, 45.44, 44.98, 44.76, 43.64, 41.62, 30.60, 30.51, 29.84, 29.57, 29.45, 28.50, 27.03, 26.86, 25.96, 25.54, 23.49, 23.40, 19.69, 19.57; $^{19}$F NMR (376 MHz, CDCl$_3$) δ −72.85, −72.86, −72.88, −131.12, −141.67.

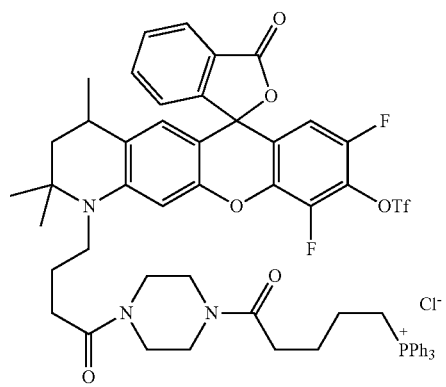

HKSOX-2m

To a solution of HJ-3-222 (7 mg, 0.00837 mmol) in DCM (1 mL) at room temperature, was added TFA (1 mL) slowly. The resulting mixture was stirred at room temperature for 1 h. The reaction mixture was concentrated in vacuo and azeotroped with toluene for 3 times to obtain the crude residue. To a solution of (4-carboxybutyl)triphenylphosphonium bromide (11 mg, 0.0251 mmol) and EEDQ (7 mg, 0.0276 mmol) in dry DCM (2 mL) at 0° C., was added the solution of the crude residue in dry DCM (2 mL) under argon atmosphere. The resulting mixture was stirred at 0° C. to room temperature for 12 h. The reaction mixture was diluted with DCM, washed with 1N HCl, water, and brine. The organic layer was dried over anhydrous magnesium sulfate and concentrated in vacuo. Amberlite IRA-400 (Cl) was stirred in brine for 1 h, washed by 1N HCl, brine, and MeOH, and then dried over air. To the crude residue in MeOH, was added the pretreated Amberlite IRA-400 (Cl), followed by filtration to get the filtrate. The filtrate was concentrated in vacuo. The target compound HKSOX-2m was isolated as a pink sticky solid by flash column chromatography on silica gel, by using EtOH:CHCl$_3$ (1:4) as an cheat. Yield (9 mg) (93%). $^1$H NMR (400 MHz, CDCl$_3$) δ 8.04 (d, J=7.4 Hz, 1H), 7.91-7.75 (m, 10H), 7.74-7.63 (m, 6H), 7.25-7.18 (m, 1H), 6.56 (s, 1H), 6.46-6.40 (m, 1H), 6.37 (s, 1H), 3.91-3.72 (m, 3H), 3.69-3.53 (m, 5H), 3.50-3.39 (m, 1H), 3.25-3.10 (m, 1H), 2.80 (brs, 1H), 2.75-2.55 (m, 1H), 2.46 (brs, 2H), 2.08-1.88 (m, 5H), 1.78 (brs, 4H), 1.70-1.53 (m, 3H), 1.49-1.40 (m, 2H), 1.35-1.31 (m, 3H), 1.17 (s, 1H), 1.07-0.92 (m, 3H); $^1$C NMR (125 MHz, CDCl$_3$) δ 173.31, 171.57, 169.17, 151.72, 151.49, 150.33, 150.20, 150.10, 148.10, 147.80, 147.62, 145.00, 142.94, 138.47, 135.62, 135.53, 135.41, 135.40, 135.24, 133.62, 133.59, 133.51, 133.42, 130.71, 130.61, 130.52, 127.00, 126.67, 126.41, 125.40, 124.40, 124.30, 124.10, 123.84, 123.76, 121.45, 119.84, 118.55, 118.50, 118.32, 117.87, 117.82, 117.63, 117.29, 109.41, 102.85, 97.90, 97.78, 60.68, 55.23, 51.71, 46.28, 45.70, 45.31, 45.11, 44.71, 44.62, 44.54, 41.85, 41.62, 41.52, 41.37, 33.13, 32.17, 30.41, 29.69, 29.27, 26.89, 26.77, 25.70, 25.57, 25.43, 23.35, 22.59, 22.14, 21.88, 19.44, 14.09; $^{19}$F NMR (376 MHz, CDCl$_3$) δ −72.9 (m, 3F), −131.4 (m, 1F), −141.1 (m, 1F); LRMS (FAB) m/z: 307 (100), 1080 (M$^+$, 30); HRMS (ESI): calcd for C$_{58}$H$_{56}$O$_3$N$_8$F$_5$SP (M$^+$): 1080.3441, found: 1080.3487.

Example 5—Synthesis of Lysosome-Targeted Yellow Fluorogenic Compound HKSOX-Lyso

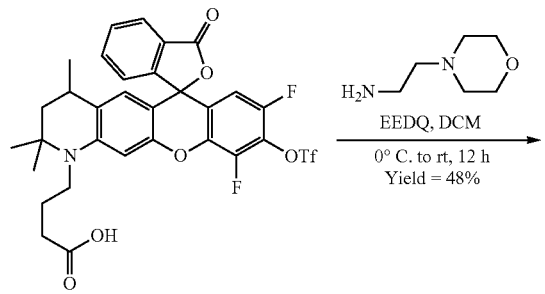

HJ-3-220

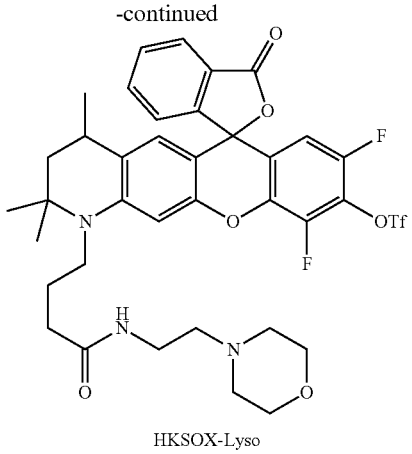

HKSOX-Lyso

To a solution of HJ-3-220 (50 mg, 0.0749 mmol) in dry DCM at 0° C., was added EEDQ (61 mg, 0.16 mmol) and 4-(2-aminoethyl)morpholine (20 mg, 0.15 mmol) successively under argon atmosphere. The resulting mixture was stirred at 0° C. to room temperature for 12 h. The reaction mixture was diluted with DCM, washed with 1N HCl, water, and brine. The organic layer was dried over anhydrous magnesium sulfate and concentrated in vacuo. The target compound HKSOX-Lyso was separated by flash column chromatography on silica gel, using MeOH:DCM (1:20) as the eluent. Yield (28 mg) (48%), $^1$H NMR (400 MHz, CDCl$_3$) δ 8.05 (d, J=7.5 Hz, 1H), 7.73 (td, J=7.4, 3.3 Hz, 1H), 7.67 (dd, J=10.0, 4.8 Hz, 1H), 7.22 (dd, 11.5, 7.6 Hz, 1H), 6.49-6.41 (m, 2H), 6.38 (s, 1H), 6.10 (s, 1H), 3.79-3.67 (m, 4H), 3.53-3.44 (m, 1H), 3.44-3.38 (m, 2H), 3.18 (td, J=15.0, 6.9 Hz, 1H), 2.77-2.57 (m, 1H), 2.52 (t, J=6.0 Hz, 2H), 2.47 (s, 4H), 2.32 (t, J=7.0 Hz, 2H), 1.99-1.86 (m, 2H), 1.69-1.46 (m, 8.7 Hz, 2H), 1.32 (s, 3H), 1.17 (s, 3H), 1.07-0.96 (m, 3H); $^{13}$C NMR (100 MHz, CDCl$_3$) δ 172.1, 168.8, 151.8, 151.6, 150.5, 147.9, 147.5, 145.2, 142.6, 135.4, 130.3, 126.7, 126.5, 125.4, 124.4, 123.9, 121.5, 109.5, 109.3, 102.9, 97.7, 66.9, 57.1, 55.1, 53.3, 46.2, 44.5, 35.6, 33.5, 29.4, 26.8, 25.8, 25.4, 24.0, 19.5; $^{19}$F NMR (376 MHz, CDCl$_3$): δ −72.89 (s, 3F), −131.11 (s, 1F), −141.73 (s, 1F); LRMS (ESI) m/z: 662 (100), 780 (M$^+$, 30).

Example 6—Synthesis of Fret-Based Green Fluorogenic Compound HJ-3-241-2

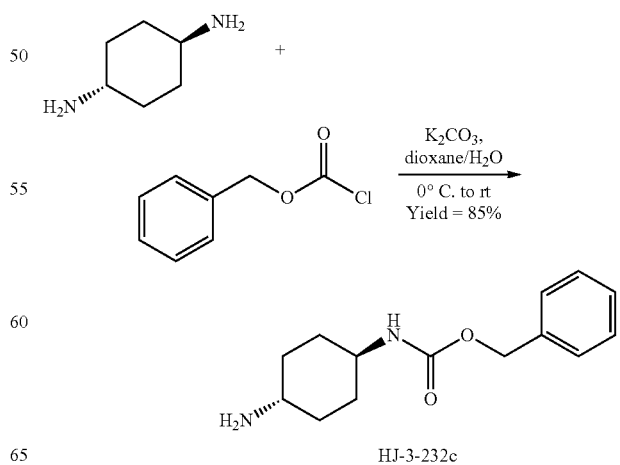

HJ-3-232c

To a solution of trans-1,4-diaminocyclohexane (1.14 g, 10 mmol) and potassium carbonate (2.76 g, 20 mmol) in 1,4-dioxane (90 mL) and H$_2$O (10 mL) at 0° C. was added benzyl chloroformate (1.4 mL, 10 mmol) dropwise for 1 h under argon atmosphere. Then the resulting mixture was stirred at 0° C. to room temperature for 12 h. The reaction mixture was diluted with DCM and H$_2$O, and extracted with DCM for 3 times. The organic layer was dried over anhydrous sodium sulfate and concentrated in vacuo to obtain crude product. Yield HJ-3-232c (2.1 g) (85%). $^1$H NMR (400 MHz, CDCl$_3$) δ 7.41-7.28 (m, 5H), 5.08 (s, 2H), 4.72-4.52 (m, 1H), 3.55-3.35 (m, 1H), 2.33-2.51 (m, 1H), 2.09-1.79 (m, 4H), 1.28-1.07 (m, 4H). $^{13}$C NMR (100 MHz, CDCl$_3$) δ 155.73, 136.74, 128.65, 128.25, 128.22, 66.67, 49.97, 49.82, 49.46, 35.40, 32.22, 31.99.

room temperature for another 12 h. Then the reaction mixture was diluted with DCM and washed with 1N HCl, H$_2$O and brine. The organic layer was dried over anhydrous magnesium sulfate and concentrated in vacuo. The target compound HJ-3-234 was separated by flash column chromatography on silica gel, using EtOAc:DCM (3:17) as the eluent. Yield HJ-3-234 (120 mg) (66%). $^1$H NMR (300 MHz, CDCl$_3$) δ 8.70 (d, J=7.9 Hz, 1H), 8.66 (s, 1H), 7.40-7.28 (m, 5H), 6.61 (dd, J=9.0, 2.3H; 1H), 6.48 (d, J=2.2 Hz, 1H), 5.08 (s, 2H), 4.86 (d, J=7.7 Hz, 1H), 4.00-3.81 (m, 1H), 3.61-3.50 (m, 1H), 3.43 (q, J=7.1 Hz, 4H), 2.18-1.98 (m, 4H), 1.45-1.27 (m 4H), 1.22 (t, J=7.1 Hz, 6H), $^{13}$C NMR (75 MHz, CDCl$_3$) δ 162.82, 162.48, 157.69, 155.75, 152.58, 148.14, 136.76, 131.18, 128.61, 128.15, 110.38, 109.99, 108.48, 96.64, 66.60, 49.51, 47.89, 45.15, 32.05, 31.54, 12.52.

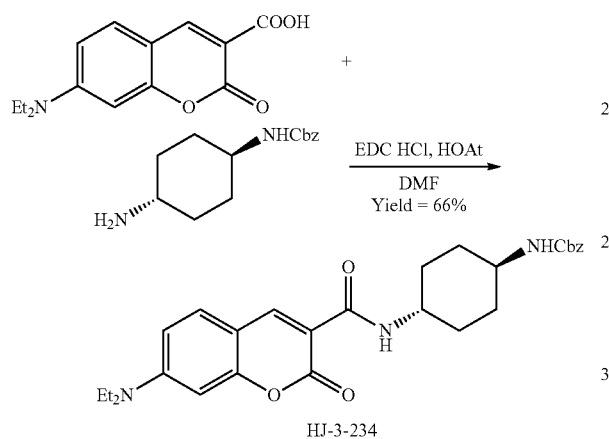

HJ-3-234

To a solution of 7-(diethylamino)coumarin-3-carboxylic acid (97 mg, 0.371 mmol) and HJ-3-232c (184 mg, 0.742 mmol) in anhydrous DMF at room temperature, was added HOAt under argon atmosphere. After 30 min of stirring, EDC.HCl was added and the resulting mixture was stirred at

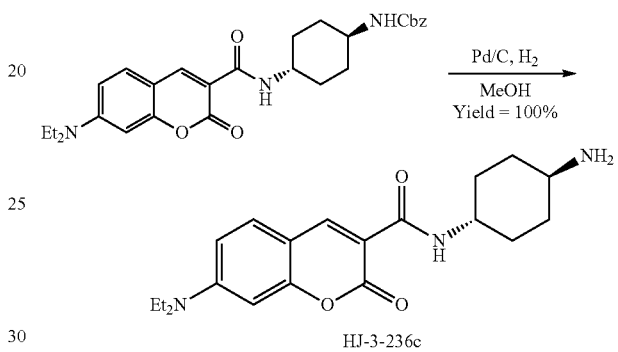

HJ-3-236c

To a solution of HJ-3-234 (80 mg, 0.163 mmol) in MeOH at room temperature, was added Pd/C slowly under argon atmosphere. The resulting mixture was stirred under H$_2$ atmosphere for 8 h. The reaction mixture was filtered over a pad of celite and concentrated in vacuo to obtain crude product HJ-3-236c (58 mg, quantitative yield) which was used directly in next step.

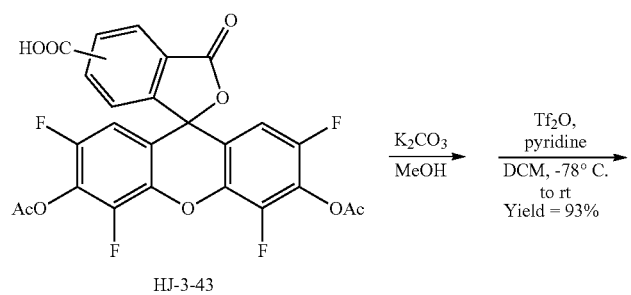

HJ-3-43

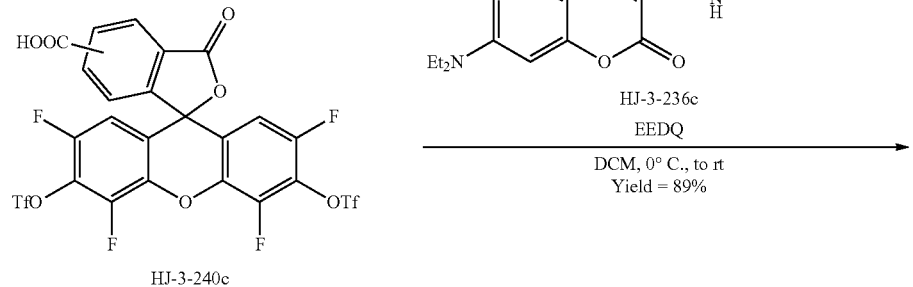

HJ-3-240c

-continued

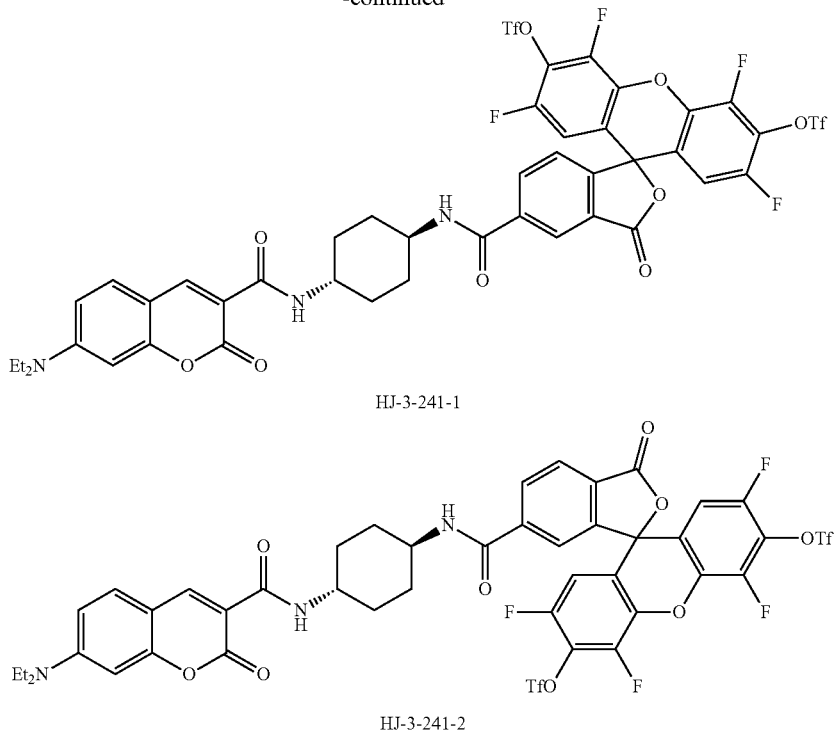

HJ-3-241-1

HJ-3-241-2

To a solution of HJ-3-43 (120 mg, 0.225 mmol) in MeOH (10 mL) at room temperature, was added K$_2$CO$_3$ (312 mg, 2.25 mmol). The resulting mixture was stirred at room temperature for 2 hrs. The reaction mixture was concentrated to evaporate the organic solvent, diluted with ethyl acetate and washed with 1N HCl, water, and brine. The organic layer was dried over anhydrous magnesium sulfate and concentrated in vacuo. The residue was dissolved in dry DCM (2 mL) and anhydrous pyridine (2 mL) and added with Tf$_2$O dropwise at −78° C. under argon atmosphere. The resulting mixture was stirred at −78° C. to at room temperature for 3 h. The reaction mixture was quenched with water, diluted with DCM and washed with 1N HCl, water, and brine. The organic layer was dried over anhydrous magnesium sulfate and concentrated in vacuo to obtain crude product HJ-3-240c (150 mg, yield=93%) which was directly used in next step.

To a solution of HJ-3-240c (42 mg, 0.059 mmol) and EEDQ (16 mg, 0.065 mmol) in dry DCM (5 mL) at 0° C., was added HJ-3-236c (23 mg, 0.065 mmol) under argon atmosphere. The resulting mixture was stirred at 0° C. to room temperature for 12 h. The reaction mixture was diluted with DCM, washed with 1N HCl, water, and brine. The organic layer was dried over anhydrous magnesium sulfate and concentrated in vacuo. The target compound HJ-3-241-1 (5 isomer) and HJ-3-241-2 (6 isomer: better FRET-based sensor) was separated by flash column chromatography on silica gel, using EtOAc:DCM (1:3) as the eluent. Yield HJ-3-241-1 (27 mg) and HJ-3-241-2 (28 mg) (89%). HJ-3-241-2: $^1$H NMR (400 MHz, CDCl$_3$) δ 8.75 (d, J=7.9 Hz, 1H), 8.63 (s, 1H), 8.14 (d, J=8.0 Hz, 1H), 8.07 (d, J=8.0 Hz, 1H), 7.64 (s, 1H), 7.40 (d, J=9.0 Hz, 1H), 6.64 (dd, J=9.0, 2.3 Hz, 1H), 6.59 (dd, 9.0, 1.8 Hz, 2H), 6.49 (d, J=2.0 Hz, 1H), 6.20 (d, J=7.9 Hz, 1H), 4.02-3.88 (m, 2H), 3.45 (q, J=7.1 Hz, 4H), 2.18-2.10 (m, 4H), 1.50-1.40 (m, 4H), 1.23 (d, J=7.2 Hz, 6H); $^{19}$F NMR (376 MHz, CDCl$_3$) δ −72.62, −72.63, −72.65, −126.11, −138.42; $^{13}$C NMR (100 MHz, CDCl$_3$) δ 166.78, 164.35, 162.87, 162.67, 157.80, 152.77, 152.27, 151.39, 149.73, 148.13, 145.93, 143.33, 142.83, 138.91, 136.72, 136.69, 136.62, 136.58, 135.36, 131.21, 129.92, 128.06, 127.94, 127.89, 127.76, 126.83, 126.74, 125.18, 123.45, 122.96, 120.26, 119.57, 119.50, 117.07, 113.88, 110.26, 110.15, 109.52, 109.48, 109.30, 109.27, 108.48, 96.74, 78.70, 49.11, 47.87, 45.23, 31.76, 31.54, 29.84, 12.56.

Example 7—Sensitive and Specific Detection of Superoxide with Green Fluorogenic Compound HKSOX-1

This Example shows that green fluorogenic Compound HKSOX-1 display high sensitivity and selectivity toward superoxide (O$_2^-$). The stock solution of HKSOX-1 (10 mM) is diluted in 0.1 M potassium phosphate buffer at pH 7.4 to obtain a 10 μM solution, with excitation and emission spectra at 509 nm and 534 nm, respectively. As expected, the probe HKSOX-1 was non-fluorescent (FIG. 1). Upon treatment of O$_2^-$ generated by enzymatic reaction of xanthine (X) and xanthine oxidase (XO), a dramatic increase (>500-fold enhancement) in fluorescence intensity was observed upon treatment with 10 equiv of O$_2^-$ generated by X/XO system in 10 min, whereas 10 equiv of other oxidants (H$_2$O$_2$, NO, $^1$O$_2$, ROO., TBHP, .OH, ONOO$^-$, HOCl), reductants (Fe$^{2+}$, ascorbic acid, 1,4-hydroquinone), esterase (10 U/mL) and GSH (5 mM, 500 equiv) caused negligible increase in the fluorescence signals. More importantly, the fluorescence intensity of HKSOX-1 upon treatment with X/XO in the presence of superoxide dismutase (SOD) decreased dramatically, suggesting that the fluorescent signal was caused by O$_2^-$.

Example 8—Sensitive and Specific Detection of Superoxide with Green Fluorogenic Compound HKSOX-2

Figure 2:
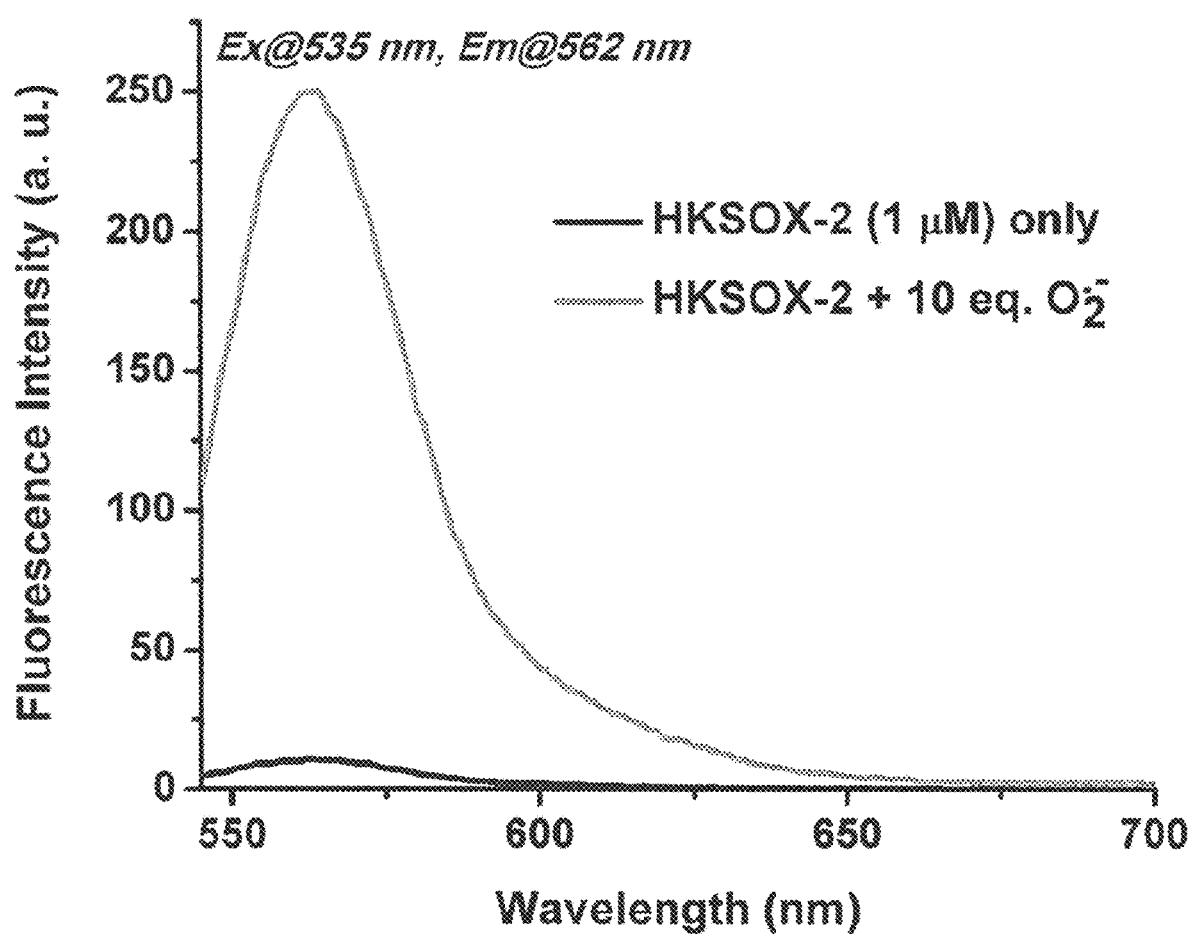
FIG. 2 shows fluorescence intensity of HKSOX-2 probe alone and in combination with $O_2^-$.
Figure 3:
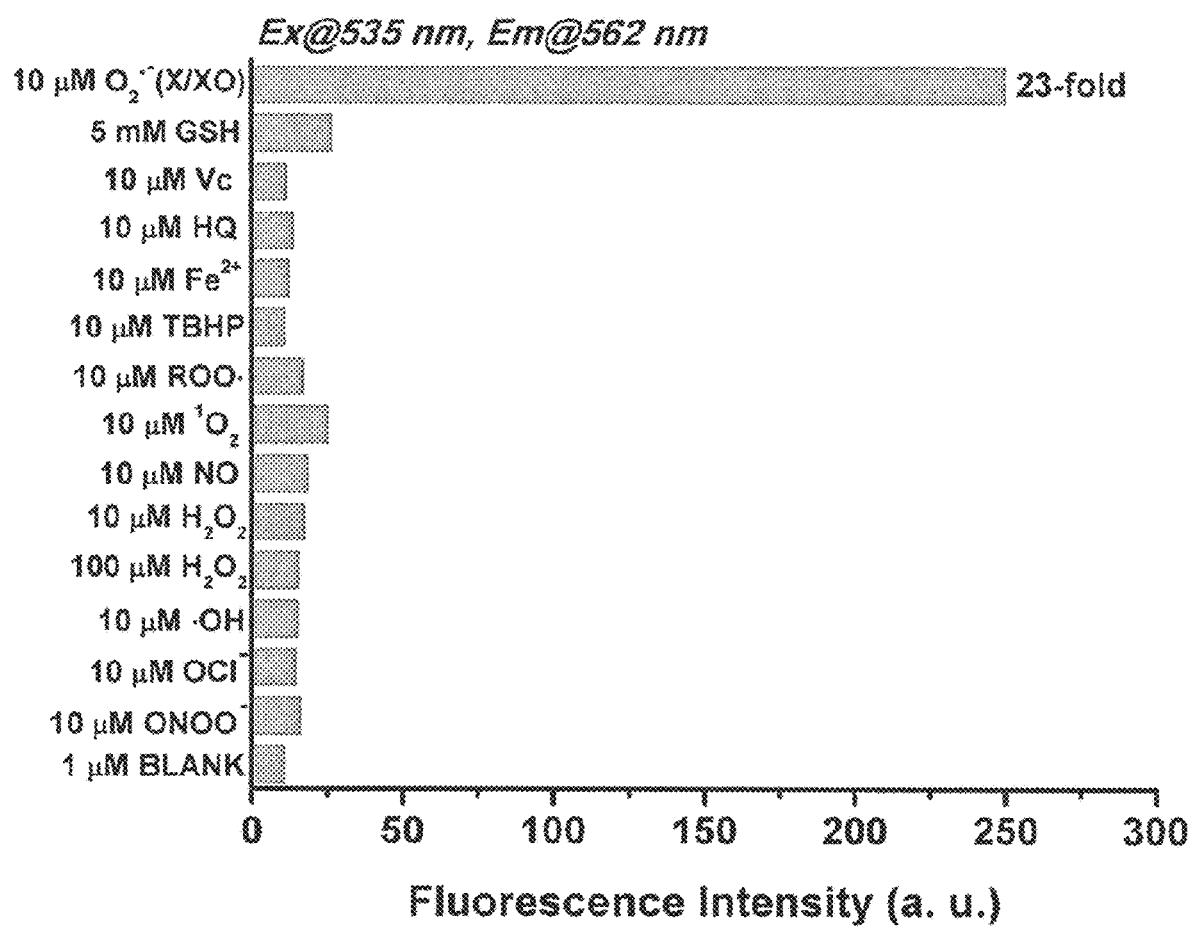
FIG. 3 shows fluorescence intensity of HKSOX-2 probe alone and in combination with $O_2^-$, other oxidants ($H_2O_2$, NO, $^1O_2$, ROO., TBHP, .OH, ONOO$^-$, HOCl), reductants ($Fe^{2+}$, ascorbic acid, 1,4-hydroquinone), esterase or GSH.

This Example shows that green fluorogenic Compound HKSOX-2 display high sensitivity and selectivity toward superoxide ($O_2^-$). The stock solution of HKSOX-2 (1 mM) is diluted in 0.1 M potassium phosphate buffer at pH 7.4 to obtain a 1 μM solution, with excitation and emission spectra at 535 nm and 562 nm, respectively. As expected, the probe HKSOX-2 was almost non-fluorescent (FIG. 2). Upon treatment of $O_2^-$ generated by enzymatic reaction of xanthine (X) and xanthine oxidase (XO), a dramatic increase (>23-fold enhancement) in fluorescence intensity was observed upon treatment with 10 equiv of $O_2^-$ generated by X/XO system in 15 min, whereas 10 equiv of other oxidants ($H_2O_2$, NO, $^1O_2$, ROO., TBHP, .OH, $ONOO^-$, HOCl), reductants ($Fe^{2+}$, ascorbic acid, 1,4-hydroquinone), esterase (10 U/mL) and GSH (5 mM, 500 equiv) caused negligible increase in the fluorescence signals (FIG. 3).

Example 9—Application of Subject Compounds in Cell Assay

Figure 4:
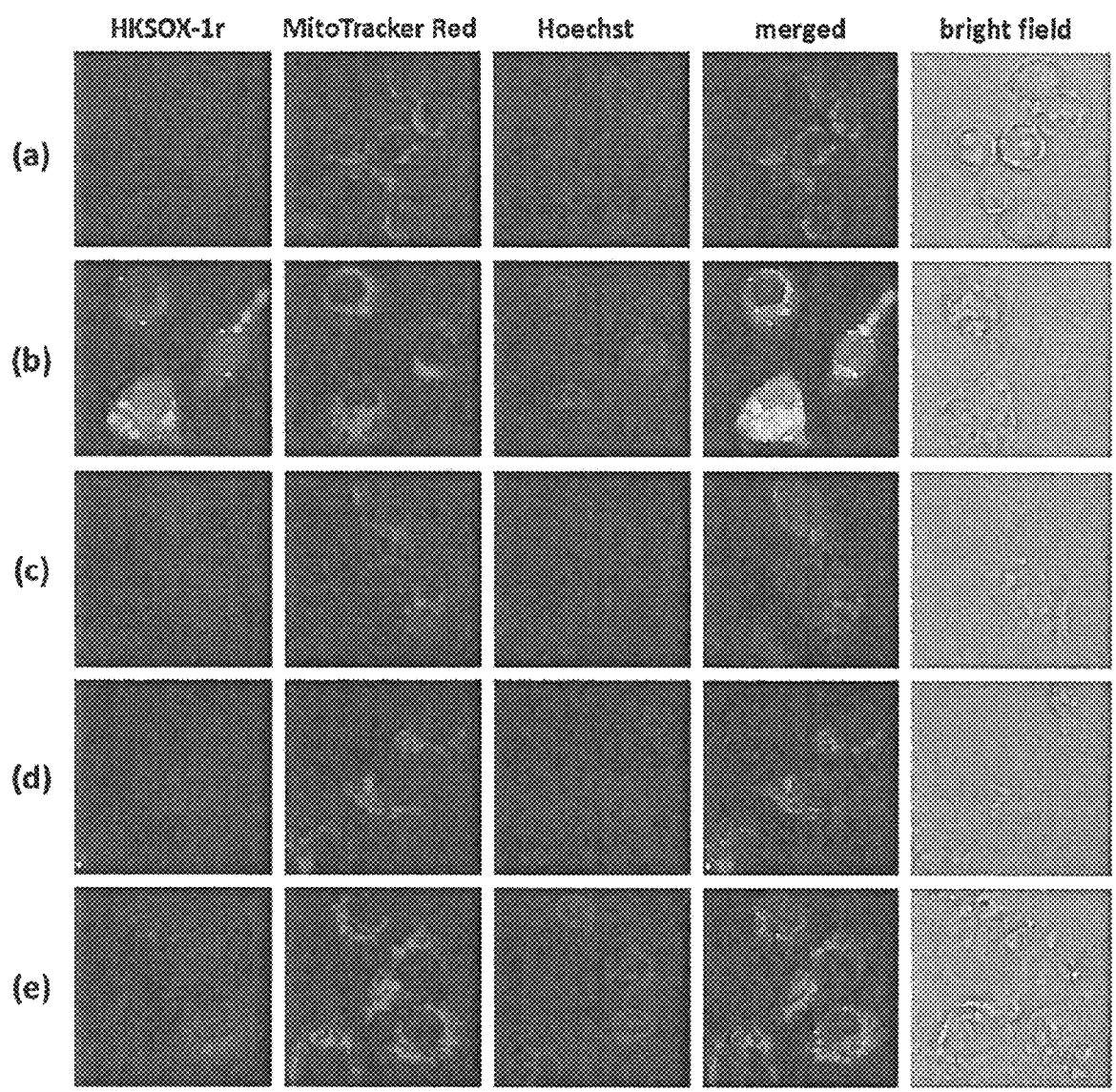
FIG. 4 shows confocal imaging (single photosection) of $O_2^-$ with HKSOX-1r in RAW264.7 mouse macrophages. The cells were co-stained with mitochondrial dye MitoTracker Red and nuclear DNA dye Hoechst 33342 and all fluorescence images merged. Shown are (a) untreated cells; (b) cells stimulated with LPS and IFN-γ for 14 hours, followed by HKSOX-1r staining (30 minutes); (c) cells co-treated with LPS/IFN-γ and gp91ds-tat for 14 hours, followed by HKSOX-1r staining (30 minutes); (d) cells stimulated with LPS/IFN-γ for 14 hours, followed by co-incubation of HKSOX-1r and FeTMPyP (30 minutes); and (e) cells stimulated with LPS/IFN-γ for 14 hours, followed by co-incubation of HKSOX-1r and TEMPOL (30 minutes)

We assessed the application of HKSOX-1r in confocal imaging of $O_2^-$ in different types of cell. For detection of endogenous $O_2^-$, we used mouse macrophages (RAW264.7 cells) as a cellular model. Bacterial lipopolysaccharide (LPS from *Salmonella typhimurium*; 500 ng/mL) and the proinflammatory cytokine interferon-γ (IFN-γ from mouse; 50 ng/mL) were used to activate macrophages. A highly selective and established peptide inhibitor (gp91ds-tat[12]; 2 μM) for NADPH oxidase (NOX2), the primary enzymatic source for $O_2^-$ during infection-related inflammation, was employed to validate the probe's specificity in cells. Additionally, the $O_2^-$ decomposition catalyst FeTMPyP (50 μM) and chemical scavenger TEMPOL (4-hydroxy-TEMPO; 300 μM) were used to remove $O_2^-$ in activated macrophages. After 14 h, macrophages stimulated with LPS/IFN-γ produced much stronger fluorescence signals relative to untreated ones (FIG. 4). This surge in $O_2^-$ production was greatly suppressed by the addition of gp91ds-tat. Similarly, in the presence of FeTMPyP or TEMPOL, HKSOX-1r fluorescence was substantially attenuated. These results suggest that our fluorescent probe can specifically detect $O_2^-$ generated in activated macrophages.

FIG. 4 shows confocal imaging (single photosection) of $O_2^-$ with HKSOX-1r (2 μM) in RAW264.7 mouse macrophages. The cells were co-stained with mitochondrial dye MitoTracker Red (50 nM) and nuclear DNA dye Hoechst 33342 (150 ng/mL) for 30 min. Merged: all fluorescence images merged. (a) Untreated cells; (b) cells stimulated with LPS (500 ng/mL) and IFN-γ (50 ng/mL) for 14 h, followed by HKSOX-1r staining for 30 min; (c) cells co-treated with LPS/IFN-γ and gp91ds-tat (2 μM) for 14 h, followed by HKSOX-1r staining (30 min); (d) cells stimulated with LPS/IFN-γ for 14 h, followed by co-incubation of HKSOX-1r and FeTMPyP (50 μM) for 30 min; (e) cells stimulated with LPS/IFN-γ for 14 h, followed by co-incubation of HKSOX-1r and TEMPOL (300 μM) for 30 min.

Figure 5:
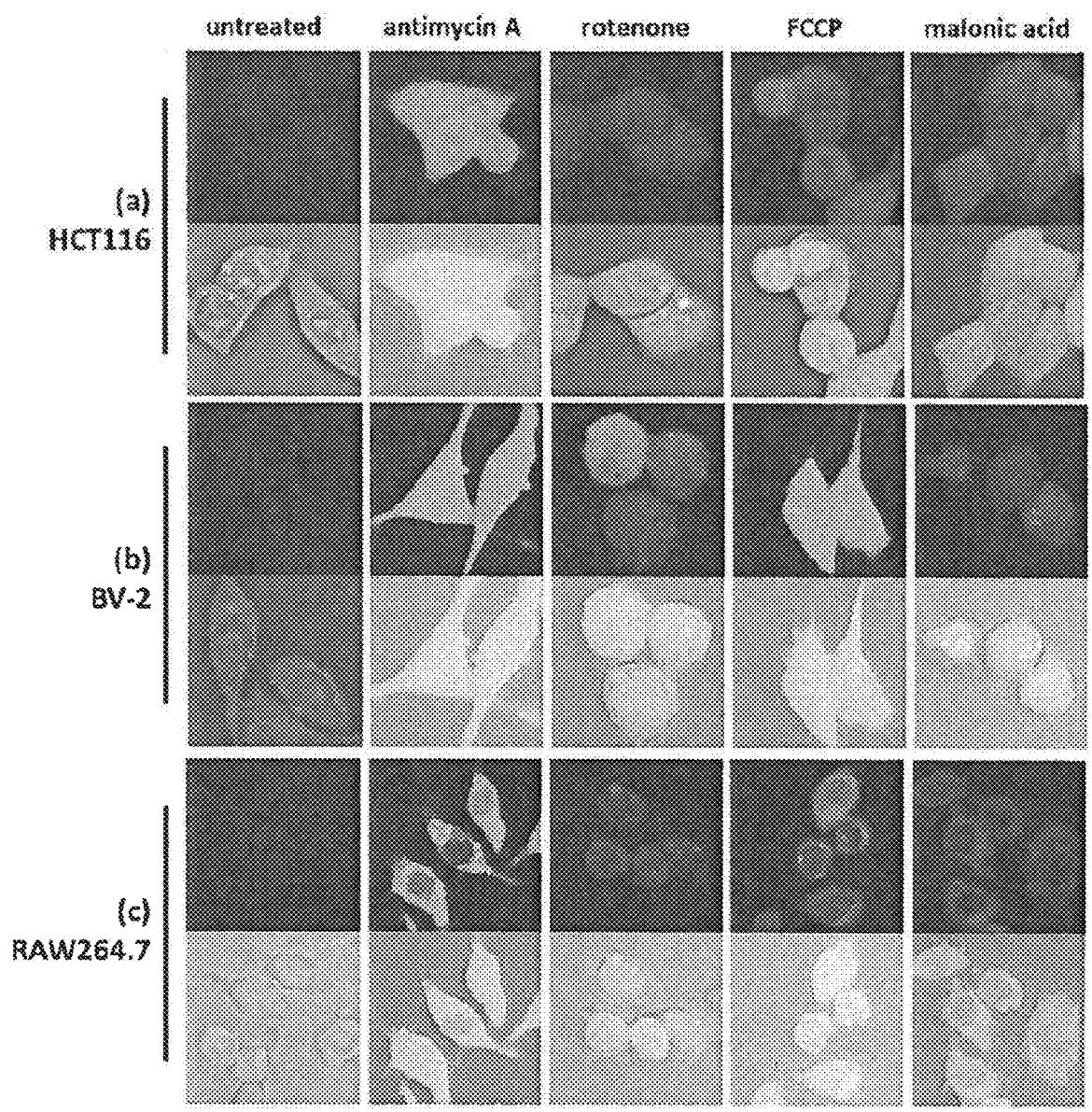
FIG. 5 shows confocal imaging of (a) HKSOX-1r co-incubated with or without mitochondrial respiratory inhibitors, antimycin A, rotenone, FCCP or malonic acid, in HCT116 human colon carcinoma cells for 30 minutes, (b) HKSOX-1r co-incubated with or without mitochondrial respiratory inhibitors in BV-2 mouse microglial cells for 30 minutes; and (c) HKSOX-1r co-incubated with or without mitochondrial respiratory inhibitors in RAW264.7 mouse macrophages for 30 minutes. In each group, upper panels show fluorescence images and lower panels show fluorescence images merged with bright field images.

As mitochondrial ROS has recently emerged as a key player in innate immune response and multiple pathologies including cancer, we also tested HKSOX-1r (2 μM) in detection of $O_2^-$ induced by mitochondrial respiratory inhibitors (30 min treatment): antimycin A (complex III inhibitor; 5 μM), rotenone (complex I inhibitor; 5 μM), FCCP (complex II inhibitor; 5 μM) and malonic acid (endogenous complex II inhibitor; 500 μM). To validate the inhibitor effects, three different types of cell were used: HCT116 (human colon cancer cells), RAW264.7 (mouse macrophages), and BV-2 (mouse microglia). Consistent with literature, all the mitochondrial respiratory inhibitors tested could rapidly induce mitochondrial $O_2^-$ production (FIG. 5), though with varying degrees of efficacy; antimycin A>FCCP>>rotenone>>malonic acid. At 2 μM, HKSOX-1r gave a strong fluorescence response upon induction of mitochondrial $O_2^-$, within a dynamic range of detection that allowed for differentiation of potent stimulants from weak ones. In addition, the probe can also be efficiently excited in two-photon modality in confocal imaging (FIG. 6).

FIG. 5(a) shows HKSOX-1r (2 μM) co-incubated with or without mitochondrial respiratory inhibitors antimycin A (5 μM), rotenone (5 μM), FCCP (5 μM) or malonic acid (500 μM) in HCT116 human colon carcinoma cells for 30 min. FIG. 5(b) shows HKSOX-1r (2 μM) co-incubated with or without mitochondrial respiratory inhibitors in BV-2 mouse microglial cells for 30 min. FIG. 5(c) shows HKSOX-1r (2 μM) co-incubated with or without mitochondrial respiratory inhibitors in RAW264.7 mouse macrophages for 30 min. In each group, upper: fluorescence images; lower: fluorescence images merged with bright field images.

Figure 6:
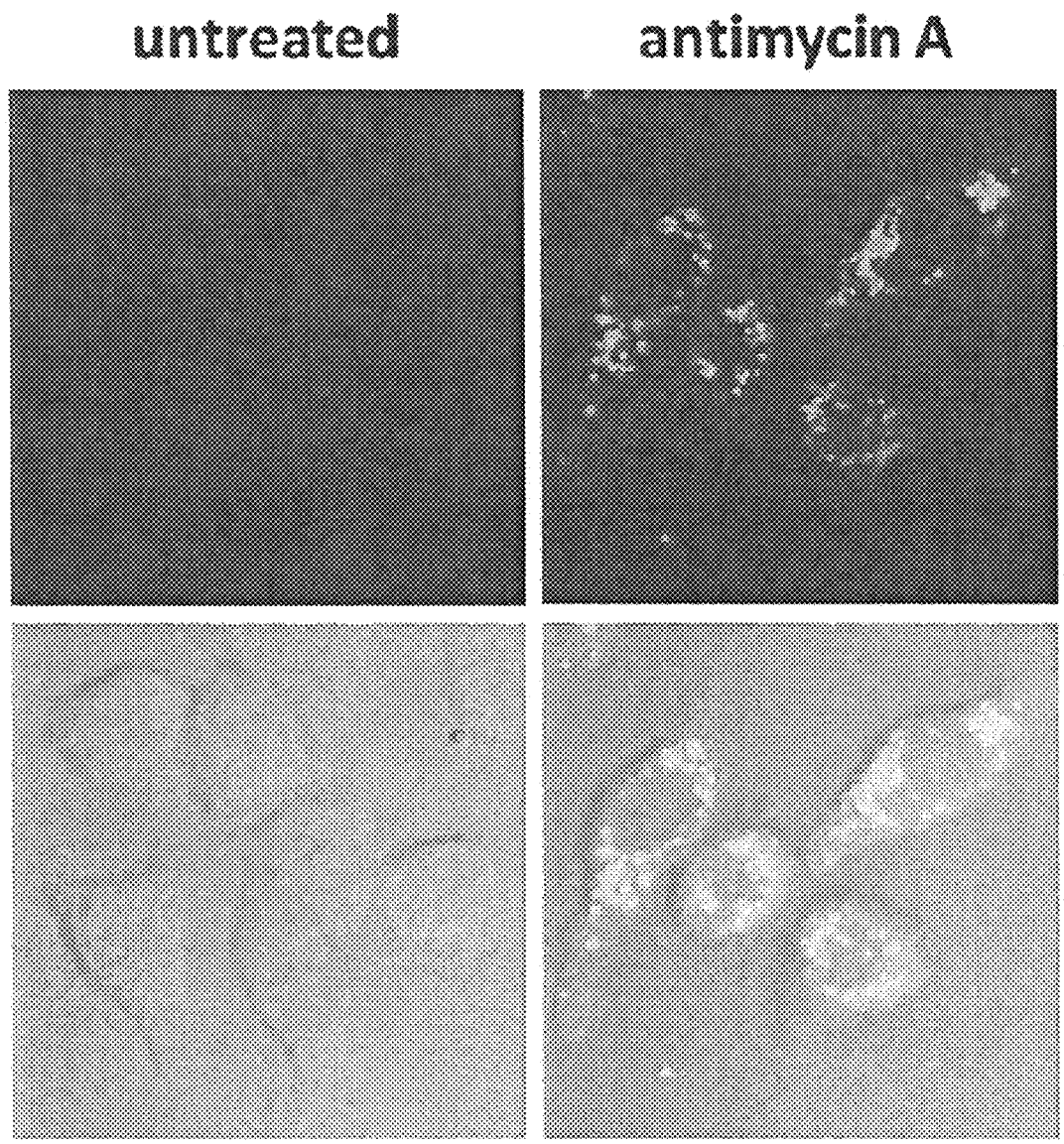
FIG. 6 shows two-photon confocal imaging of $O_2^-$ with HKSOX-1r RAW26.7 mouse macrophages. (left) Untreated cells incubated with probe alone for 30 minutes. (right) Cells co-incubated with probe and antimycin A for 30 minutes. Upper: fluorescence images; lower: fluorescence images merged with bright field images.

FIG. 6 shows two-photon confocal imaging of of $O_2^-$ with HKSOX-1r (2 μM) RAW264.7 mouse macrophages, (left) Untreated cells incubated with probe alone for 30 min. (right) Cells co-incubated with probe and antimycin A (5 μM) for 30 min. Upper: fluorescence images; lower: fluorescence images merged with bright field images.

Figure 7:
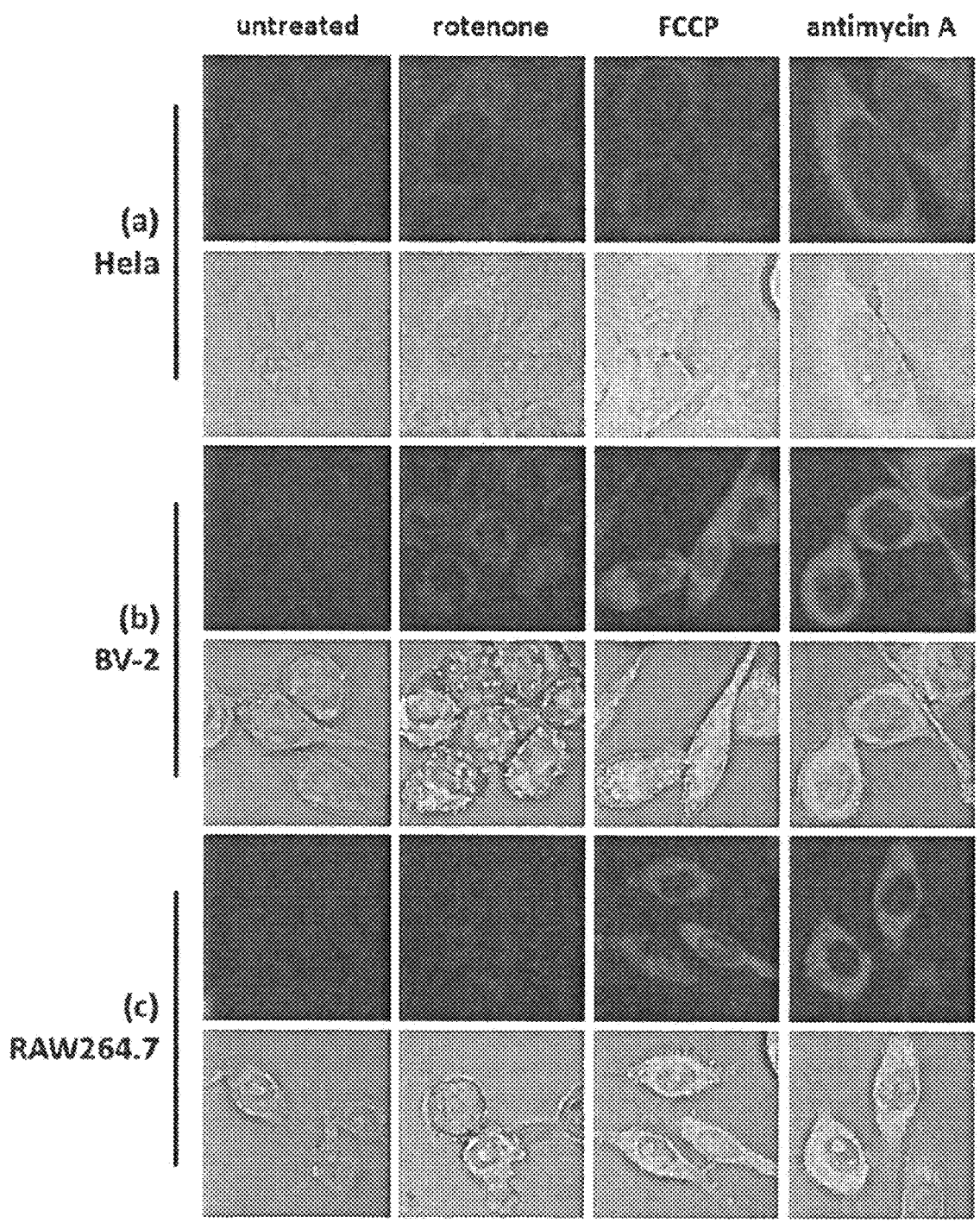
FIG. 7(a) shows HKSOX-2 co-incubated with or without mitochondrial respiratory inhibitors rotenone, FCCP and antimycin A in Hela cells for 30 minutes; (b) HKSOX-2 co-incubated with or without mitochondrial respiratory inhibitors in BV-2 mouse microglial cell for 30 minutes; and (c) HKSOX-2 co-incubated with or without mitochondrial respiratory inhibitors in RAW264.7 mouse macrophages for 30 minutes. In each group, upper panels show fluorescence images and lower panels show fluorescence images merged with bright field images.

We also tested HKSOX-2 (5 μM) in detection of $O_2^-$ induced by mitochondrial respiratory inhibitors (30 min treatment): antimycin A (complex III inhibitor; 10 μM), rotenone (complex I inhibitor; 10 μM) and FCCP (complex II inhibitor; 10 μM). To validate the inhibitor effects, three different types of cell were used: Hela (human cervical epithelial cancer cells), BV-2 (mouse microglia), and RAW264.7 (mouse macrophages). Consistent with literature, all the mitochondrial respiratory inhibitors tested could rapidly induce mitochondrial $O_2^-$ production (FIG. 7), though with varying degrees of efficacy: antimycin A>FCCP>>rotenone. At 5 μM, HKSOX-2 gave a strong fluorescence response upon induction of mitochondrial $O_2^-$, within a dynamic range of detection that allowed for differentiation of potent stimulants from weak ones.

FIG. 7(a) shows HKSOX-2 (5 μM) co-incubated with or without mitochondrial respiratory inhibitors rotenone (10 μM), FCCP (10 μM) and antimycin A (10 μM) in Hela cells for 30 min. FIG. 7(b) shows HKSOX-2 (5 μM) co-incubated with or without mitochondrial respiratory inhibitors in BV-2 mouse microglial cells for 30 min. FIG. 7(c) shows HKSOX-2 (5 μM) co-incubated with or without mitochondrial respiratory inhibitors in RAW264.7 mouse macrophages for 30 min. In each group, upper: fluorescence images; lower: fluorescence images merged with bright field images.

Figure 8:
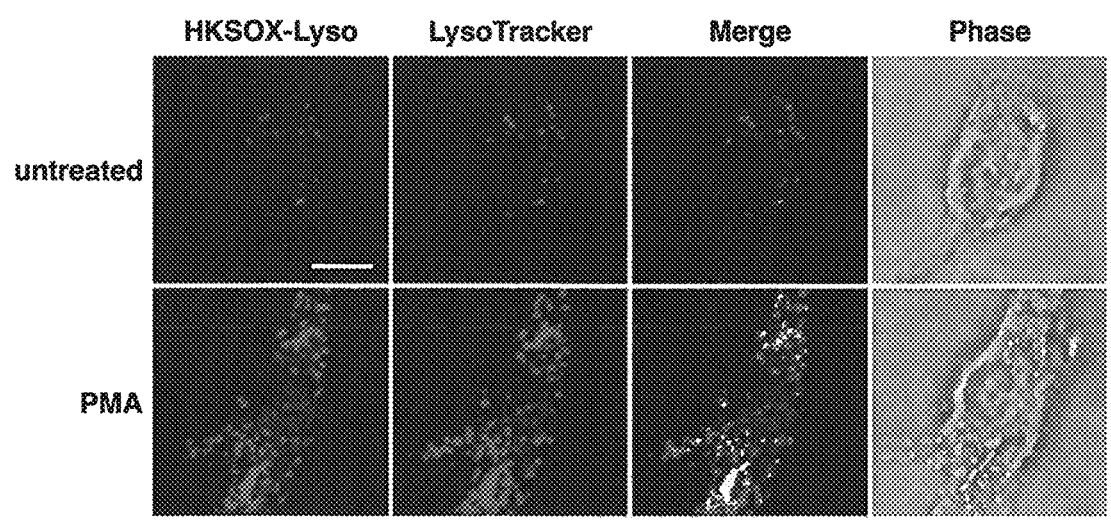
FIG. 8 shows the results of organelle dye co-staining with HKSOX-Lyso to assess its subcellular distribution in confocal imaging. The established mitochondrial dye, LysoTracker Green, was used to stain lysosomes in live cells. Co-staining was done by co-incubating HKSOX-Lyso (2.5 μM) with MitoTracker Green (200 nM) in RAW264.7 mouse macrophages for 30 min, in the presence or absence of two superoxide-inducers: PMA (phorbol-12-myristate-13-acetate; 500 ng/mL). The results demonstrated that the location of $O_2^-$ signal illustrated by HKSOX-Lyso was well merged with that of LysoTracker Green signal in PMA activated macrophages. Thus, we believe that our lysosome-targeted fluorescent probe HKSOX-Lyso can efficiently detect $O_2^-$ signal in lysosomes of activated macrophages.

We performed organelle dye co-staining with HKSOX-Lyso to assess its subcellular distribution in confocal imaging (FIG. 8). The established mitochondrial dye, LysoTracker Green, was used to stain lysosomes in live cells. Co-staining was done by co-incubating HKSOX-Lyso (2.5 μM) with MitoTracker Green (200 nM) in RAW264.7 mouse macrophages for 30 min, in the presence or absence of two superoxide-inducers: PMA (phorbol-12-myristate-13-acetate; 500 ng/mL). The results demonstrated that the location of $O_2^-$ signal illustrated by HKSOX-Lyso was well merged with that of LysoTracker Green signal in PMA activated macrophages. Thus, we believe that our lysosome targeted fluorescent probe HKSOX-Lyso can efficiently detect $O_2^-$ signal in lysosomes of activated macrophages.

FIG. 8 shows RAW264.7 mouse macrophages co-stained with HKSOX-Lyso (2.5 µM), LysoTracker Green (200 nM) for 30 min in the absence or presence of PMA (500 ng/mL).

Figure 9:
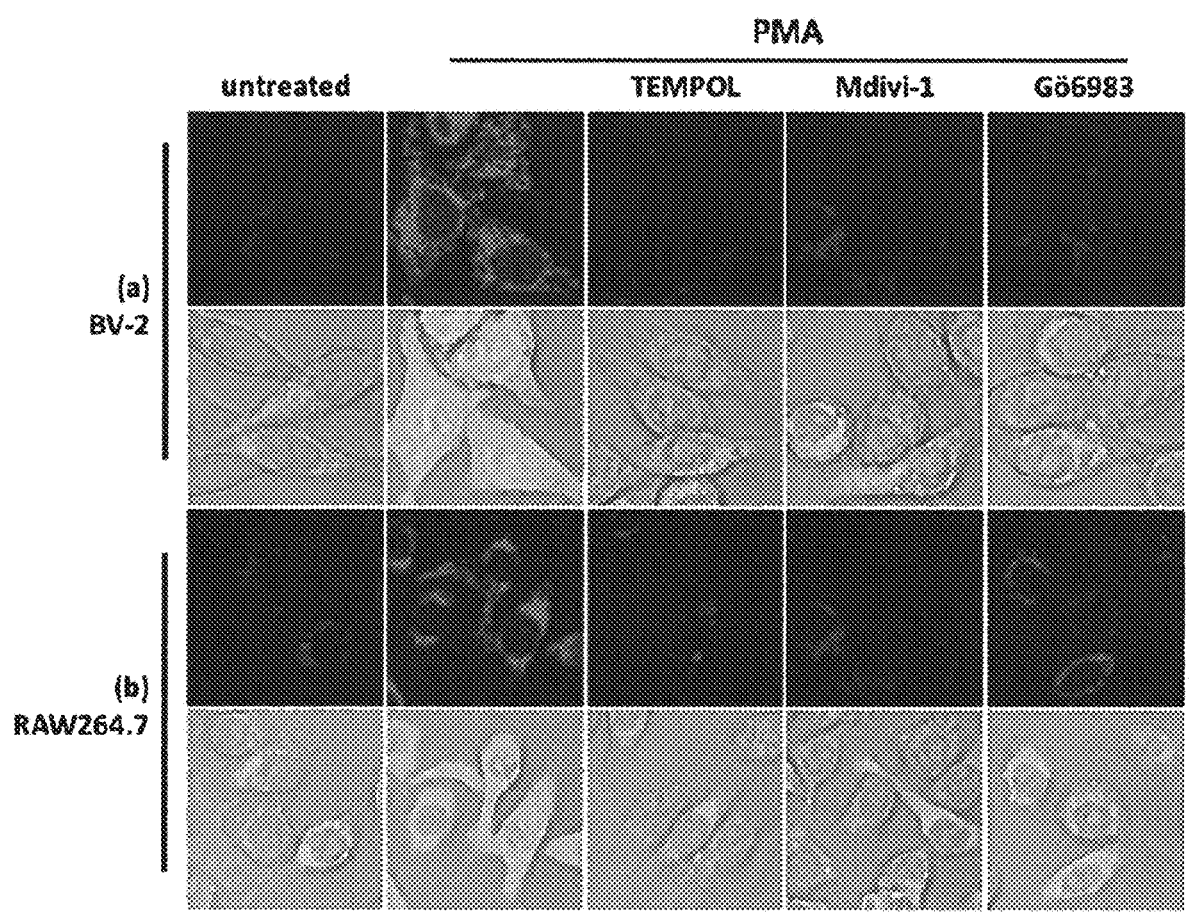
FIG. 9(a) shows HKSOX-2m co-incubated with or without PMA, TEMPOL, Mdivi-1 and Gö6983 in RAW264.7 mouse macrophages for 30 minutes, while FIG. 9(b) HKSOX-2m co-incubated with or without PMA, TEMPOL, Mdivi-1 and Gö6983 in BV-2 mouse microglial cells for 30 minutes.

We assessed the application of HKSOX-2m (2 µM) in confocal imaging of $O_2^-$ in different types of cell. For detection of endogenous $O_2^-$, two different cell types were used: mouse macrophages (RAW264.7 cells) and mouse microglia (BV-2 cells). PMA (phorbol-12-myristate-13-acetate), a PKC activator and acute $O_2^-$ inducer, was used to activate macrophages. The chemical scavenger TEMPOL (4-hydroxy-TEMPO; 300 µM) was used to remove $O_2^-$ in activated macrophages. Mdivi-1 (100 µM), a Drp-1 (dynamin-related protein 1) inhibitor that inhibits mitochondrial fission and subsequent mitochondrial $O_2^-$ production, was used to block mitochondrial $O_2^-$ formation. Additionally, Gö6983 (100 nM), a PKC inhibitor, was used to abolish PMA-mediated effects in $O_2^-$ induction. After 30 min, macrophages stimulated with PMA produced much stronger fluorescence signals relative to untreated ones (FIG. 9). This surge in $O_2^-$ production was greatly suppressed by the addition of TEMPOL. In the presence of Mdivi-1 and Gö6983, HKSOX-2m fluorescence was reduced to near basal level. Similarly, microglia stimulated with PMA produced much stronger fluorescence signals relative to untreated ones (FIG. 9). This surge in $O_2^-$ production was greatly suppressed by the addition of TEMPOL. In the presence of Mdivi-1 and Gö6983, the fluorescence of HKSOX-2m was reduced to near basal level. These results suggest that our fluorescent probe can specifically detect $O_2^-$ generated in activated macrophages and microglia.

FIG. 9(a) shows HKSOX-2m (2 µM) co-incubated with or without PMA (200 ng/mL), TEMPOL, (300 µM), Mdivi-1 (100 µM) and Gö6983 (100 nM) in RAW264.7 mouse macrophages for 30 min. FIG. 9(b) shows HKSOX-2m (2 µM) co-incubated with or without PMA (200 ng/mL), TEMPOL (300 µM), Mdivi-1 (100 µM) and Gö6983 (100 nM) in BV-2 mouse microglial cells for 30 min.

FIG. 10(a) shows RAW264.7 mouse macrophages co-stained with HKSOX-2m (2 µM), MitoTracker Green (50 nM) and Hoechst (150 ng/mL) for 30 min in the absence of superoxide inducers; (b) RAW264.7 mouse macrophages co-stained for 30 min with HKSOX-2m, MitoTracker Green and Hoechst in the presence of PMA (200 ng/mL); (c) RAW264.7 mouse macrophages co-stained with HKSOX-2m, MitoTracker Green and Hoechst for 30 min in the presence of yeast zymosan (50 µg/mL).

Figure 10:
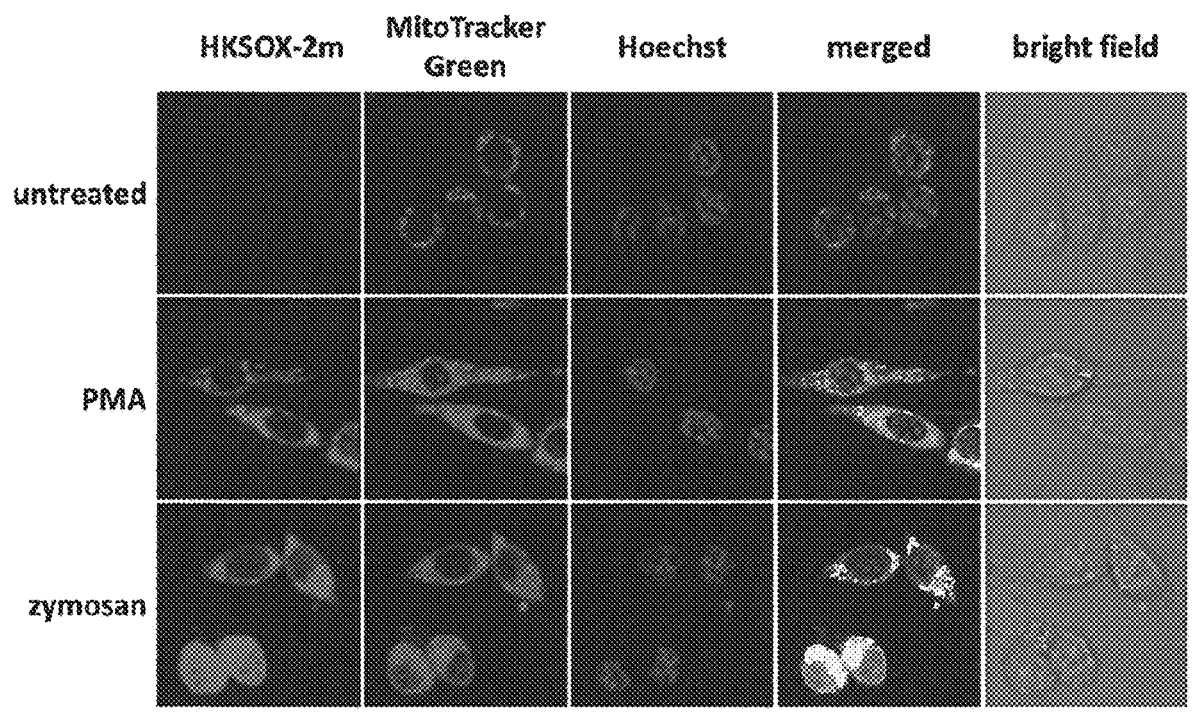
FIG. 10(a) shows RAW264.7 mouse macrophages co-stained with HKSOX-2m, MitoTracker Green and Hoechst for 30 minutes in the absence of superoxide inducers.
FIG. 10(b) shows RAW264.7 mouse macrophages co-stained for 30 minutes with HKSOX-2m, MitoTracker Green and Hoechst in the presence of PMA.
FIG. 10(c) shows RAW264.7 mouse macrophages co-stained with HKSOX-2m, MitoTracker Green and Hoechst for 30 minutes in the presence of yeast zymosan.

We performed organelle dye co-staining with HKSOX-2m to assess its subcellular distribution in confocal imaging (FIG. 10). The established mitochondrial dye, MitoTracker Green (50 nM), and nuclear DNA dye, Hoechst (150 ng/mL), were used to stain mitochondria and nucleus, respectively. Co-staining was done by co-incubating HKSOX-2 (2 µM) with MitoTracker Green and Hoechst in RAW264.7 mouse macrophages for 30 min, in the presence or absence of two superoxide-inducers: PMA (phorbol-12-myristate-13-acetate; 200 ng/mL) and yeast zymosan (50 µg/mL).

Figure 11:
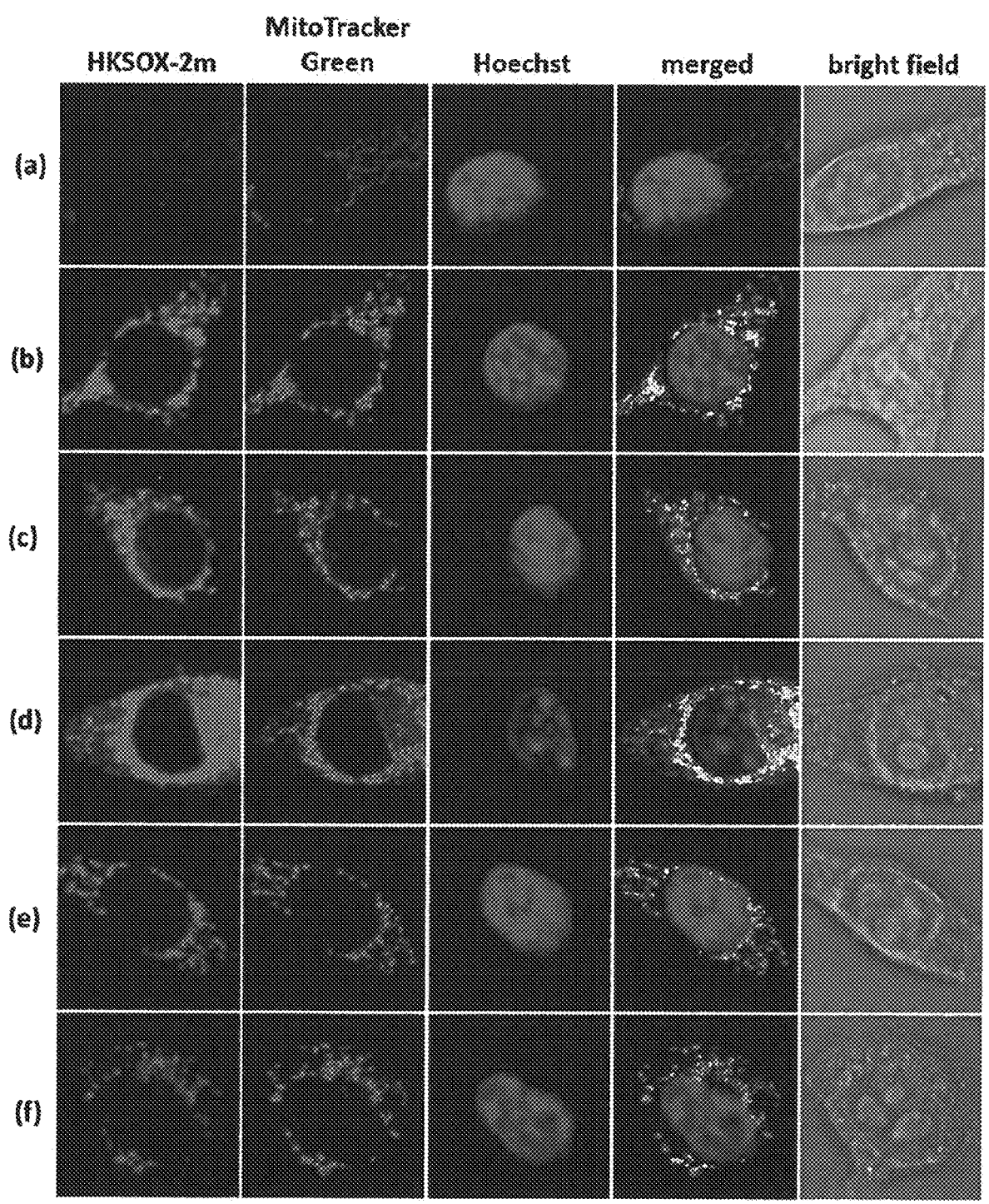
FIG. 11(a) shows BV-2 mouse microglial cells co-stained with HKSOX-2m, MitoTracker Green and Hoechst for 40 minutes in the absence of superoxide inducers.
FIG. 11(b) shows BV-2 mouse microglial cells co-stained with HKSOX-2m, MitoTracker Green and Hoechst for 40 minutes in the presence of PMA.
FIG. 11(c) shows BV-2 mouse microglial cells co-stained with HKSOX-2m, MitoTracker Green and Hoechst for 40 minutes in the presence of yeast zymosan.
FIG. 11(d) shows BV-2 mouse microglial cells co-stained with HKSOX-2m, MitoTracker Green and Hoechst for 40 minutes in the presence of diethyl succinate.
FIG. 11(e) shows BV-2 mouse microglial cells co-stained with HKSOX-2m, MitoTracker Green and Hoechst for 40 minutes in the presence of diethyl malonate; and (f) BV-2 mouse microglial cells co-stained with HKSOX-2m, MitoTracker Green and Hoechst for 40 minutes in the presence of rotenone.

FIG. 11(a) shows BV-2 mouse microglial cells co-stained with HKSOX-2m (2 µM), MitoTracker Green (10 µM) and Hoechst (1 µg/mL) for 40 min in the absence of superoxide inducers; FIG. 11(b) shows BV-2 mouse microglial cells co-stained with HKSOX-2m, MitoTracker Green and Hoechst for 40 min in the presence of PMA (200 ng/mL); FIG. 11(c) shows BV-2 mouse microglial cells co-stained with HKSOX-2m, MitoTracker Green and Hoechst for 40 min in the presence of yeast zymosan (50 µg/mL); (d) BV-2 mouse microglial cells co-stained with HKSOX-2m, MitoTracker Green and Hoechst for 40 min in the presence of diethyl succinate (2.5 mM); (e) BV-2 mouse microglial cells co-stained with HKSOX-2m, MitoTracker Green and Hoechst for 40 min in the presence of diethyl malonate (2.5 mM); (f) BV-2 mouse microglial cells co-stained with HKSOX-2m, MitoTracker Green and Hoechst for 40 min in the presence of rotenone (500 nM).

FIG. 12(a) shows BV-2 mouse microglial cells co-stained with MitoSOX Red™ (4 µM), MitoTracker Green (10 nM) and Hoechst (1 µg/mL) for 40 min in the absence of superoxide inducers; (b) BV-2 mouse microglial cells co-stained with MitoSOX Red™, MitoTracker Green and Hoechst for 40 min in the presence of PMA (200 ng/mL); (c) BV-2 mouse microglial cells co-stained with MitoSOX Red™, MitoTracker Green and Hoechst for 40 min in the presence of yeast zymosan (50 µg/mL); (d) BV-2 mouse microglial cells co-stained with MitoSOX Red™, MitoTracker Green and Hoechst for 40 min in the presence of diethyl succinate (15 mM); (e) BV-2 mouse microglial cells co-stained with MitoSOX Red™, MitoTracker Green and Hoechst for 40 min in the presence of diethyl malonate (15 mM); (f) BV-2 mouse microglial cells co-stained with MitoSOX Red™, MitoTracker Green and Hoechst for 40 min in the presence of rotenone (500 nM).

Figure 12:
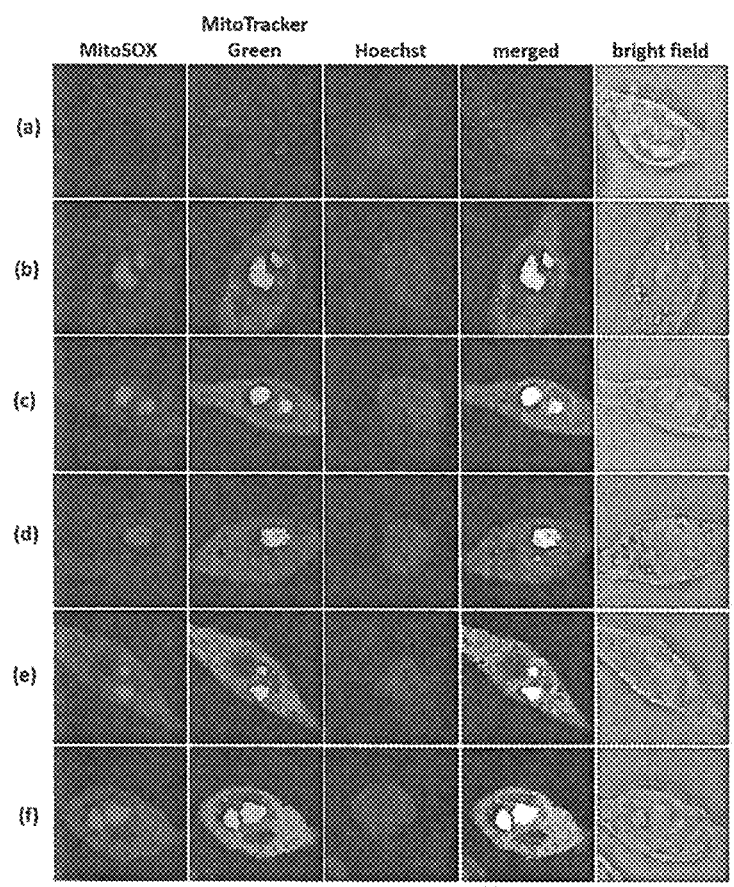
FIG. 12(a) shows BV-2 mouse microglial cells co-stained with MitoSOX Red™, MitoTracker Green and Hoechst for 40 minutes in the absence of superoxide inducers.
FIG. 12(b) shows BV-2 mouse microglial cells co-stained with MitoSOX Red™, MitoTracker Green and Hoechst for 40 minutes in the presence of PMA.
FIG. 12(c) shows BV-2 mouse microglial cells co-stained with MitoSOX Red™, MitoTracker Green and Hoechst for 40 minutes in the presence of yeast zymosan.
FIG. 12(d) shows BV-2 mouse microglial cells co-stained with MitoSOX Red™, MitoTracker Green and Hoechst for 40 minutes in the presence of diethyl succinate.
FIG. 12(e) shows BV-2 mouse microglial cells co-stained with MitoSOX Red™, MitoTracker Green and Hoechst for 40 minutes in the presence of diethyl malonate.
FIG. 12(f) shows BV-2 mouse microglial cells co-stained with MitoSOX Red™, MitoTracker Green and Hoechst for 40 minutes in the presence of rotenone.

To further validate the performance of HKSOX-2m as a mitochondria-targeting superoxide probe, we conducted confocal imaging of HKSOX-2m with multiple superoxide inducers in BV-2 mouse microglial cells (FIG. 11), and compared HKSOX-2m's performance with that of MitoSOX Red™ (a widely used commercial fluorescent probe for mitochondrial superoxide detection; Invitrogen), by using the same drugs as stimulants (FIG. 12). Briefly, BV-2 cells were co-incubated for 40 min with probes (HKSOX-2m or MitoSOX Red™) and general superoxide inducers (PMA and zymosan, which elicit superoxide production from multiple superoxide sources including mitochondria) or specific mitochondrial superoxide inducers (diethyl succinate, diethyl malonate, and rotenone, which target the mitochondrial respiratory chain complexes). Consistently, in HKSOX-2m imaging (FIG. 11), moderate to strong fluorescence was easily reproduced with various stimulants, and clear mitochondrial morphology could be discerned in the drug-treated groups. At a working dose of 2 µM, the fluorescence turn-on response of HKSOX-2m was highly efficient (Em 559-623 nm band-pass), with a low laser output (12%) being sufficient for excitation (Ex 543 nm). Results for co-staining with MitoTracker Green (10 nM) and Hoechst 33342 (1 µg/mL) indicate that HKSOX-2m was cytoplasmically distributed and well co-localized with mitochondria in cells. Slight spatial shifts in fluorescence signal were occasionally observed in the HKSOX-2m and MitoTracker Green channels, which could be accounted for by mitochondrial dynamics and time lag in confocal laser scanning for each channel. In contrast, in MitoSOX Red™ imaging (FIG. 12), low to moderate fluorescence was observed when cells were challenged with the same stimulants. However, no distinct mitochondrial morphology could be observed in the MitoSOX Red™ channel (Em 565-615 nm band-pass). In fact, fluorescence distribution of the mitochondrial dye MitoTracker Green (Ex 488; Em 505 nm long-pass) was grossly distorted in the presence of MitoSOX Red™ (due to its broad tailing in emission spectrum), resulting in a loss of mitochondrial morphology. In addition, as is well known in the fluorescent sensor literature, Mito- SOX Red™ stained nuclear DNA and fluoresced brightly in the nucleus, which clearly would contribute to significant artifacts in both imaging and quantitative assays. At a near-toxic working dose of 4 μM (its maximal dose being 5 μM according to manufacturer's protocol, which is cytotoxic to cells in extended incubation), the fluorescence turn-on response of MitoSOX Red™ was rather sluggish, requiring high laser output (100%) for excitation (Ex 543 nm). Taken as a whole, HKSOX-2m evidently out-performed MitoSOX Red™ in several assessment criteria as a mitochondrial superoxide probe in live cell imaging, namely: selectivity, sensitivity, and cellular distribution (FIG. 13).

Figure 13:
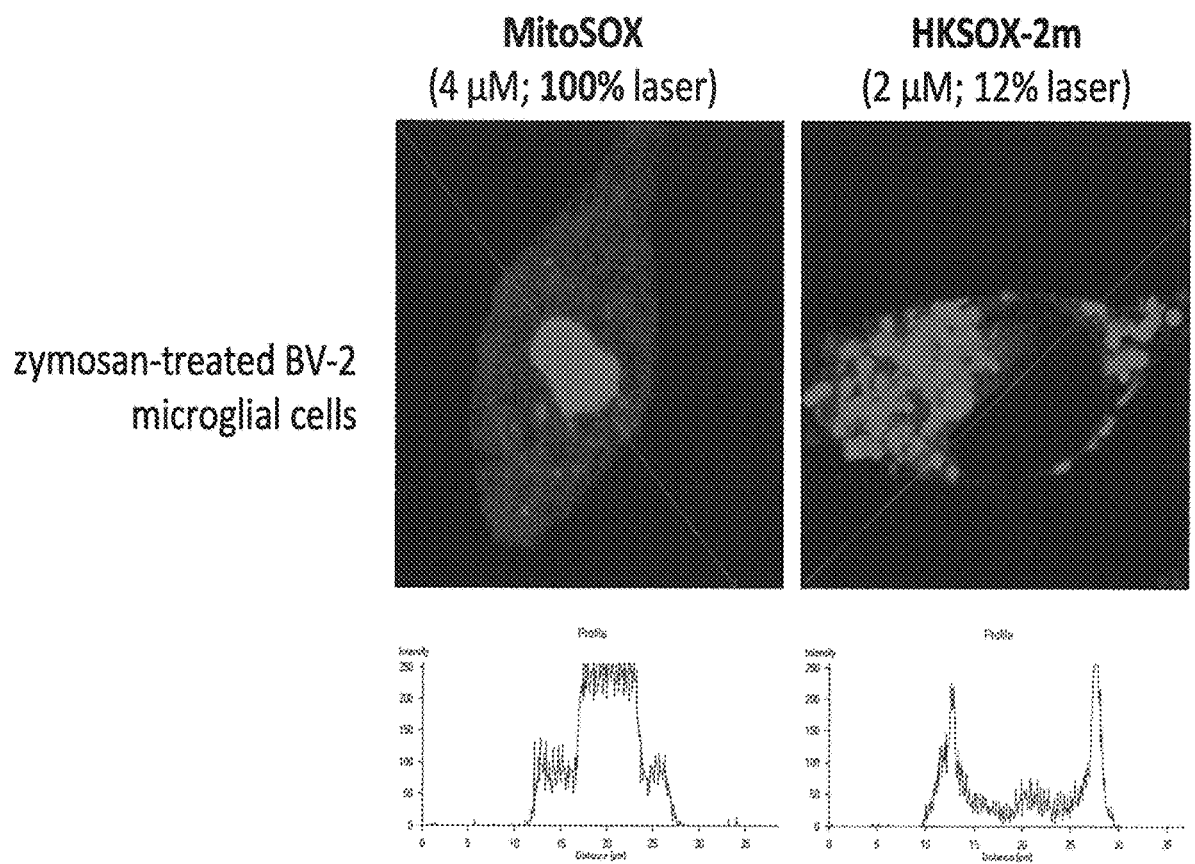
FIG. 13 shows fluorescence intensity profiles across nuclear and cytoplasmic regions for MitoSOX Red™ (4 μM) and HKSOX-2m (2 μM) is zymosan-treated BV-2 mouse microglial cells, as analyzed by Zeiss LSM 510 Meta software.

FIG. 13 shows fluorescence intensity profiles across nuclear and cytoplasmic regions for MitoSOX Red™ (4 μM) and HKSOX-2m (2 μM) in zymosan-treated BV-2 mouse microglial cells, as analyzed by Zeiss LSM 510 Meta software.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

We claim:

1. A fluorogenic probe composition for detecting superoxide, comprising a compound having one of the following formulas 3-4, 9, 10 and 13-20:

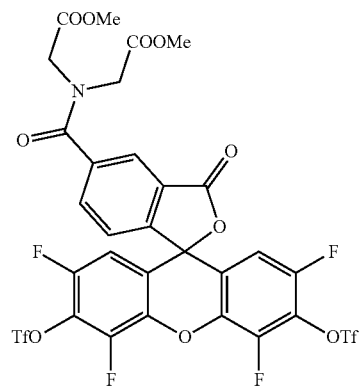

3

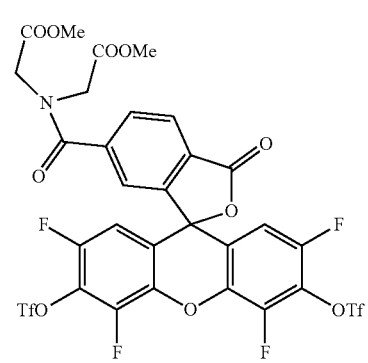

4

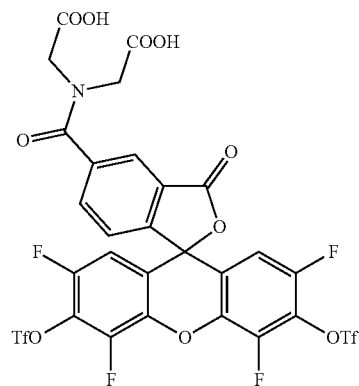

9

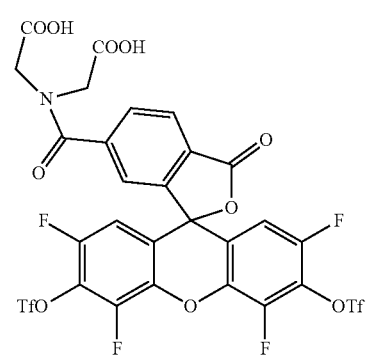

10

-continued
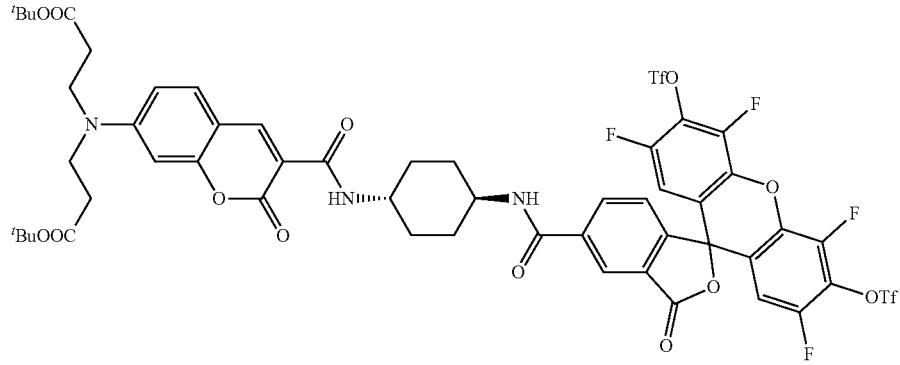
13
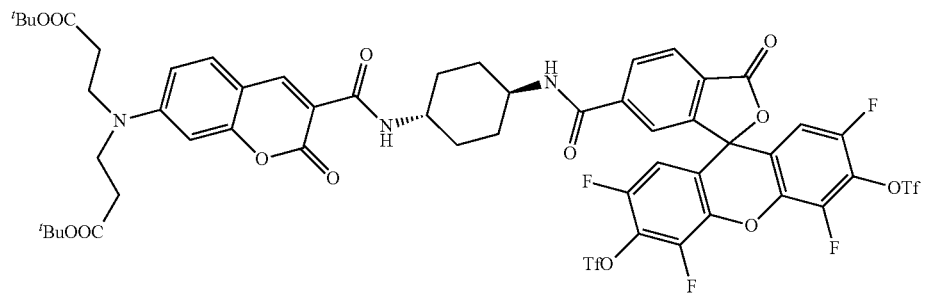
14
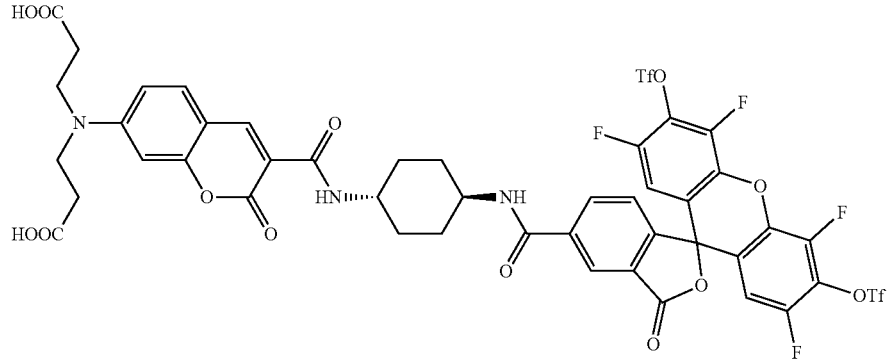
15
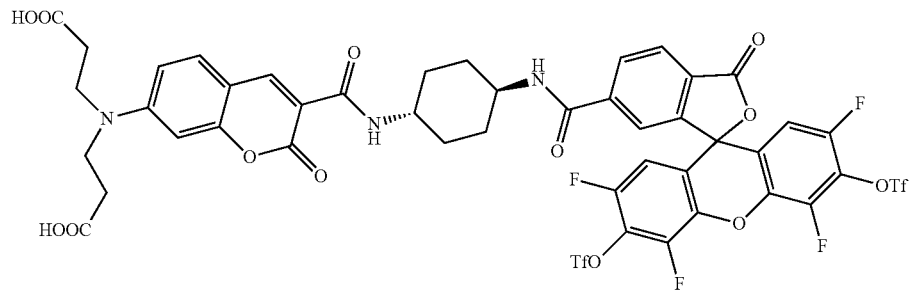
16
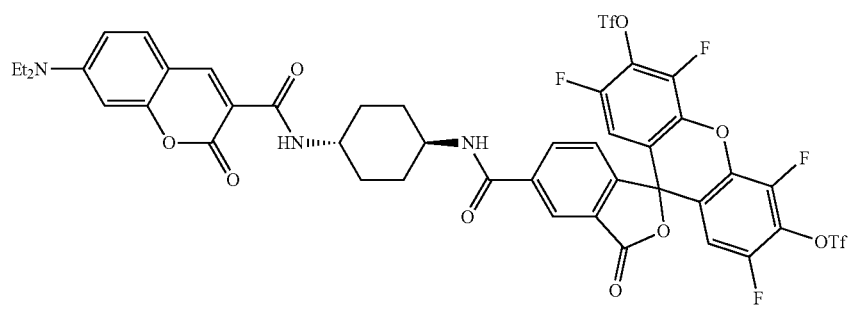
17

-continued

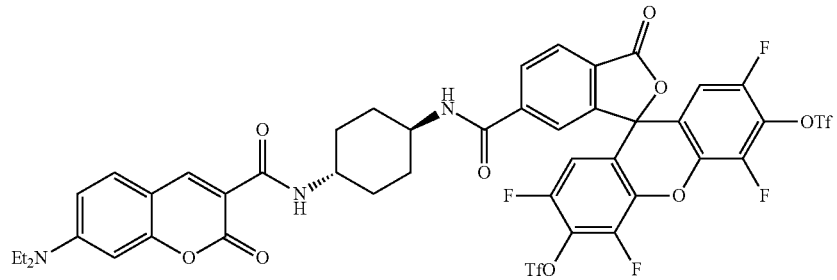

18

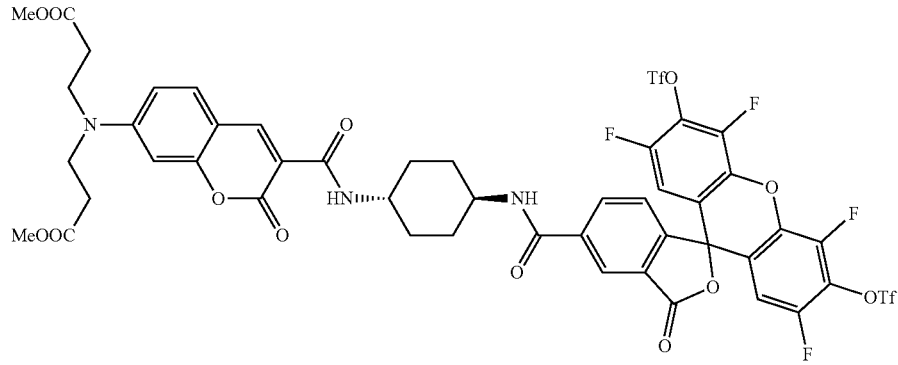

19

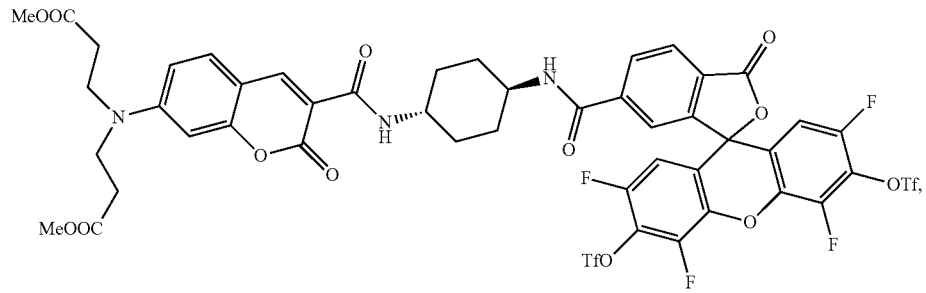

20 wherein the compound reacts with superoxide to form one or more fluorescent compounds.

2. The fluorogenic probe composition of claim 1, further comprising a carrier.

3. The fluorogenic probe composition of claim 1, wherein the fluorogenic probe composition further comprises a solvent, an acid, a base, a buffer solution, or a combination thereof.

4. A method for detecting the presence of, and/or determining the level of superoxide in a sample, comprising:
   a) contacting the fluorogenic probe composition of claim 1 with the sample to form a fluorescent compound; and
   b) determining fluorescence property of the fluorescent compound.

5. The method of claim 4, wherein the sample is a chemical sample or biological sample.

6. The method of claim 4, wherein the sample is a biological sample comprising a microorganism, or a cell or tissue.

7. A method for detecting the presence of, or determining the level of superoxide in vivo in an organism, comprising:
   a) administering the fluorogenic probe composition of claim 1 to the organism to form a fluorescent compound; and
   b) determining fluorescence property of the fluorescent compound.

8. A high-throughput screening method for detecting the presence of, or determining the level of, superoxide in samples, wherein the high-throughput method comprises the steps of:
   a) contacting the fluorogenic probe composition of claim 1 with the samples to form one or more fluorescent compounds; and
   b) determining fluorescence properties of the fluorescent compounds to determine the presence and/or amount of peroxynitrite in the samples.

9. A high-throughput method for screening one or more target compounds that increase or decrease the level of superoxide, wherein the high-throughput method comprises the steps of:
   a) contacting the fluorogenic probe composition of claim 1 with target compounds to form one or more fluorescent compounds; and
   b) measuring fluorescence properties of the florescent compounds to determine the presence and/or amount of the target compounds.

* * * * *